United States Patent
Doering et al.

(10) Patent No.: US 11,634,726 B2
(45) Date of Patent: Apr. 25, 2023

(54) CAS9 NUCLEIC ACID MOLECULES AND THEIR USE

(71) Applicant: Emory University, Atlanta, GA (US)

(72) Inventors: Christopher B. Doering, Atlanta, GA (US); H. Trent Spencer, Atlanta, GA (US); Harrison C. Brown, Atlanta, GA (US)

(73) Assignee: Emory University, Atlanta, GA (US)

( * ) Notice: Subject to any disclaimer, the term of this patent is extended or adjusted under 35 U.S.C. 154(b) by 320 days.

(21) Appl. No.: 16/896,021

(22) Filed: Jun. 8, 2020

(65) Prior Publication Data

US 2020/0299722 A1     Sep. 24, 2020

Related U.S. Application Data

(63) Continuation of application No. 15/673,115, filed on Aug. 9, 2017, now Pat. No. 10,724,050.

(60) Provisional application No. 62/372,584, filed on Aug. 9, 2016.

(51) Int. Cl.
*C12N 15/85*   (2006.01)
*C12N 9/96*    (2006.01)
*C12Q 1/68*    (2018.01)

(52) U.S. Cl.
CPC ............. *C12N 15/85* (2013.01); *C12N 9/96* (2013.01); *C12Q 1/68* (2013.01); *C12N 2310/20* (2017.05)

(58) Field of Classification Search
None
See application file for complete search history.

(56) References Cited

U.S. PATENT DOCUMENTS

2016/0153005 A1   6/2016   Zhang et al.

FOREIGN PATENT DOCUMENTS

WO   WO 2016/168728   10/2016

OTHER PUBLICATIONS

Aravalli and Steer, "CRISPR/Cas9 Therapeutics for Liver Diseases," *J Cell Biochem* 119.6: 4265-4278, Jun. 2018.
Dittmar et al., "Tissue-Specific Differences in Human Transfer RNA Expression," *PLoS Genetics* 2.12: e221, Dec. 22, 2006 (9 pages).
GenBank Accession No. CP014139.1, available at https://www.ncbi.nlm.nih.gov/nuccore/CP014139.1, as accessed Dec. 4, 2017.
GenBank Accession No. CP012045.1, available at https://www.ncbi.nlm.nih.gov/nuccore/CP012045.1, as accessed Dec. 4, 2017.
Mali et al., "RNA-Guided Human Genome Engineering via Cas9," *Science* 339.6121: 823-826, Feb. 15, 2013.
Quax et al., "Codon Bias as a Means to Fine-Tune Gene Expression," *Molecular Cell* 59.2: 149-161, Jul. 16, 2015.

*Primary Examiner* — James D Schultz
*Assistant Examiner* — Kimberly A Aron
(74) *Attorney, Agent, or Firm* — Klarquist Sparkman, LLP

(57) ABSTRACT

Described are recombinant nucleic acid molecules for increased expression of Cas9 in human liver. In some embodiments, the recombinant nucleic acid molecules are provided in compositions and methods for gene editing, specifically using Clustered Regularly Interspaced Short Palindromic Repeats (CRISPR).

14 Claims, 18 Drawing Sheets

Specification includes a Sequence Listing.

FIG. 1A

*Homo sapiens* [gbpri]: 93487 CDS's (40662582 codons)

fields: [triplet] [frequency: per thousand] ([number])

| | | | |
|---|---|---|---|
| UUU 17.6(714298) | UCU 15.2(618711) | UAU 12.2(495699) | UGU 10.6(430311) |
| UUC 20.3(824692) | UCC 17.7(718892) | UAC 15.3(622407) | UGC 12.6(513028) |
| UUA 7.7(311881) | UCA 12.2(496448) | UAA 1.0( 40285) | UGA 1.6( 63237) |
| UUG 12.9(525688) | UCG 4.4(179419) | UAG 0.8( 32109) | UGG 13.2(535595) |
| CUU 13.2(536515) | CCU 17.5(713233) | CAU 10.9(441711) | CGU 4.5(184609) |
| CUC 19.6(796638) | CCC 19.8(804620) | CAC 15.1(613713) | CGC 10.4(423516) |
| CUA 7.2(290751) | CCA 16.9(688038) | CAA 12.3(501911) | CGA 6.2(250760) |
| CUG 39.6(1611801) | CCG 6.9(281570) | CAG 34.2(1391973) | CGG 11.4(464485) |
| AUU 16.0(650473) | ACU 13.1(533609) | AAU 17.0(689701) | AGU 12.1(493429) |
| AUC 20.8(846466) | ACC 18.9(768147) | AAC 19.1(776603) | AGC 19.5(791383) |
| AUA 7.5(304565) | ACA 15.1(614523) | AAA 24.4(993621) | AGA 12.2(494682) |
| AUG 22.0(896005) | ACG 6.1(246105) | AAG 31.9(1295568) | AGG 12.0(488463) |
| GUU 11.0(448607) | GCU 18.4(750096) | GAU 21.8(885429) | GGU 10.8(437126) |
| GUC 14.5(588138) | GCC 27.7(1127679) | GAC 25.1(1020595) | GGC 22.2(903565) |
| GUA 7.1(287712) | GCA 15.8(643471) | GAA 29.0(1177632) | GGA 16.5(669873) |
| GUG 28.1(1143534) | GCG 7.4(299495) | GAG 39.6(1609975) | GGG 16.5(669768) |

FIG. 2A
mouse genome vs human genome

| Codon | AA | Human | Codon | AA | Mouse:Human |
|---|---|---|---|---|---|
| GCA | A | 1.02 | AAT | N | 0.92 |
| GCC | A | 0.95 | CCA | P | 1.04 |
| GCG | A | 0.88 | CCC | P | 0.94 |
| GCT | A | 1.10 | CCG | P | 0.91 |
| TGC | C | 0.95 | CCT | P | 1.07 |
| TGT | C | 1.06 | CAA | Q | 0.98 |
| GAC | D | 1.03 | CAG | Q | 1.01 |
| GAT | D | 0.96 | AGA | R | 1.02 |
| GAA | E | 0.96 | AGG | R | 1.05 |
| GAG | E | 1.03 | CGA | R | 1.10 |
| TTC | F | 1.04 | CGC | R | 0.92 |
| TTT | F | 0.95 | CGG | R | 0.92 |
| GGA | G | 1.04 | CGT | R | 1.06 |
| GGC | G | 0.97 | AGC | S | 0.99 |
| GGG | G | 0.94 | AGT | S | 1.03 |
| GGT | G | 1.09 | TCA | S | 0.95 |
| CAC | H | 1.02 | TCC | S | 1.00 |
| CAT | H | 0.98 | TCG | S | 0.94 |
| ATA | I | 0.96 | TCT | S | 1.05 |
| ATC | I | 1.06 | ACA | T | 1.04 |
| ATT | I | 0.94 | ACC | T | 0.98 |
| AAA | K | 0.91 | ACG | T | 0.91 |
| AAG | K | 1.07 | ACT | T | 1.02 |
| CTA | L | 1.12 | GTA | V | 1.03 |
| CTC | L | 1.02 | GTC | V | 1.04 |
| CTG | L | 0.99 | GTG | V | 0.99 |
| CTT | L | 1.01 | GTT | V | 0.95 |
| TTA | L | 0.87 | TGG | W | 1.00 |
| TTG | L | 1.03 | TAC | Y | 1.02 |
| ATG | M | 1.00 | TAT | Y | 0.97 |
| AAC | N | 1.07 | | | |

FIG. 2B
hepatocyte vs whole human

| Codon | AA | Liver:Human | Codon | AA | Liver:Human |
|---|---|---|---|---|---|
| GCA | A | 0.83 | AAT | N | 0.87 |
| GCC | A | 1.10 | CCA | P | 0.87 |
| GCG | A | 0.94 | CCC | P | 1.17 |
| GCT | A | 1.02 | CCG | P | 0.88 |
| TGC | C | 1.10 | CCT | P | 0.98 |
| TGT | C | 0.88 | CAA | Q | 0.94 |
| GAC | D | 1.14 | CAG | Q | 1.02 |
| GAT | D | 0.84 | AGA | R | 0.84 |
| GAA | E | 0.83 | AGG | R | 0.95 |
| GAG | E | 1.13 | CGA | R | 0.92 |
| TTC | F | 1.21 | CGC | R | 1.31 |
| TTT | F | 0.75 | CGG | R | 1.04 |
| GGA | G | 0.92 | CGT | R | 0.87 |
| GGC | G | 1.10 | AGC | S | 1.04 |
| GGG | G | 1.12 | AGT | S | 0.80 |
| GGT | G | 0.74 | TCA | S | 0.86 |
| CAC | H | 1.01 | TCC | S | 1.28 |
| CAT | H | 0.98 | TCG | S | 1.10 |
| ATA | I | 0.65 | TCT | S | 0.91 |
| ATC | I | 1.30 | ACA | T | 0.74 |
| ATT | I | 0.78 | ACC | T | 1.32 |
| AAA | K | 0.81 | ACG | T | 1.05 |
| AAG | K | 1.15 | ACT | T | 0.77 |
| CTA | L | 0.84 | GTA | V | 0.69 |
| CTC | L | 1.18 | GTC | V | 1.09 |
| CTG | L | 1.19 | GTG | V | 1.12 |
| CTT | L | 0.76 | GTT | V | 0.72 |
| TTA | L | 0.52 | TGG | W | 1.00 |
| TTG | L | 0.85 | TAC | Y | 1.13 |
| ATG | M | 1.00 | TAT | Y | 0.83 |
| AAC | N | 1.11 | | | |

FIG. 2C
myeloid vs whole human

| Codon | AA | Myeloid:Human | Codon | AA | Myeloid:Human |
|---|---|---|---|---|---|
| GCA | A | 1.10 | AAT | N | 0.91 |
| GCC | A | 0.88 | CCA | P | 1.12 |
| GCG | A | 0.66 | CCC | P | 1.17 |
| GCT | A | 1.20 | CCG | P | 0.80 |
| TGC | C | 1.23 | CCT | P | 0.77 |
| TGT | C | 0.72 | CAA | Q | 1.06 |
| GAC | D | 1.01 | CAG | Q | 0.98 |
| GAT | D | 0.99 | AGA | R | 1.02 |
| GAA | E | 1.04 | AGG | R | 1.28 |
| GAG | E | 0.97 | CGA | R | 0.83 |
| TTC | F | 1.14 | CGC | R | 0.76 |
| TTT | F | 0.84 | CGG | R | 0.89 |
| GGA | G | 0.96 | CGT | R | 1.25 |
| GGC | G | 1.10 | AGC | S | 1.17 |
| GGG | G | 1.04 | AGT | S | 0.94 |
| GGT | G | 0.80 | TCA | S | 1.13 |
| CAC | H | 1.05 | TCC | S | 1.01 |
| CAT | H | 0.93 | TCG | S | 0.74 |
| ATA | I | 0.83 | TCT | S | 0.80 |
| ATC | I | 1.28 | ACA | T | 0.95 |
| ATT | I | 0.72 | ACC | T | 1.18 |
| AAA | K | 0.85 | ACG | T | 0.88 |
| AAG | K | 1.11 | ACT | T | 0.85 |
| CTA | L | 0.98 | GTA | V | 0.77 |
| CTC | L | 1.23 | GTC | V | 1.22 |
| CTG | L | 1.09 | GTG | V | 1.01 |
| CTT | L | 0.76 | GTT | V | 0.88 |
| TTA | L | 0.65 | TGG | W | 1.00 |
| TTG | L | 0.93 | TAC | Y | 1.08 |
| ATG | M | 1.00 | TAT | Y | 0.90 |
| AAC | N | 1.08 | | | |

FIG. 3B

| Codon Table | Mean fold difference (WRT human) |
|---|---|
| Mouse genome | 0.046 |
| Liver | 0.150 |
| Myeloid | 0.135 |

\* $p < 1e\text{-}9$

FIG. 5

Human liver directed codon usage index (standard format)

| | | | | | | | | | | | |
|---|---|---|---|---|---|---|---|---|---|---|---|
| UUU | 0.35 | 321 | UCU | 0.17 | 217 | UAU | 0.37 | 204 | UGU | 0.4 | 187 |
| UUC | 0.65 | 589 | UCC | 0.28 | 364 | UAC | 0.63 | 353 | UGC | 0.6 | 276 |
| UUA | 0.04 | 70 | UCA | 0.13 | 166 | UAA | 0 | 0 | UGA | 1 | 100 |
| UUG | 0.11 | 216 | UCG | 0.06 | 78 | UAG | 0 | 0 | UGG | 1 | 285 |
| CUU | 0.1 | 199 | CCU | 0.28 | 343 | CAU | 0.41 | 252 | CGU | 0.07 | 73 |
| CUC | 0.23 | 462 | CCC | 0.38 | 463 | CAC | 0.59 | 367 | CGC | 0.24 | 246 |
| CUA | 0.06 | 120 | CCA | 0.24 | 297 | CAA | 0.25 | 204 | CGA | 0.1 | 103 |
| CUG | 0.47 | 967 | CCG | 0.1 | 128 | CAG | 0.75 | 613 | CGG | 0.21 | 213 |
| AUU | 0.28 | 216 | ACU | 0.19 | 208 | AAU | 0.41 | 284 | AGU | 0.12 | 160 |
| AUC | 0.61 | 466 | ACC | 0.47 | 502 | AAC | 0.59 | 416 | AGC | 0.25 | 326 |
| AUA | 0.11 | 84 | ACA | 0.24 | 229 | AAA | 0.35 | 358 | AGA | 0.18 | 189 |
| AUG | 1 | 383 | ACG | 0.12 | 129 | AAG | 0.65 | 654 | AGG | 0.2 | 206 |
| GUU | 0.13 | 163 | GCU | 0.27 | 368 | GAU | 0.39 | 374 | GGU | 0.12 | 163 |
| GUC | 0.26 | 333 | GCC | 0.44 | 585 | GAC | 0.61 | 578 | GGC | 0.37 | 495 |
| GUA | 0.08 | 106 | GCA | 0.19 | 251 | GAA | 0.35 | 419 | GGA | 0.23 | 306 |
| GUG | 0.52 | 659 | GCG | 0.1 | 139 | GAG | 0.65 | 786 | GGG | 0.28 | 378 |

FIG. 6

Sequence % Alignment

|  | Native (SEQ ID NO: 3) | Liver Optimized + CpGs (SEQ ID NO: 1) | Liver optimized − CpGs (SEQ ID NO: 2) |
|---|---|---|---|
| Native (SEQ ID NO: 3) | - | 69% | 72% |
| Liver Optimized + CpGs (SEQ ID NO: 1) | 69% | - | 92% |
| Liver Optimized − CpGs (SEQ ID NO: 2) | 72% | 92% | - |

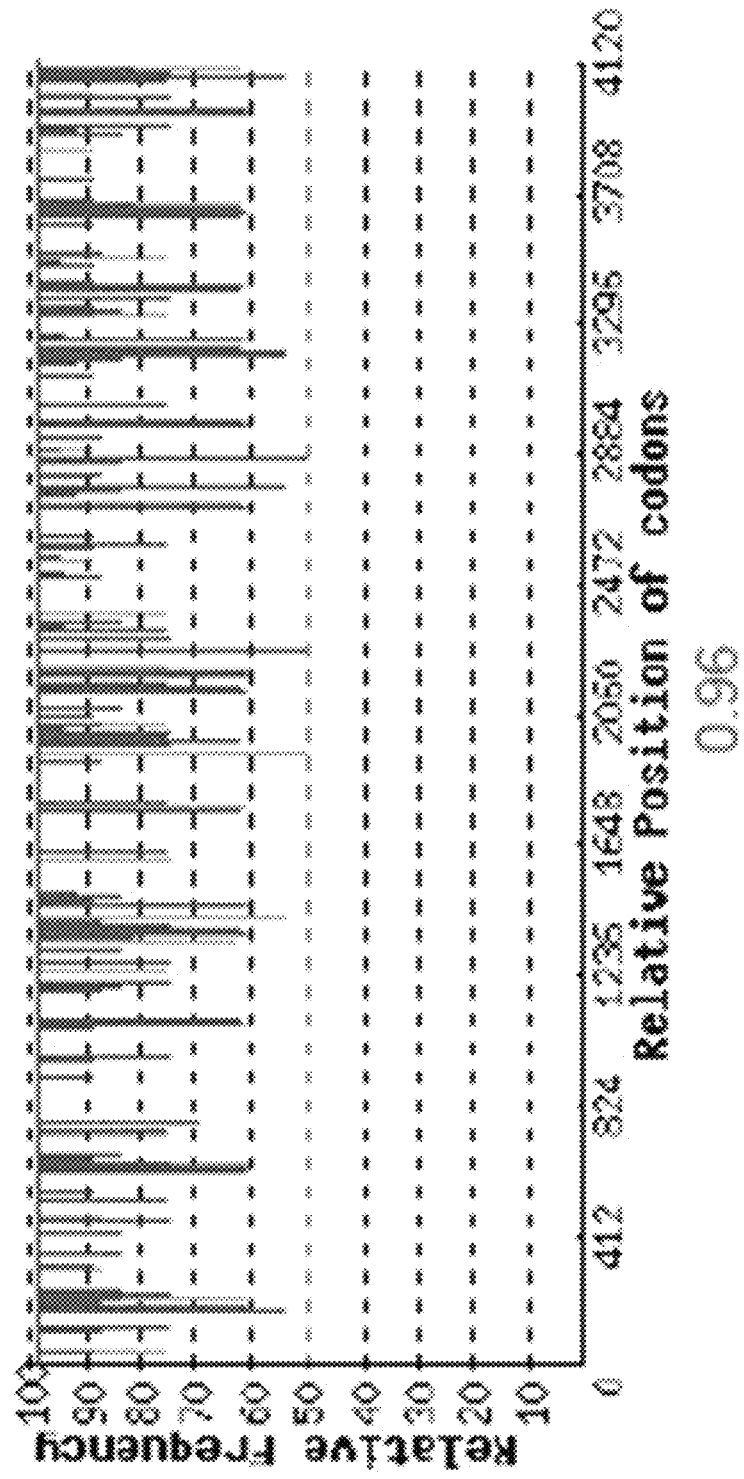

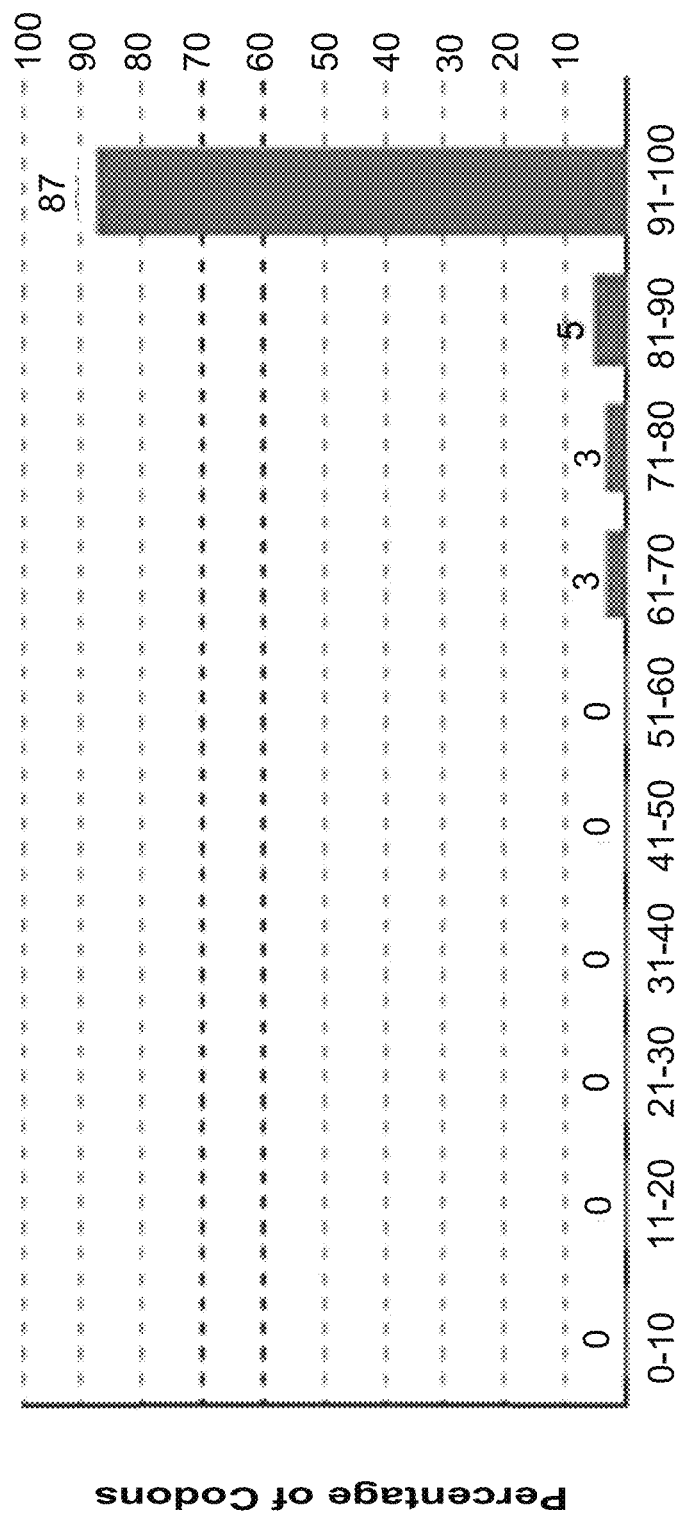

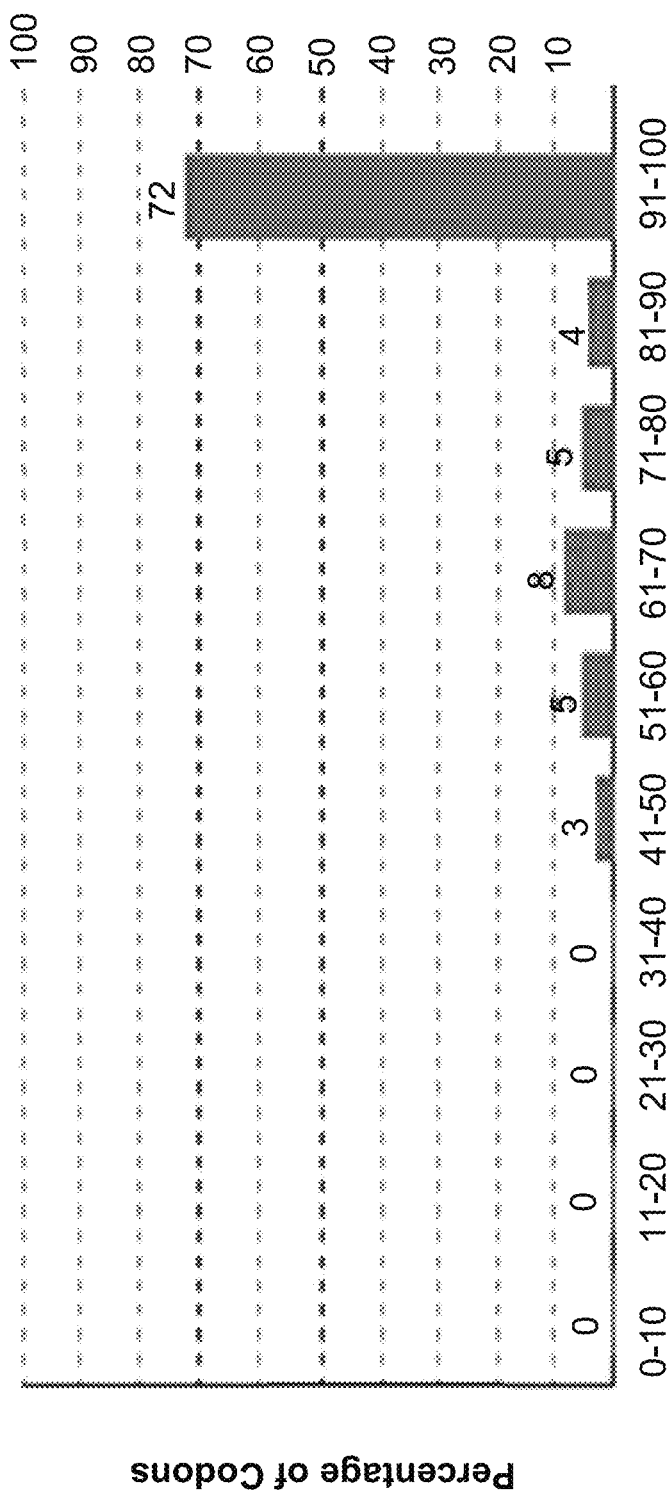

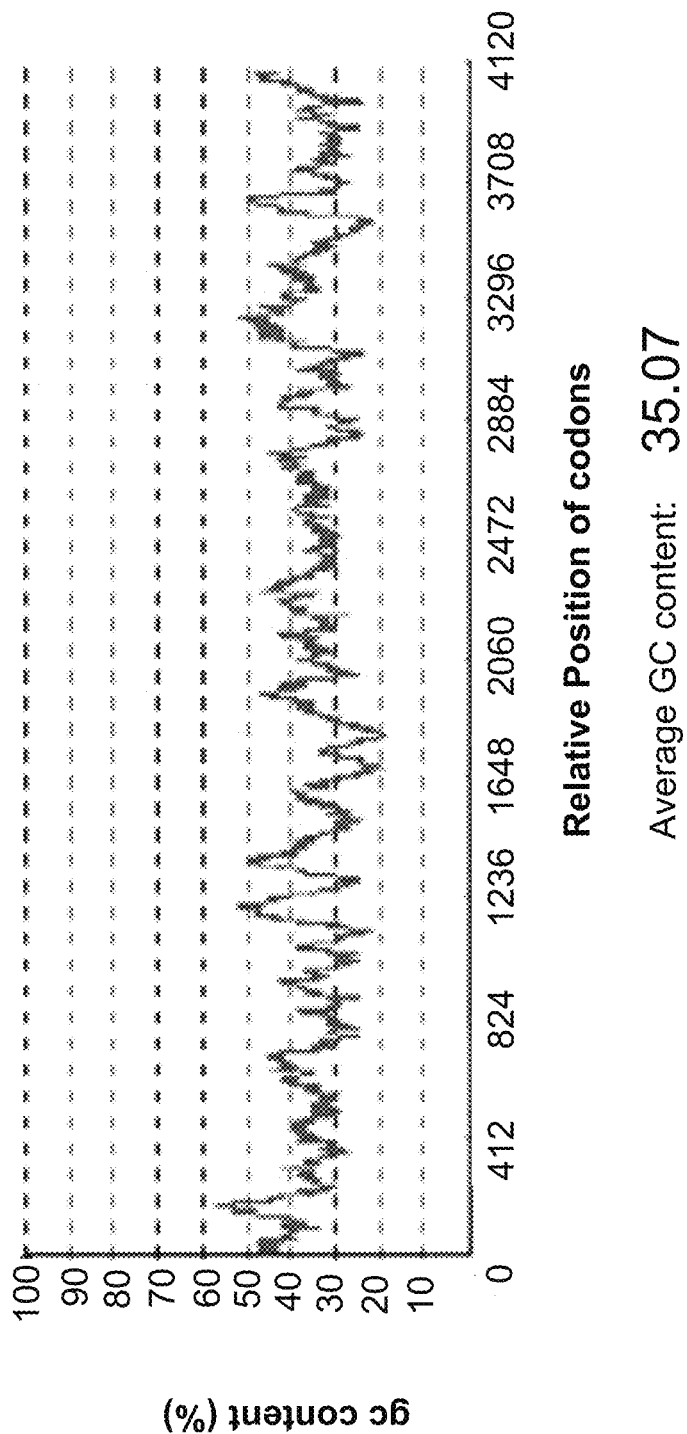
FIG. 9A Native sequence

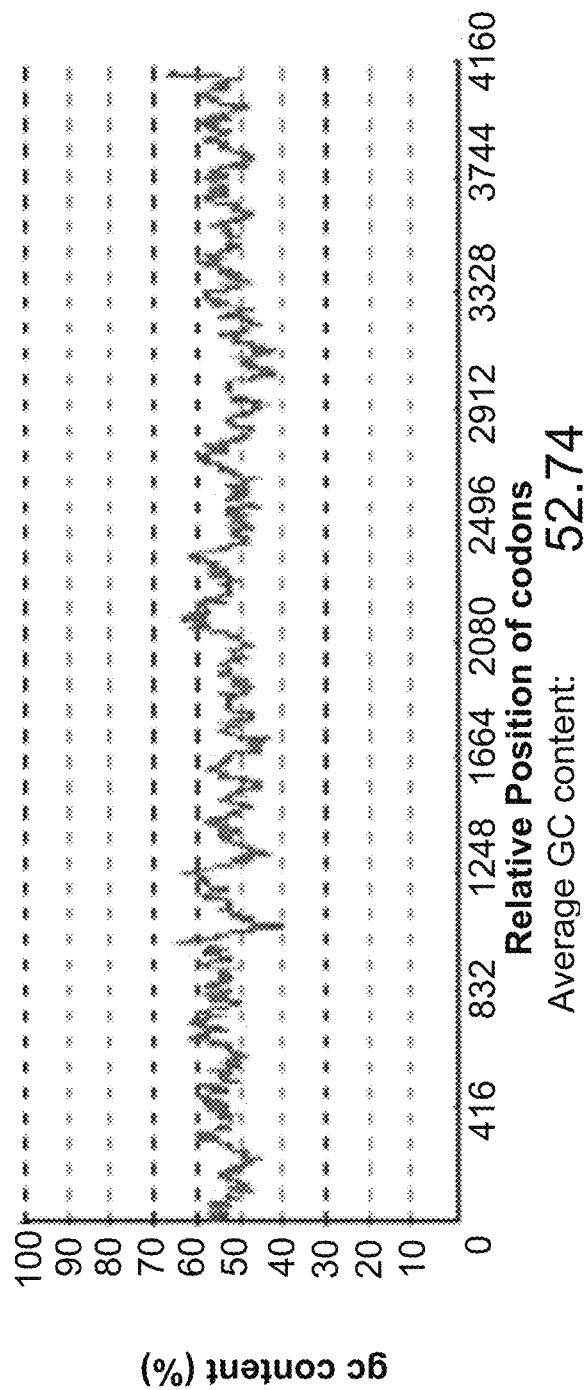

FIG. 10

| CIS-Acting Elements | Native (SEQ ID NO: 3) Original | Liver optimized (with CpGs) (SEQ ID No: 1) Optimized | Liver optimized (no CpGs) (SEQ ID NO: 2) Optimized |
|---|---|---|---|
| Splice(GGTAAG) | 0 | 0 | 0 |
| Splice(GGTGAT) | 3 | 0 | 0 |
| PolyA(AATAAA) | 0 | 0 | 0 |
| PolyA(ATTAAA) | 5 | 0 | 0 |
| Destabilizing(ATTTA) | 16 | 0 | 0 |
| PolyT(TTTTTT) | 7 | 0 | 0 |
| PolyA(AAAAAA) | 5 | 0 | 0 |
| Antiviral Motifs | Original | Optimized | Optimized |
| | 2 | 0 | 2 |

US 11,634,726 B2

SEQUENCE LISTING

<160> NUMBER OF SEQ ID NOS: 9

<210> SEQ ID NO 1
<211> LENGTH: 4128
<212> TYPE: DNA
<213> ORGANISM: Artificial Sequence
<220> FEATURE:
<223> OTHER INFORMATION: Recombinant Sequence

<400> SEQUENCE: 1

| | | | | | |
|---|---|---|---|---|---|
| atggacaaga | agtactccat | cggcctggac | atcgggacca | acagcgtggg | ctgggccgtg | 60 |
| atcaccgacg | agtacaaggt | gccctccaag | aagttcaagg | tgctggggaa | caccgacaga | 120 |
| cacagcatca | agaagaacct | gatcggcgcc | ctgctgttcg | actccggaga | aaccgctgag | 180 |
| gctacccgcc | tgaagagaac | cgctcgccgg | aggtacacca | gacgcaagaa | caggatctgc | 240 |
| tacctgcagg | agatcttctc | caacgagatg | gccaaggtgg | acgactcctt | cttccaccgg | 300 |
| ctggaggaga | gcttcctggt | ggaggaggac | aagaagcacg | agaggcaccc | catcttcggc | 360 |
| aacatcgtgg | acgaggtggc | ctaccacgag | aagtacccca | ccatctacca | cctgaggaag | 420 |
| aagctggtgg | actccaccga | caaggccgac | ctgagactgt | tctacctggc | cctggcccac | 480 |
| atgatcaagt | tccgcggcca | cttcctgatc | gagggggacc | tgaaccccga | caacagcgac | 540 |
| gtggacaagc | tgttcatcca | gctggtgcag | acctacaacc | agctgttcga | ggagaacccc | 600 |
| atcaacgctt | ccggagtgga | cgctaaggct | atcctgagcg | ccagactgtc | caagagccgg | 660 |
| aggctggaga | acctgatcgc | ccagctgccc | ggcgagaaga | agaacggcct | gttcgggaac | 720 |
| ctgatcgccc | tgtccctggg | gctgaccccc | aacttcaaga | gcaatttcga | cctggccgag | 780 |
| gacgccaagc | tgcagctgtc | caaggacacc | tacgacgacg | acctggacaa | cctgctggcc | 840 |
| cagatcggcg | accagtacgc | cgacctgttc | ctggccgcca | gaaacctgtc | cgacgccatc | 900 |
| ctgctgagcg | acatcctgcg | cgtgaacacc | gagatcacca | aggcccccct | gtccgccagc | 960 |
| atgatcaaga | gatacgacga | gcaccaccag | gacctgaccc | tgctgaaggc | cctggtgcgc | 1020 |
| cagcagctgc | ccgagaagta | caaggagatc | ttcttcgacc | agagcaagaa | cggatacgct | 1080 |
| ggatacatcg | acggaggagc | ctcccaggag | gagttctaca | agttcatcaa | gcccatcctg | 1140 |
| gagaagatgg | acggcaccga | ggagctgctg | gtgaagctga | accgggagga | cctgctgagg | 1200 |
| aagcagagaa | ccttcgacaa | cggctccatc | ccccaccaga | tccacctggg | ggagctgcac | 1260 |
| gccatcctga | cgccagga | ggacttctac | cccttcctga | aggacaacag | ggagaagatc | 1320 |
| gagaagatcc | tgaccttcag | aatcccatac | tacgtgggac | cactggctag | ggaaaactcc | 1380 |
| agattcgcct | ggatgacccg | gaagagcgag | gaaaccatca | cccccctgaa | cttcgaggag | 1440 |
| gtggtggaca | agggagcttc | cgcccagagc | ttcatcgaga | ggatgaccaa | cttcgacaag | 1500 |
| aacctgccca | acgagaaggt | gctgcccaag | cactccctgc | tgtacgagta | cttcaccgtg | 1560 |
| tacaacgagc | tgaccaaggt | gaagtacgtg | accgagggca | tgagaaagcc | cgccttcctg | 1620 |
| agcggggagc | agaagaaggc | catcgtggac | ctgctgttca | agaccaaccg | caaggtgacc | 1680 |
| gtgaagcagc | tgaaggagga | ctacttcaag | aagatcgagt | gcttcgactc | cgtggagatc | 1740 |
| agcggagtgg | aggaccgctt | caacgcttcc | ctggggacct | accacgacct | gctgaagatc | 1800 |
| atcaaggaca | aggacttcct | ggacaacgag | gagaacgagg | acatcctgga | ggacatcgtg | 1860 |
| ctgacccctga | ccctgttcga | ggaccgcgag | atgatcgagg | agcggctgaa | gacctacgcc | 1920 |
| cacctgttcg | acgacaaggt | catgaagcag | ctgaagcgga | ggagatacac | cggatggggg | 1980 |
| cgcctgagca | gaaagctgat | caacggcatc | cgggacaagc | agtccgggaa | gaccatcctg | 2040 |

```
gacttcctga agagcgacgg cttcgccaac aggaacttca tgcagctgat ccacgacgac    2100
tccctgacct tcaaggagga catccagaag gctcaggtgt ccggacaggg ggacagcctg    2160
cacgagcaca tcgctaacct ggctggcagc cccgccatca agaagggat cctgcagacc     2220
gtgaaggtgg tggacgagct ggtgaaggtc atgggcaggc acaagcccga gaacatcgtg    2280
atcgagatgg ccagagagaa ccagaccacc cagaaggggc agaagaactc ccgcgagcgg    2340
atgaagagga tcgaggaggg catcaaggag ctggggagcc agatcctgaa ggagcacccc    2400
gtggagaaca cccagctgca gaacgagaag ctgtacctgt actacctgca gaacggccgc    2460
gacatgtacg tggaccagga gctggacatc aaccggctgt ccgactacga cgtggaccac    2520
atcgtgcccc agtccttcct gaaggacgac agcatcgaca caaggtgct gacccgcagc     2580
gacaagaacc gggggaagtc cgacaacgtg cccagcgagg aggtggtgaa gaagatgaag    2640
aactactggc gccagctgct gaacgccaag ctgatcaccc agcgcaagtt cgacaacctg    2700
accaaggctg agagaggagg gctgtccgag ctggacaagg ccggcttcat caagaggcag    2760
ctggtggaaa ccagacagat caccaagcac gtggcccaga tcctggacag ccggatgaac    2820
accaagtacg acgagaacga caagctgatc agggaggtga aggtcatcac cctgaagtcc    2880
aagctggtga gcgacttccg caaggacttc cagttctaca aggtgcggga gatcaacaac    2940
taccaccacg cccacgacgc ttacctgaac gctgtggtgg gaaccgccct gatcaagaag    3000
taccccaagc tggagtccga gttcgtgtac ggggactaca aggtgtacga cgtgcgcaag    3060
atgatcgcca gtccgagca ggagatcggc aaggccaccg ccaagtactt cttctacagc     3120
aacatcatga acttcttcaa gaccgagatc accctggcca cggcgagat caggaagcgc    3180
cccctgatcg aaaccaacgg cgaaaccgga gagatcgtgt gggacaaggg aagagacttc    3240
gctaccgtgc ggaaggtgct gtccatgccc caggtgaaca tcgtgaagaa gaccgaggtg    3300
cagaccggcg ggttctccaa ggagagcatc ctgcccaaga ggaacagcga caagctgatc    3360
gccagaaaga aggactggga ccccaagaag tacgaggat cgactccccc aaccgtggct     3420
tacagcgtgc tggtggtggc caaggtggag aagggcaagt ccaagaagct gaagagcgtg    3480
aaggagctgc tggggatcac catcatggag cggtccagct cgagaagaa ccccatcgac     3540
ttcctggagg ccaagggcta caaggaggtg aagaaggacc tgatcatcaa gctgcccaag    3600
tacagcctgt tcgagctgga aaacggaaga agagaatgc tggcttccgc ggagagctg     3660
cagaagggaa acgagctggc cctgcccagc aagtacgtga acttcctgta cctggcctcc    3720
cactacgaga gctgaaggg cagccccgag gacaacgagc gaagcagct gttcgtggag     3780
cagcacaagc actacctgga cgagatcatc gagcagatct ccgagttcag caagcgcgtg    3840
atcctggccg acgccaacct ggacaaggtg ctgtccgcct acaacaagca cagggacaag    3900
cccatcagag agcaggccga gaacatcatc cacctgttca cctgaccaa cctgggagct     3960
ccagctgcct tcaagtactt cgacaccacc atcgacagga gagatacac cagcaccaag    4020
gaggtgctgg acgccaccct gatccaccag tccatcaccg gctgtacga accagaatc     4080
gacctgagcc agctgggagg cgaccccaag aagaagcgca aggtgtga              4128
```

<210> SEQ ID NO 2
<211> LENGTH: 4128
<212> TYPE: DNA
<213> ORGANISM: Artificial Sequence
<220> FEATURE:
<223> OTHER INFORMATION: Recombinant Sequence -continued

```
<400> SEQUENCE: 2
atggacaaga agtactccat tggcctggac attgggacca actctgtggg ctgggctgtg      60
atcacagatg agtacaaggt gccctccaag aagttcaagg tgctggggaa cacagacaga     120
cacagcatca agaagaacct gattggagcc ctgctgtttg actctggaga acagctgag      180
gctaccaggc tgaagagaac agctaggagg agatacacca gaagaaagaa caggatctgc     240
tacctgcagg agatcttctc caatgagatg gccaaggtgg atgactcctt cttccacagg     300
ctggaggaga gcttcctggt ggaggaggac aagaagcatg agaggcaccc catctttggc     360
aacattgtgg atgaggtggc ctaccatgag aagtacccca ccatctacca cctgaggaag     420
aagctggtgg actccacaga caaggctgac ctgagactga tctacctggc cctggcccac     480
atgatcaagt tcagaggcca cttcctgatt gaggggacc  tgaacccaga caactctgat     540
gtggacaagc tgttcatcca gctggtgcag acctacaacc agctgtttga ggagaacccc     600
atcaatgctt ctggagtgga tgctaaggct atcctgtctg ccagactgtc aagagcagg     660
aggctggaga acctgattgc ccagctgcct ggggagaaga gaatggcct  gtttgggaac     720
ctgattgccc tgtccctggg gctgacccc  aacttcaaga gcaattttga cctggctgag     780
gatgccaagc tgcagctgtc caaggacacc tatgatgatg acctggacaa cctgctggcc     840
cagattggag accagtatgc tgacctgttc ctggctgcta agaacctgtc tgatgccatc     900
ctgctgtctg acatcctgag ggtgaacaca gagatcacca ggcccccct  gtctgccagc     960
atgatcaaga gatatgatga gcaccaccag gacctgaccc tgctgaaggc cctggtgagg    1020
cagcagctgc ctgagaagta caaggagatc ttctttgacc agagcaagaa tggatatgct    1080
ggatacattg atggaggagc ctcccaggag gagttctaca gttcatcaa  gcccatcctg    1140
gagaagatga atggcacaga ggagctgctg gtgaagctga acaggagga  cctgctgagg    1200
aagcagagaa cctttgacaa tggctccatc ccccaccaga tccacctggg ggagctgcat    1260
gccatcctga gaagacagga ggacttctac cccttcctga aggacaacag ggagaagatt    1320
gagaagatcc tgaccttcag aatcccatac tatgtgggac cactggctag gggaaactcc    1380
agatttgcct ggatgaccag gaagtctgag gaaaccatca ccccctggaa ctttgaggag    1440
gtggtggaca agggagcttc tgcccagagc ttcattgaga ggatgaccaa ctttgacaag    1500
aacctgccca tgagaaggt  gctgcccaag cactccctgc tgtatgagta cttcacagtg    1560
tacaatgagc tgaccaaggt gaagtatgtg acagagggca tgagaaagcc tgccttcctg    1620
tctggggagc agaagaaggc cattgtggac ctgctgttca agaccaacag gaaggtgaca    1680
gtgaagcagc tgaaggagga ctacttcaag aagattgagt gctttgactc tgtggagatc    1740
tctggagtgg aggacagatt caatgcttcc ctggggacct accatgacct gctgaagatc    1800
atcaaggaca aggacttcct ggacaatgag gagaatgagg acatcctgga ggacattgtg    1860
ctgacccctga ccctgtttga ggacagagag atgattgagg agaggctgaa gacctatgcc    1920
cacctgtttg atgacaaggt catgaagcag ctgaagagga ggagatacac aggatggggg    1980
aggctgagca gaaagctgat caatggcatc agagacaagc agtctgggaa gaccatcctg    2040
gacttcctga agtctgatgg ctttgccaac aggaacttca tgcagctgat ccatgatgac    2100
tccctgacct tcaaggagga catccagaag gctcaggtgt ctggacaggg ggacagcctg    2160
catgagcaca ttgctaacct ggctggcagc cctgccatca gaagggggat cctgcagact    2220
gtgaaggtgt ggatgagct  ggtgaaggtc atggcaggc  acaagcctga gaacattgtg    2280
attgagatgg ccagagagaa ccagaccacc cagaaggggc agaagaactc cagagagagg    2340
```

```
atgaagagga ttgaggaggg catcaaggag ctggggagcc agatcctgaa ggagcaccct    2400
gtggagaaca cccagctgca gaatgagaag ctgtacctgt actacctgca gaatggcaga    2460
gacatgtatg tggaccagga gctggacatc aacagactgt ctgactatga tgtggaccac    2520
attgtgcccc agtccttcct gaaggatgac agcattgaca caaggtgct gaccagatct     2580 gacaagaata gggggaagtc tgacaatgtg ccctctgagg aggtggtgaa aagatgaag     2640 aactactgga gacagctgct gaatgccaag ctgatcaccc agagaaagtt tgacaacctg    2700
accaaggctg agaggagg gctgtctgag ctggacaagg ctggcttcat caagaggcag      2760
ctggtggaaa ccagacagat caccaagcat gtggcccaga tcctggacag caggatgaac    2820
accaagtatg atgagaatga caagctgatc agggaggtga aggtcatcac cctgaagtcc    2880
aagctggtgt ctgacttcag aaaggacttc cagttctaca aggtgagaga gatcaacaac    2940
taccaccatg cccatgatgc ttacctgaat gctgtggtgg aacagccct gatcaagaag     3000 taccccaagc tggagtctga gtttgtgtat gggactaca aggtgtatga tgtgagaaag     3060
atgattgcca agtctgagca ggagattggc aaggccacag ccaagtactt cttctacagc    3120
aacatcatga acttcttcaa gacagagatc accctggcca tggggagat caggaagaga     3180 cccctgattg aaaccaatgg ggaaactgga gagattgtgt gggacaaggg aagagacttt    3240
gctacagtga aaaggtgct gtccatgccc caggtgaaca ttgtgaagaa gacagaggtg     3300
cagacagggg ggttctccaa ggagagcatc ctgcccaaga ggaactctga caagctgatt    3360
gccagaaaga aggactggga ccccaagaag tatggaggat ttgactcccc aacagtgget   3420 tactctgtgc tggtggtggc caaggtggag aagggcaagt ccaagaagct gaagtctgtg    3480
aaggagctgc tggggatcac catcatggag agatccagct tgagaagaa cccccattgac    3540 ttcctggagg ccaagggcta aaggaggtg aagaaggacc tgatcatcaa gctgcccaag     3600
tacagcctgt ttgagctgga aatggaaga aagagaatgc tggcttctgc tggagagctg     3660
cagaagggaa atgagctggc cctgcccagc aagtatgtga acttcctgta cctggcctcc    3720
cactatgaga agctgaaggg cagccctgag gacaatgagc agaagcagct gtttgtggag    3780
cagcacaagc actacctgga tgagatcatt gagcagatct ctgagttcag caagagagtg    3840
atcctggctg atgccaacct ggacaaggtg ctgtctgcct acaacaagca cagggacaag    3900
cccatcagag agcaggctga aacatcatcc acctgttca ccctgaccaa cctgggagct     3960
ccagctgcct tcaagtactt tgacaccacc attgacagga gagatacac cagcaccaag    4020 gaggtgctgg atgccaccct gatccaccag tccatcacag gctgtatga aaccagaatt     4080 gacctgagcc agctgggagg agaccccaag aagaagagaa aggtgtga                 4128
```

<210> SEQ ID NO 3  
<211> LENGTH: 4140  
<212> TYPE: DNA  
<213> ORGANISM: Streptococcus pyogenes

<400> SEQUENCE: 3

```
atggacaaga agtactccat tgggctcgat atcggcacaa acagcgtcgg ctgggccgtc     60
attacggacg agtacaaggt gccgagcaaa aaattcaaag ttctgggcaa taccgatcgc    120
cacagcataa agaagaacct cattggcgcc ctcctgttcg actccgggga gacggccgaa    180
gccacgcggc tcaaaagaac agcacggcgc agatataccc gcagaaagaa tcggatctgc    240
tacctgcagg agatctttag taatgagatg gctaaggtgg atgactcttt cttccatagg    300
```

```
ctggaggagt cctttttggt ggaggaggat aaaaagcacg agcgccaccc aatctttggc      360
aatatcgtgg acgaggtggc gtaccatgaa aagtacccaa ccatatatca tctgaggaag      420
aagcttgtag acagtactga taaggctgac ttgcggttga tctatctcgc gctggcgcat      480
atgatcaaat ttcggggaca cttcctcatc gagggggacc tgaacccaga caacagcgat      540
gtcgacaaac tctttatcca actggttcag acttacaatc agcttttcga agagaacccg      600
atcaacgcat ccgagttga cgccaaagca atcctgagcg ctaggctgtc caaatcccgg      660
cggctcgaaa acctcatcgc acagctccct ggggagaaga gaacggcct gtttggtaat      720 cttatcgccc tgtcactcgg gctgaccccc aactttaaat ctaacttcga cctggccgaa      780
gatgccaagc ttcaactgag caaagacacc tacgatgatg atctcgacaa tctgctggcc      840
cagatcggcg accagtacgc agacctttt ttggcggcaa agaacctgtc agacgccatt      900
ctgctgagtg atattctgcg agtgaacacg gagatcacca agctccgct gagcgctagt      960 atgatcaagc gctatgatga gcaccaccaa gacttgactt tgctgaaggc ccttgtcaga     1020
cagcaactgc ctgagaagta caaggaaatt ttcttcgatc agtctaaaaa tggctacgcc     1080
ggatacattg acggcggagc aagccaggag gaattttaca aatttattaa gcccatcttg     1140
gaaaaaatgg acggcaccga ggagctgctg gtaaagctta acagagaaga tctgttgcgc     1200
aaacagcgca ctttcgacaa tggaagcatc ccccaccaga ttcacctggg cgaactgcac     1260
gctatcctca ggcggcaaga ggatttctac ccctttttga agataacag ggaaaagatt      1320 gagaaaatcc tcacatttcg gataccctac tatgtaggcc ccctcgcccg gggaaattcc     1380
agattcgcgt ggatgactcg caaatcagaa gagaccatca ctccctggaa cttcgaggaa     1440
gtcgtggata aggggcctc tgcccagtcc ttcatcgaaa ggatgactaa ctttgataaa     1500
aatctgccta cgaaaaggt gcttcctaaa cactctctgc tgtacgagta cttcacagtt     1560
tataacgagc tcaccaaggt caaatacgtc acagaaggga tgagaaagcc agcattcctg     1620
tctggagagc agaagaaagc tatcgtggac ctcctcttca agacgaaccg gaaagttacc     1680
gtgaaacagc tcaaagaaga ctatttcaaa aagattgaat gtttcgactc tgttgaaatc     1740
agcggagtgg aggatcgctt caacgcatcc ctgggaacgt atcacgatct cctgaaaatc     1800
attaaagaca aggacttcct ggacaatgag gagaacgagg acattcttga ggacattgtc     1860
ctcaccctta cgttgtttga agataggag atgattgaag aacgcttgaa aacttacgct     1920
catctcttcg acgacaaagt catgaaacag ctcaagaggc gccgatatac aggatggggg     1980
cggctgtcaa gaaaactgat caatgggatc cgagacaagc agagtggaaa gacaatcctg     2040
gattttctta agtccgatgg atttgccaac cggaacttca tgcagttgat ccatgatgac     2100
tctctcacct ttaaggagga catccagaaa gcacaagttt ctggccaggg ggacagtctt     2160
cacgagcaca tcgctaatct tgcaggtagc ccagctatca aaaagggaat actgcagacc     2220
gttaaggtcg tggatgaact cgtcaaagta atgggaaggc ataagcccga gaatatcgtt     2280
atcgagatgg cccgagagaa ccaaactacc cagaagggac agaagaacag tagggaaagg     2340
atgaagagga ttgaagaggg tataaaagaa ctggggtccc aaatccttaa ggaacaccca     2400
gttgaaaaca cccagcttca gaatgagaag ctctacctgt actacctgca gaacggcagg     2460
gacatgtacg tggatcagga actggacatc aatcggctct ccgactacga cgtggatcat     2520
atcgtgcccc agtctttct caaagatgat tctattgata taaagtgtt gacaagatcc     2580 gataaaaata gagggaagag tgataacgtc ccctcagaag aagttgtcaa gaaaatgaaa     2640
aattattggc ggcagctgct gaacgccaaa ctgatcacac aacggaagtt cgataatctg     2700
```

```
actaaggctg aacgaggtgg cctgtctgag ttggataaag ccggcttcat caaaaggcag    2760
cttgttgaga cacgccagat caccaagcac gtggcccaaa ttctcgattc acgcatgaac    2820
accaagtacg atgaaaatga caaactgatt cgagaggtga agttattac tctgaagtct     2880 aagctggtct cagatttcag aaaggacttt cagttttata aggtgagaga gatcaacaat    2940
taccaccatg cgcatgatgc ctacctgaat gcagtggtag gcactgcact tatcaaaaaa    3000
tatcccaagc ttgaatctga atttgtttac ggagactata agtgtacga tgttaggaaa    3060 atgatcgcaa agtctgagca ggaaataggc aaggccaccg ctaagtactt cttttacagc    3120
aatattatga atttttttcaa gaccgagatt acactggcca atggagagat cggaagcga    3180 ccacttatcg aaacaaacgg agaaacagga gaaatcgtgt gggacaaggg tagggatttc    3240
gcgacagtcc ggaaggtcct gtccatgccg caggtgaaca tcgttaaaaa gaccgaagta    3300
cagaccggag gcttctccaa ggaaagtatc ctcccgaaaa ggaacagcga caagctgatc    3360
gcacgcaaaa aagattggga ccccaagaaa tacggcggat tcgattctcc tacagtcgct    3420
tacagtgtac tggttgtggc caaagtggag aaagggaagt ctaaaaaact caaaagcgtc    3480
aaggaactgc tgggcatcac aatcatggag cgatcaagct tcgaaaaaaa ccccatcgac    3540
tttctcgagg cgaaaggata taagaggtc aaaaaagacc tcatcattaa gcttcccaag     3600
tactctctct ttgagcttga aaacggccgg aaacgaatgc tcgctagtgc gggcgagctg    3660
cagaaaggta acgagctggc actgccctct aaatacgtta atttcttgta tctggccagc    3720
cactatgaaa agctcaaagg gtctcccgaa gataatgagc agaagcagct gttcgtggaa    3780
caacacaaac actaccttga tgagatcatc gagcaaataa gcgaattctc caaaagagtg    3840
atcctcgccg acgctaacct cgataaggtg ctttctgctt acaataagca cagggataag    3900
cccatcaggg agcaggcaga aaacattatc cacttgttta ctctgaccaa cttgggcgcg    3960
cctgcagcct tcaagtactt cgacaccacc atagacagaa agcggtacac ctctacaaag    4020
gaggtcctgg acgccacact gattcatcag tcaattacgg ggctctatga aacaagaatc    4080
gacctctctc agctcggtgg agacagcagg gctgacccca agaagaagag gaaggtgtga    4140
```

<210> SEQ ID NO 4  
<211> LENGTH: 4128  
<212> TYPE: DNA  
<213> ORGANISM: Artificial Sequence  
<220> FEATURE:  
<223> OTHER INFORMATION: Recombinant Sequence

<400> SEQUENCE: 4

```
atggacaaga agtattctat tggcctggat attggcacaa attctgtggg ctgggctgtg      60
atcacagatg agtacaaggt gccatctaag aagtttaagg tgctgggcaa cacagatagg     120
cacagcatca agaagaatct gattggagcc ctgctgtttg actctggaga cacagcagag     180
gcaacaagac tgaagagaac agccagaaga aggtatacaa gaggaagaa taggatctgc     240 tacctgcagg agatcttcag caatgagatg gccaaggtgg atgattcctt cttcacaga     300 ctggaggagt ctttcctggt ggaggaggat aagaagcatg agaggcaccc catctttggc     360
aacattgtga tgaggtggc ctatcatgag aagtacccta atctatca cctgaggaag       420 aagctggtgg acagcacaga taaggctgac ctgagactga tctatctggc cctggcccac    480
atgatcaagt tcagaggcca ctttctgatt gaggagatc tgaacccaga caattctgat    540
gtggacaagc tgttcatcca gctggtgcag acctacaatc agctgtttga ggagaacccc   600
```

```
atcaatgcat ctggagtgga tgcaaaggca atcctgtctg ccagactgtc taagagcaga    660
aggctggaga acctgattgc ccagctgcca ggagagaaga agaatggcct gtttggcaat    720
ctgattgccc tgagcctggg cctgacaccc aacttcaagt ccaattttga tctggcagag    780
gatgccaagc tgcagctgag caaggacacc tatgatgatg acctggataa cctgctggcc    840
cagattgggg atcagtatgc tgacctgttc ctggctgcca agaatctgtc tgatgccatc    900
ctgctgtctg atatcctgag agtgaacaca gagatcacaa aggccccct gtctgcctct    960 atgatcaaga ggtatgatga gcaccaccag gatctgaccc tgctgaaggc cctggtgaga   1020
cagcagctgc tgagaagta caaggagatc ttctttgatc agtctaagaa tggatatgca   1080
ggatatattg atggaggagc aagccaggag gagttctaca agtttatcaa gcccatcctg   1140
gagaagatgg atggcacaga ggagctgctg gtgaagctga atagggagga cctgctgagg   1200
aagcagagaa cctttgataa tggctccatc cctcaccaga tccacctggg agagctgcat   1260
gcaatcctga ggaggcagga ggacttctac ccatttctga aggataacag ggagaagatt   1320
gagaagatcc tgacatttag aatcccctac tatgtgggcc ctctggccag ggcaattct   1380 aggtttgcct ggatgaccag aaagtctgag gagacaatca caccctggaa ctttgaggag   1440
gtggtggata agggagcctc tgcccagtcc ttcattgaga ggatgacaaa ttttgacaag   1500
aacctgccaa atgagaaggt gctgcccaag cactctctgc tgtatgagta tttcacagtg   1560
tataatgagc tgacaaaggt gaagtatgtg acagagggca tgagaaagcc tgccttcctg   1620
tctggagagc agaagaaggc cattgtggac ctgctgttta agaccaatag gaaggtgaca   1680
gtgaagcagc tgaaggagga ctatttcaag aagattgagt gttttgattc tgtggagatc   1740
tctggagtgg aggacagatt caatgcaagc ctgggcacct accatgatct gctgaagatc   1800
atcaaggata aggacttcct ggacaatgag gagaatgagg atatcctgga ggacattgtg   1860
ctgaccctga cactgtttga ggatagggag atgattgagg agagactgaa gacatatgcc   1920
cacctgtttg atgacaaagt gatgaagcag ctgaagagaa ggagatacac tggatggggc   1980
aggctgtcca gaaagctgat caatggcatc agagacaagc agtctggcaa gacaatcctg   2040
gactttctga gtctgatgg ctttgccaac aggaacttca tgcagctgat ccatgatgac   2100
tccctgacct tcaaggagga tatccagaag gcacaggtgt ctggacaggg agactctctg   2160
catgagcaca ttgccaacct ggctggctct cctgccatca agaagggcat cctgcagaca   2220
gtgaaggtgg tggatgagct ggtgaaagtg atgggcaggc acaagccaga gaacattgtg   2280
attgagatgg ccagagagaa tcagaccaca cagaagggcc agaagaacag cagggagaga   2340
atgaagagaa ttgaggaggg catcaaggag ctgggctccc agatcctgaa ggagcaccct   2400
gtggagaaca cacagctgca gaatgagaag ctgtatctgt actatctgca gaatggcaga   2460
gatatgtatg tggaccagga gctggatatc aacagactgt ctgattatga tgtggatcac   2520
attgtgccac agagcttcct gaaggatgac tccattgaca ataaggtgct gaccaggtct   2580
gacaagaaca gaggcaagtc tgataatgtg ccctcagagg aggtggtgaa gaagatgaag   2640
aactactgga ggcagctgct gaatgccaag ctgatcacac agaggaagtt tgataacctg   2700
accaaggcag agagaggagg cctgtctgag ctggacaagg caggcttcat caagaggcag   2760
ctggtggaga caagacagat cacaaagcat gtggcccaga tcctggattc tagaatgaac   2820
acaaagtatg atgagaatga caagctgatc agggaggtga aagtgatcac cctgaagtct   2880
aagctggtgt cagactttag gaaggatttc cagtttttata aggtgagaga gatcaacaac   2940
taccaccatg cccatgatgc ctacctgaat gctgtggtgg gcacagccct gatcaagaag   3000
```

| | | |
|---|---|---|
| tacccctaagc tggagtctga gtttgtgtat ggagactata aggtgtatga tgtgaggaag | 3060 |
| atgattgcca agtctgagca ggagattggc aaggccacag ccaagtattt cttttactct | 3120 |
| aacatcatga atttctttaa gacagagatc acactggcca atggagagat caggaagaga | 3180 |
| ccactgattg agacaaatgg agagacagga gagattgtgt gggacaaggg cagagatttt | 3240 |
| gccacagtga gaaaggtgct gagcatgccc caagtgaata ttgtgaagaa gactgaggtg | 3300 |
| cagacaggag gcttctctaa ggagagcatc ctgcctaaga ggaactctga taagctgatt | 3360 |
| gccagaaaga aggactggga tcctaagaag tatggaggct ttgactctcc aacagtggcc | 3420 |
| tactcagtgc tggtggtggc caaggtggag aagggcaagt ctaagaagct gaagtctgtg | 3480 |
| aaggagctgc tgggcatcac catcatggag agaagctcct tgagaagaa tcctattgat | 3540 |
| tttctggagg ccaagggcta taaggagtg aagaaggacc tgatcatcaa gctgccaaag | 3600 |
| tactccctgt ttgagctgga gaatggcagg aagagaatgc tggcatctgc tggagagctg | 3660 |
| cagaagggca atgagctggc cctgcccagc aagtatgtga acttcctgta tctggcctcc | 3720 |
| cactatgaga agctgaaggg ctcccctgag gataatgagc agaagcagct gtttgtggag | 3780 |
| cagcacaagc actatctgga tgagatcatt gagcagatct cagagttctc taagagagtg | 3840 |
| atcctggctg atgccaatct ggataaggtg ctgagtgcct acaacaagca cagggataag | 3900 |
| ccaatcagag agcaggcaga gaatatcatc cacctgttca ccctgacaaa cctgggagca | 3960 |
| ccagcagcct tcaagtattt tgacaccaca attgatagga gaggtacac ctccacaaag | 4020 |
| gaggtgctgg atgccaccct gatccaccag agcatcacag gctgtatga gacaaggatt | 4080 |
| gacctgtccc agctgggagg agaccccaag aagaagagga aggtgtga | 4128 |

<210> SEQ ID NO 5
<211> LENGTH: 4128
<212> TYPE: DNA
<213> ORGANISM: Artificial Sequence
<220> FEATURE:
<223> OTHER INFORMATION: Recombinant Sequence

<400> SEQUENCE: 5

| | | |
|---|---|---|
| atggacaaga agtattctat cggcctggat atcggcacaa atagcgtggg ctgggccgtg | 60 |
| atcaccgacg agtacaaggt gccatctaag aagtttaagg tgctgggcaa caccgatcgc | 120 |
| cacagcatca gaagaatct gatcggcgcc ctgctgttcg actccggaga gacagcagag | 180 |
| gcaacacggc tgaagagaac cgcccggaga aggtatacac gccggaagaa tcggatctgc | 240 |
| tacctgcagg agatcttcag caacgagatg gccaaggtgg acgattcctt ctttcacaga | 300 |
| ctggaggagt cttttcctgg tggaggagat aagaagcacg agaggcaccc catctttggc | 360 |
| aacatcgtgg acgaggtggc ctatcacgag aagtacccta caatctatca cctgaggaag | 420 |
| aagctggtgg acagcaccga taaggccgac ctgcgcctga tctatctggc cctggcccac | 480 |
| atgatcaagt tccggggcca ctttctgatc gagggcgatc tgaacccaga caattccgat | 540 |
| gtggacaagc tgttcatcca gctggtgcag acctacaatc agctgtttga ggagaacccc | 600 |
| atcaatgcat ccggagtgga cgcaaaggca atcctgtctg ccagactgtc taagagcaga | 660 |
| aggctggaga acctgatcgc ccagctgcca ggcgagaaga gaacggcct gtttggcaat | 720 |
| ctgatcgccc tgagcctggg cctgacaccc aacttcaagt ccaattttga tctggccgag | 780 |
| gacgccaagc tgcagctgag caaggacacc tatgacgatg acctggataa cctgctggcc | 840 |
| cagatcggcg atcagtacgc cgacctgttc ctggccgcca gaatctgtc cgacgccatc | 900 |

```
ctgctgtctg atatcctgag agtgaacacc gagatcacaa aggcccccct gtccgcctct    960
atgatcaagc ggtacgacga gcaccaccag gatctgaccc tgctgaaggc cctggtgcgg   1020
cagcagctgc ctgagaagta caaggagatc ttctttgatc agtctaagaa tggatacgca   1080
ggatatatcg acggaggagc aagccaggag gagttctaca agtttatcaa gcccatcctg   1140
gagaagatgg acggcacaga ggagctgctg gtgaagctga atagggagga cctgctgagg   1200
aagcagcgca cctttgataa cggctccatc cctcaccaga tccacctggg agagctgcac   1260
gcaatcctgc gccggcagga ggacttctac ccatttctga aggataacag ggagaagatc   1320
gagaagatcc tgacattccg catccsctac tatgtgggcc ctctggccag ggcaattct   1380
```

```
cagacaggcg gcttctctaa ggagagcatc ctgcctaaga ggaactccga taagctgatc    3360
gcccgcaaga aggactggga tcctaagaag tatggcggct tcgactctcc aacagtggcc    3420
tacagcgtgc tggtggtggc caaggtggag aagggcaagt ctaagaagct gaagagcgtg    3480
aaggagctgc tgggcatcac catcatggag agaagctcct tcgagaagaa tcctatcgat    3540
tttctggagg ccaagggcta taaggaggtg aagaaggacc tgatcatcaa gctgccaaag    3600
tactccctgt ttgagctgga gaacggccgg aagagaatgc tggcatctgc cggagagctg    3660
cagaagggca atgagctggc cctgcccagc aagtacgtga acttcctgta tctggcctcc    3720
cactacgaga agctgaaggg ctcccctgag gataacgagc agaagcagct gtttgtggag    3780
cagcacaagc actatctgga cgagatcatc gagcagatct ccgagttctc taagagagtg    3840
atcctggccg acgccaatct ggataaggtg ctgagcgcct acaacaagca cagggataag    3900
ccaatccgcg agcaggccga gaatatcatc cacctgttca ccctgacaaa cctgggagca    3960
ccagcagcct tcaagtattt tgacaccaca atcgatagga gcggtacac ctccacaaag    4020
```

```
cagacaggcg gcttctctaa ggagagcatc ctgcctaaga ggaactccga taagctgatc    3360
gcccgcaaga aggactggga tcctaagaag tatggcggct tcgactctcc aacagtggcc    3420
tacagcgtgc tggtggtggc caaggtggag aagggcaagt ctaagaagct gaagagcgtg    3480
aaggagctgc tgggcatcac catcatggag agaagctcct tcgagaagaa tcctatcgat    3540
tttctggagg ccaagggcta taaggaggtg aagaaggacc tgatcatcaa gctgccaaag    3600
tactccctgt ttgagctgga gaacggccgg aagagaatgc tggcatctgc cggagagctg    3660
cagaagggca atgagctggc cctgcccagc aagtacgtga acttcctgta tctggcctcc    3720
cactacgaga agctgaaggg ctcccctgag gataacgagc agaagcagct gtttgtggag    3780
cagcacaagc actatctgga cgagatcatc gagcagatct ccgagttctc taagagagtg    3840
atcctggccg acgccaatct ggataaggtg ctgagcgcct acaacaagca cagggataag    3900
ccaatccgcg agcaggccga gaatatcatc cacctgttca ccctgacaaa cctgggagca    3960
ccagcagcct tcaagtattt tgacaccaca atcgatagga gcggtacac ctccacaaag    4020 gaggtgctgg acgccaccct gatccaccag agcatcaccg cctgtacga gacaaggatc    4080 gacctgtccc agctgggagg cgaccccaag aagaagcgga aggtgtga                4128
```

<210> SEQ ID NO 6
<211> LENGTH: 4128
<212> TYPE: DNA
<213> ORGANISM: Artificial Sequence
<220> FEATURE:
<223> OTHER INFORMATION: Recombinant Sequence

<400> SEQUENCE: 6

```
atggacaaga agtattctat tggcctggat attggcacaa attctgtggg ctgggctgtg      60
atcacagatg agtacaaggt ggcatctaag aagtttaagg tgctgggcaa cacagatagg     120
cacagcatca agaagaatct gattggagcc ctgctgtttg actctggaga gacagcagag     180
gcaacaagac tgaagagaac agccagaaga aggtatacaa gaaggaagaa taggatctgc     240
tacctgcagg agatcttcag caatgagatg gccaaggtgg atgattcctt ctttcacaga     300
ctggaggagt ctttcctggt ggaggaggat aagaagcatg agaggcaccc catctttggc     360
aacattgtgg atgaggtggc ctatcatgag aagtacccta caatctatca cctgaggaag     420
aagctggtga cagcacagag gaaggctgac ctgagactga tctatctggc cctggcccac     480
atgatcaagt tcagaggcca ctttctgatt gagggagatc tgaacccaga caattctgat     540
gtggacaagc tgttcatcca gctggtgcag acctacaatc agctgtttga ggagaacccc     600
atcaatgcat ctggagtgga tgcaaaggca atcctgtctg ccagactgtc taagagcaga     660
aggctggaga acctgattgc ccagctgcca ggagagaaga gaatggcct gtttggcaat     720 ctgattgccc tgagcctggg cctgacaccc aacttcaagt ccaattttga tctggcagag     780
gatgccaagc tgcagctgag caaggacacc tatgatgatg acctggataa cctgctggcc     840
cagattgggg atcagtatgc tgacctgttc ctggctgcca gaatctgtc tgatgccatc     900 ctgctgtctg atatcctgag agtgaacaca gagatcacaa aggcccccct gtctgcctct     960
atgatcaaga ggtatgatga gcaccaccag gatctgaccc tgctgaaggc cctggtgaga    1020
cagcagctgc tgagaagtta caaggagatc ttctttgatc agtctaagaa tggatatgca    1080
ggatatattg atgagggagc aagccaggag gagttctaca agtttatcaa gcccatcctg    1140
gagaagatgg atggcacaga ggagctgctg gtgaagctga ataggagga cctgctgagg    1200
```

```
aagcagagaa cctttgataa tggctccatc cctcaccaga tccacctggg agagctgcat    1260
gcaatcctga ggaggcagga ggacttctac ccatttctga aggataacag ggagaagatt    1320
gagaagatcc tgacatttag aatcccctac tatgtgggcc ctctggccag gggcaattct    1380
aggtttgcct ggatgaccag aaagtctgag gagacaatca caccctggaa ctttgaggag    1440
gtggtggata agggagcctc tgcccagtcc ttcattgaga ggatgacaaa ttttgacaag    1500
aacctgccaa atgagaaggt gctgcccaag cactctctgc tgtatgagta tttcacagtg    1560
tataatgagc tgacaaaggt gaagtatgtg acagagggca tgagaaagcc tgccttcctg    1620
tctggagagc agaagaaggc cattgtggac ctgctgttta agaccaatag gaaggtgaca    1680
gtgaagcagc tgaaggagga ctatttcaag aagattgagt gttttgattc tgtggagatc    1740
tctggagtgg aggacagatt caatgcaagc ctgggcacct accatgatct gctgaagatc    1800
atcaaggata aggacttcct ggacaatgag gagaatgagg atatcctgga ggacattgtg    1860
ctgaccctga cactgtttga ggataggag atgattgagg agagactgaa gacatatgcc    1920
cacctgtttg atgacaaagt gatgaagcag ctgaagagaa ggagatacac tggatggggc    1980
aggctgtcca gaaagctgat caatggcatc agagacaagc agtctggcaa gacaatcctg    2040
gactttctga agtctgatgg cttgtgccaac aggaacttca tgcagctgat ccatgatgac    2100
tccctgacct tcaaggagga tatccagaag gcacaggtgt ctggacaggg agactctctg    2160
catgagcaca ttgccaacct ggctggctct cctgccatca gaagggcat cctgcagaca    2220 gtgaaggtgg tggatgagct ggtgaaagtg atgggcaggc acaagccaga gaacattgtg    2280
attgagatgg ccagagagaa tcagaccaca cagaagggcc agaagaacag cagggagaga    2340
atgaagagaa ttgaggaggg catcaaggag ctgggctccc agatcctgaa ggagcaccct    2400
gtggagaaca cacagctgca gaatgagaag ctgtatctgt actatctgca gaatggcaga    2460
gatatgtatg tggaccagga gctggatatc aacagactgt ctgattatga tgtggatcac    2520
attgtgccac agagcttcct gaaggatgac tccattgaca ataaggtgct gaccaggtct    2580
gacaagaaca gaggcaagtc tgataatgtg ccctcagagg aggtggtgaa gaagatgaag    2640
aactactgga ggcagctgct gaatgccaag ctgatcacac agaggaagtt tgataacctg    2700
accaaggcag agaggaggag cctgtctgag ctggacaagg caggcttcat caagaggcag    2760
ctggtggaga caagacagat cacaaagcat gtggcccaga tcctggattc tagaatgaac    2820
acaaagtatg atgagaatga caagctgatc agggaggtga aagtgatcac cctgaagtct    2880
aagctggtgt cagactttag gaaggatttc cagtttttata aggtgagaga gatcaacaac    2940
taccaccatg cccatgatgc ctacctgaat gctgtggtgg gcacagccct gatcaagaag    3000 tacccctaagc tggagtctga gtttgtgtat ggagactata aggtgtatga tgtgaggaag    3060
atgattgcca agtctgagca ggagattggc aaggccacag ccaagtattt cttttactct    3120
aacatcatga atttctttaa gacagagatc acactggcca atggagagat caggaagaga    3180
ccactgattg agacaaatgg agagacagga gagattgtgt gggacaaggg cagagatttt    3240
gccacagtga gaaaggtgct gagcatgccc caagtgaata ttgtgaagaa gactgaggtg    3300
cagacaggag gcttctctaa ggagagcatc ctgcctaaga ggaactctga taagctgatt    3360
gccagaaaga aggactggga tcctaagaag tatggaggct ttgactctcc aacagtggcc    3420
tactcagtgc tggtggtggc caaggtggag aagggcaagt ctaagaagct gaagtctgtg    3480
aaggagctgc tgggcatcac catcatggag agaagctcct tgagaagaa tcctattgat    3540 tttctggagg ccaagggcta taaggaggtg aagaaggacc tgatcatcaa gctgccaaag    3600
```

```
tactccctgt tgagctgga gaatggcagg aagagaatgc tggcatctgc tggagagctg    3660
cagaagggca atgagctggc cctgcccagc aagtatgtga acttcctgta tctggcctcc    3720
cactatgaga agctgaaggg ctcccctgag gataatgagc agaagcagct gtttgtggag    3780
cagcacaagc actatctgga tgagatcatt gagcagatct cagagttctc taagagagtg    3840
atcctggctg atgccaatct ggataaggtg ctgagtgcct acaacaagca cagggataag    3900
ccaatcagag agcaggcaga gaatatcatc cacctgttca ccctgacaaa cctgggagca    3960
ccagcagcct tcaagtattt tgacaccaca attgatagga gaggtacac ctccacaaag     4020 gaggtgctgg atgccaccct gatccaccag agcatcacag gcctgtatga gacaaggatt    4080
gacctgtccc agctgggagg agaccccaag aagaagagga aggtgtga                4128

<210> SEQ ID NO 7
<211> LENGTH: 4128
<212> TYPE: DNA
<213> ORGANISM: Artificial Sequence
<220> FEATURE:
<223> OTHER INFORMATION: Recombinant Sequence

<400> SEQUENCE: 7
atggacaaga agtactccat cggcctggac atcgggacca acagcgtggg ctgggccgtg      60
atcaccgacg agtacaaggt gcccctccaag aagttcaagg tgctggggaa caccgacaga   120
cacagcatca agaagaacct gatcggcgcc ctgctgttcg actccggaga aaccgctgag    180
gctacccgcc tgaagagaac cgctcgccgg aggtacacac gacgcaagaa caggatctgc    240
tacctgcagg agatcttctc caacgagatg gccaaggtgg acgactcctt cttccaccgg    300
ctggaggaga gcttcctggt ggaggaggac aagaagcacg agaggcaccc catcttcggc    360
aacatcgtgg acgaggtggc ctaccacgag aagtacccca ccatctacca cctgaggaag    420
aagctggtgg actccaccga caaggccgac ctgagactga tctacctggc cctggcccac    480
atgatcaagt tccgcggcca cttcctgatc gaggggggacc tgaaccccga caacagcgac    540
gtggacaagc tgttcatcca gctggtgcag acctacaacc agctgttcga ggagaacccc    600
atcaacgctt ccggagtgga cgctaaggct atcctgagcg ccagactgtc caagagccgg    660
aggctggaga acctgatcgc ccagctgccc ggcgagaaga gaaacggcct gttcgggaac    720
ctgatcgccc tgtccctggg gctgaccccc aacttcaaga gcaatttcga cctggccgag    780
gacgccaagc tgcagctgtc caaggacacc tacgacgacg acctggacaa cctgctggcc    840
cagatcggcg accagtacgc cgacctgttc ctggccgcca gaaacctgtc cgacgccatc    900
ctgctgagcg acatcctgcg cgtgaacacc gagatcacca aggcccccct gtccgccagc    960
atgatcaaga gatacgacga gcaccaccag gacctgaccc tgctgaaggc cctggtgcgc   1020
cagcagctgc ccgagaagta caaggagatc ttcttcgacc agagcaagaa cggatacgct   1080
ggatacatcg acggaggagc ctcccaggag gagttctaca agttcatcaa gcccatcctg   1140
gagaagatgg acggcaccga ggagctgctg gtgaagctga accgggagga cctgctgagg   1200
aagcagagaa ccttcgacaa cggctccatc ccccaccaga tccacctggg ggagctgcac   1260
gccatcctga gacgccagga ggacttctac cccttcctga aggacaacag ggagaagatc   1320
gagaagatcc tgaccttcag aatcccatac tacgtgggac actggctagg ggaaactcc   1380 agattcgcct ggatgacccg gaagagcgag gaaaccatca ccccctggaa cttcgaggag   1440
gtggtggaca agggagcttc cgcccagagc ttcatcgaga ggatgaccaa cttcgacaag   1500
```

```
aacctgccca acgagaaggt gctgcccaag cactccctgc tgtacgagta cttcaccgtg    1560
tacaacgagc tgaccaaggt gaagtacgtg accgagggca tgagaaagcc cgccttcctg    1620
agcggggagc agaagaaggc catcgtggac ctgctgttca agaccaaccg caaggtgacc    1680
gtgaagcagc tgaaggagga ctacttcaag aagatcgagt gcttcgactc cgtggagatc    1740
agcggagtgg aggaccgctt caacgcttcc ctggggacct accacgacct gctgaagatc    1800
atcaaggaca aggacttcct ggacaacgag gagaacgagg acatcctgga ggacatcgtg    1860
ctgaccctga ccctgttcga ggaccgcgag atgatcgagg agcggctgaa gacctacgcc    1920
cacctgttcg acgacaaggt catgaagcag ctgaagcgga ggagatacac cggatggggg    1980
cgcctgagca gaaagctgat caacggcatc cgggacaagc agtccgggaa gaccatcctg    2040
gacttcctga gagcgacggc ttcgccaac aggaacttca tgcagctgat ccacgacgac    2100
tccctgacct tcaaggagga catccagaag gctcaggtgt ccggacaggg ggacagcctg    2160
cacgagcaca tcgctaacct ggctggcagc cccgccatca agaaggggat cctgcagacc    2220
gtgaaggtgg tggacgagct ggtgaaggtc atgggcaggc acaagcccga gaacatcgtg    2280
atcgagatgg ccagagagaa ccagaccacc cagaaggggc agaagaactc ccgcgagcgg    2340
atgaagagga tcgaggaggg catcaaggag ctggggagcc agatcctgaa ggagcacccc    2400
gtggagaaca cccagctgca gaacgagaag ctgtacctgt actacctgca gaacggccgc    2460
gacatgtacg tggaccagga gctggacatc aaccggctgt ccgactacga cgtggaccac    2520
atcgtgcccc agtccttcct gaaggacgac agcatcgaca caaggtgct gacccgcagc    2580 gacaagaacc gggggaagtc cgacaacgtg cccagcgagg aggtggtgaa gaagatgaag    2640
aactactggc gccagctgct gaacgccaag ctgatcaccc agcgcaagtt cgacaacctg    2700
accaaggctg agagaggagg gctgtccgag ctggacaagg ccggcttcat caagaggcag    2760
ctggtggaaa ccagacagat caccaagcac gtggcccaga tcctggacag ccggatgaac    2820
accaagtacg acgagaacga caagctgatc agggaggtga aggtcatcac cctgaagtcc    2880
aagctggtga gcgacttccg caaggacttc cagttctaca aggtgcggga gatcaacaac    2940
taccaccacg cccacgacgc ttacctgaac gctgtggtgg aaccgcccct gatcaagaag    3000
taccccaagc tggagtccga gttcgtgtac ggggactaca aggtgtacga cgtgcgcaag    3060
atgatcgcca gtccgagca ggagatcggc aaggccaccg ccaagtactt cttctacagc    3120
aacatcatga acttcttcaa gaccgagatc accctggcca acggcgagat caggaagcgc    3180
cccctgatcg aaaccaacgg cgaaaccgga gagatcgtgt gggacaaggg aagagacttc    3240
gctaccgtgc ggaaggtgct gtccatgccc caggtgaaca tcgtgaagaa gaccgaggtg    3300
cagaccggcg ggttctccaa ggagagcatc ctgcccaaga ggaacagcga caagctgatc    3360
gccagaaaga aggactggga ccccaagaag tacgaggat tcgactcccc aaccgtggct    3420
tacagcgtgc tggtggtggc caaggtggag aagggcaagt ccaagaagct gaagagcgtg    3480
aaggagctgc tgggatcac catcatggag cggtccagct cgagaagaa ccccatcgac    3540 ttcctggagg ccaagggcta caaggaggtg aagaaggacc tgatcatcaa gctgcccaag    3600
tacagcctgt tcgagctgga gaacggaaga aagagaatgc tggcttccgc cggagagctg    3660
cagaagggaa acgagctggc cctgcccagc aagtacgtga acttcctgta cctggcctcc    3720
cactacgaga gctgaagggg cagccccgag gacaacgagc agaagcagct gttcgtggag    3780
cagcacaagc actacctgga cgagatcatc gagcagatct ccgagttcag caagcgcgtg    3840
atcctggccg acgccaacct ggacaaggtg ctgtccgcct acaacaagca cagggacaag    3900
```

```
cccatcagag agcaggccga gaacatcatc cacctgttca ccctgaccaa cctgggagct    3960
ccagctgcct tcaagtactt cgacaccacc atcgacagga gagatacaca cagcaccaag    4020
gaggtgctgg acgccaccct gatccaccag tccatcaccg gcctgtacga accagaatc    4080 gacctgagcc agctgggagg cgaccccaag aagaagcgca aggtgtga                4128
```

<210> SEQ ID NO 8
<211> LENGTH: 146
<212> TYPE: DNA
<213> ORGANISM: Artificial Sequence
<220> FEATURE:
<223> OTHER INFORMATION: Recombinant Sequence

<400> SEQUENCE: 8

```
gttaatcatt aagtcgttaa ttttgtggc ccttgcgatg tttgctctgg ttaataatct     60
caggacaaac agaggttaat aattttccag atctctctga gcaatagtat aaaaggccag    120
cagcagcctg accacatctc atcctc                                        146
```

<210> SEQ ID NO 9
<211> LENGTH: 1368
<212> TYPE: PRT
<213> ORGANISM: Streptococcus pyogenes

<400> SEQUENCE: 9

```
Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
```

```
                    245                 250                 255
Asp Leu Ala Glu Asp Ala Lys Leu Gln Leu Ser Lys Asp Thr Tyr Asp
                260                 265                 270

Asp Leu Asp Asn Leu Leu Ala Gln Ile Gly Asp Gln Tyr Ala Asp
    275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
                340                 345                 350

Asp Gln Ser Lys Asn Gly Tyr Ala Gly Tyr Ile Asp Gly Gly Ala Ser
                355                 360                 365

Gln Glu Glu Phe Tyr Lys Phe Ile Lys Pro Ile Leu Glu Lys Met Asp
        370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                    405                 410                 415

Gly Glu Leu His Ala Ile Leu Arg Arg Gln Glu Asp Phe Tyr Pro Phe
                420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
                500                 505                 510

Leu Leu Tyr Glu Tyr Phe Thr Val Tyr Asn Glu Leu Thr Lys Val Lys
            515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
                580                 585                 590

Thr Tyr His Asp Leu Leu Lys Ile Ile Lys Asp Lys Asp Phe Leu Asp
            595                 600                 605

Asn Glu Glu Asn Glu Asp Ile Leu Glu Asp Ile Val Leu Thr Leu Thr
    610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670
```

```
Lys Gln Ser Gly Lys Thr Ile Leu Asp Phe Leu Lys Ser Asp Gly Phe
            675                 680                 685

Ala Asn Arg Asn Phe Met Gln Leu Ile His Asp Asp Ser Leu Thr Phe
        690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
                755                 760                 765

Thr Thr Gln Lys Gly Gln Lys Asn Ser Arg Glu Arg Met Lys Arg Ile
    770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp His Ile Val Pro Gln Ser Phe Leu Lys
        835                 840                 845

Asp Asp Ser Ile Asp Asn Lys Val Leu Thr Arg Ser Asp Lys Asn Arg
    850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
    930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys Tyr Pro Lys Leu Glu Ser Glu Phe
        995                 1000                1005

Val Tyr Gly Asp Tyr Lys Val Tyr Asp Val Arg Lys Met Ile Ala
    1010                1015                1020

Lys Ser Glu Gln Glu Ile Gly Lys Ala Thr Ala Lys Tyr Phe Phe
    1025                1030                1035

Tyr Ser Asn Ile Met Asn Phe Phe Lys Thr Glu Ile Thr Leu Ala
    1040                1045                1050

Asn Gly Glu Ile Arg Lys Arg Pro Leu Ile Glu Thr Asn Gly Glu
    1055                1060                1065

Thr Gly Glu Ile Val Trp Asp Lys Gly Arg Asp Phe Ala Thr Val
    1070                1075                1080
```

```
Arg Lys Val Leu Ser Met Pro Gln Val Asn Ile Val Lys Lys Thr
    1085                1090            1095
Glu Val Gln Thr Gly Gly Phe Ser Lys Glu Ser Ile Leu Pro Lys
    1100                1105            1110
Arg Asn Ser Asp Lys Leu Ile Ala Arg Lys Lys Asp Trp Asp Pro
    1115                1120            1125
Lys Lys Tyr Gly Gly Phe Asp Ser Pro Thr Val Ala Tyr Ser Val
    1130                1135            1140
Leu Val Val Ala Lys Val Glu Lys Gly Lys Ser Lys Lys Leu Lys
    1145                1150            1155
Ser Val Lys Glu Leu Leu Gly Ile Thr Ile Met Glu Arg Ser Ser
    1160                1165            1170
Phe Glu Lys Asn Pro Ile Asp Phe Leu Glu Ala Lys Gly Tyr Lys
    1175                1180            1185
Glu Val Lys Lys Asp Leu Ile Ile Lys Leu Pro Lys Tyr Ser Leu
    1190                1195            1200
Phe Glu Leu Glu Asn Gly Arg Lys Arg Met Leu Ala Ser Ala Gly
    1205                1210            1215
Glu Leu Gln Lys Gly Asn Glu Leu Ala Leu Pro Ser Lys Tyr Val
    1220                1225            1230
Asn Phe Leu Tyr Leu Ala Ser His Tyr Glu Lys Leu Lys Gly Ser
    1235                1240            1245
Pro Glu Asp Asn Glu Gln Lys Gln Leu Phe Val Glu Gln His Lys
    1250                1255            1260
His Tyr Leu Asp Glu Ile Ile Glu Gln Ile Ser Glu Phe Ser Lys
    1265                1270            1275
Arg Val Ile Leu Ala Asp Ala Asn Leu Asp Lys Val Leu Ser Ala
    1280                1285            1290
Tyr Asn Lys His Arg Asp Lys Pro Ile Arg Glu Gln Ala Glu Asn
    1295                1300            1305
Ile Ile His Leu Phe Thr Leu Thr Asn Leu Gly Ala Pro Ala Ala
    1310                1315            1320
Phe Lys Tyr Phe Asp Thr Thr Ile Asp Arg Lys Arg Tyr Thr Ser
    1325                1330            1335
Thr Lys Glu Val Leu Asp Ala Thr Leu Ile His Gln Ser Ile Thr
    1340                1345            1350
Gly Leu Tyr Glu Thr Arg Ile Asp Leu Ser Gln Leu Gly Gly Asp
    1355                1360            1365
```

CAS9 NUCLEIC ACID MOLECULES AND THEIR USE

CROSS REFERENCE TO RELATED APPLICATION

This application is a continuation of U.S. patent application Ser. No. 15/673,115, filed Aug. 9, 2017, which claims the benefit of U.S. Provisional Application No. 62/372,584, filed Aug. 9, 2016. The aforementioned applications are incorporated by reference herein in their entirety.

FIELD

This application pertains to nucleic acid molecules encoding Cas9 and their use.

BACKGROUND

The CRISPR-Cas system does not require the generation of customized proteins to target specific sequences but rather a single Cas enzyme can be programmed by a short guide RNA molecule to recognize a specific DNA target. To utilize the CRISPR-Cas system effectively for genome editing without deleterious effects, compositions and methods are needed for optimization and cell-type/tissue/organ specific delivery of these genome engineering tools.

Classic codon optimization introduces synonymous codon substitutions to better match the exogenous gene's codon usage to the codon usage preference of the host. Codon optimization is routinely successful for prokaryotes and unicellular eukaryotes, but has been historically less successful in multicellular eukaryotes.

Classical codon optimization does not take into account differences in codon usage and tRNA frequencies amongst tissue and cell types. There is a need in the art for tissue specific expression of Cas9 and a Cas9 nucleic acid sequence for enhanced expression within a target tissue.

SUMMARY

Disclosed herein are recombinant nucleic acid molecules encoding Cas9 that provide increased expression of Cas9 protein in human liver. In several embodiments, the recombinant nucleic acid molecules encoding Cas9 are codon-optimized for expression in human liver. The recombinant nucleic acid molecules can be used, for example, for expression of Cas9 in the liver, and in CRISPR/Cas9 methods involving gene editing in the liver.

In some embodiments, a recombinant nucleic acid molecule is provided that comprises a nucleic acid sequence encoding Cas9 that provides increased expression in human liver compared to native Cas9 sequences. In several embodiments, the recombinant nucleic acid molecule comprises a nucleotide sequence at least 95% (such as at least 98%, at least 99%, or 100%) identical to SEQ ID NO: 1 or 2. In some embodiments, a vector including the recombinant nucleic acid molecules encoding Cas9 that provide increased expression of Cas9 protein in human liver is linked to a promoter. In some embodiments, the vector is an adeno-associated virus (AAV) vector. Methods of making such vectors are also provided.

In some embodiments, an adeno associated virus (AAV) cassette comprising the recombinant nucleic acid molecules encoding Cas9 that provide increased expression of Cas9 protein in human liver. In some embodiments, the nucleic acid molecule is operably linked to a liver specific promoter (such as a Hepatic Combinatorial Bundle (HCB) promoter), left and right inverted terminal repeats (ITR), and a synthetic polyadenylation (SpA) signal.

In some embodiments, a method is provided for gene-editing liver tissue, including delivering the recombinant nucleic acid molecule encoding Cas9 to the liver tissue, and further delivering guide RNAs to the liver tissue.

The foregoing and other features and advantages of this disclosure will become more apparent from the following detailed description of several embodiments which proceeds with reference to the accompanying drawings.

BRIEF DESCRIPTION OF THE DRAWINGS

FIG. 1A shows the codon frequency of the human genome.

FIG. 2A-FIG. 2C show comparative heat maps of codon frequencies for mouse genome vs human genome (FIG. 2A); hepatocyte vs whole human (FIG. 2B); and myeloid vs. whole human (FIG. 2C).

FIG. 3A and FIG. 3B are a graph (FIG. 3A) and table (FIG. 3B) demonstrating the fold difference in codon frequencies of mouse genome, liver, and myeloid cells from human whole genome codon frequencies. The mean fold difference of mouse genome codon frequencies from that of the whole human genome is 0.046. The mean fold difference of liver codon frequencies from that of the whole human genome is 0.150. The mean fold difference of myeloid cell codon frequencies from that of the human genome is 0.135.

FIG. 5 is a table displaying the codon usage indices for human liver. Codon frequency and codon count are shown.

FIG. 6 is a table showing the percent sequence identity of the sequences of SEQ ID NO: 1 and SEQ ID NO: 2 and the starting Cas9 sequence of SEQ ID NO: 3.

FIG. 7A-FIG. 7C show a series of graphs of liver codon adaptive index (CAI) for the starting Cas9 sequence (FIG. 7A) (SEQ ID NO: 3), a recombinant Cas9 sequence with codon-optimization for expression in human liver and including CpG motifs (FIG. 7B) (SEQ ID NO: 1), and a recombinant Cas9 sequence with codon-optimization for expression in human liver and without CpG (FIG. 7C) (SEQ ID NO: 2).

FIG. 8A-FIG. 8C show a series of graphs of Frequency of Optimal Codons (FOP) for the starting Cas9 sequence (FIG. 8A) (SEQ ID NO: 3), a recombinant Cas9 sequence with CpG (FIG. 8B) (SEQ ID NO: 1), and a recombinant Cas9 sequence without CpG (FIG. 8C) (SEQ ID NO: 2). The FOP is generated against the custom human liver codon usage index.

FIG. 9A-FIG. 9C show a series of graphs of GC content for the starting Cas9 sequence (FIG. 9A) (SEQ ID NO: 3), a recombinant Cas9 sequence with CpG (FIG. 9B) (SEQ ID NO: 1), and a recombinant Cas9 sequence without CpG (FIG. 9C) (SEQ ID NO: 2). The ideal percentage range of GC content is between %. Peaks of % GC content in a 60 bp window have been removed.

FIG. 10 is a table listing the numbers of cis-acting elements and antiviral motifs in the starting Cas9 sequence (SEQ ID NO: 3), a recombinant Cas9 sequence with CpG (SEQ ID NO: 1), and a recombinant Cas9 sequence without CpG (SEQ ID NO: 2).

SEQUENCE LISTING

Figure 1B:
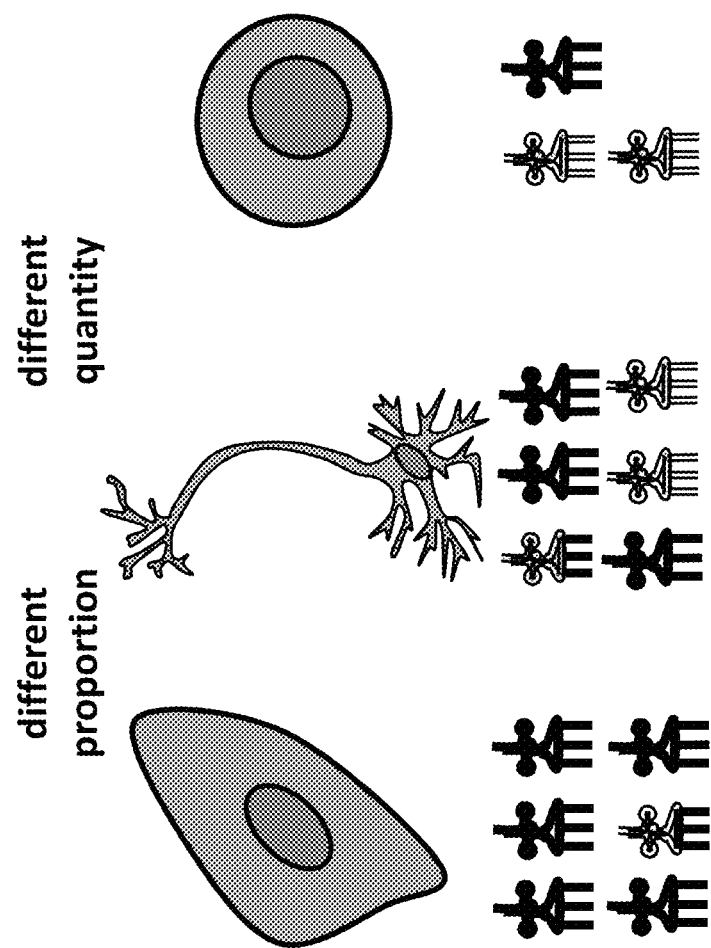
FIG. 1B is an illustration showing that measured levels of tRNA content vary in both proportion and quantity among cell types.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file in the form of the file named "Sequence.txt" (~49.8 KB), which was created on Apr. 27, 2020, and is incorporated by reference herein. In the accompanying Sequence Listing:

SEQ ID NO: 1 is a recombinant Cas9 nucleic acid sequence for increased protein expression in human liver that contains CpG motifs.

SEQ ID NO: 2 is a recombinant Cas9 nucleic acid sequence without CpGs.

SEQ ID NO: 3 is an exemplary starting Cas9 nucleic acid sequence.

SEQ ID NO: 4 is a recombinant Cas9-NLS-NCG nucleic acid sequence for increased protein expression in human cells.

SEQ ID NO: 5 is a recombinant Cas9-NLS-WCG Genscript nucleic acid sequence for increased protein expression in human cells.

SEQ ID NO: 6 is a recombinant Cas9-NLS-NCG Genscript nucleic acid sequence for increased protein expression in human liver.

SEQ ID NO: 7 is a recombinant Cas9-NLS-WCG nucleic acid sequence for increased protein expression in human liver.

SEQ ID NO: 8 is the nucleic acid sequence of the Hepatic Combinatorial Bundle, or HCB promoter.

SEQ ID NO: 9 is an amino acid sequence of Cas9.

DETAILED DESCRIPTION

I. Overview

Described herein are recombinant nucleic acid molecules for increased expression of Cas9 in human liver, and their use. The recombinant nucleic acid molecules can be used in combination with CRISPR for targeted gene-editing in a tissue specific capacity. The compositions and methods of the present disclosure can be used in gene therapy for proteins produced in the liver, which can target protein encoding genes themselves, or genetic regulatory elements, and for understanding liver or liver tissue gene function.

Clinical gene therapy frequently is encumbered by low transgene product biosynthesis at predictably safe vector doses. It has been hypothesized that the presence of rare codons may regulate transgene product expression through depletion of the available cognate tRNA pool. Codon optimization is the prominent strategy utilized to overcome this hypothesized limitation and involves replacing rare, presumably translation-rate limiting, codons with the more frequent ones. Typical algorithms attempt to match the codon usage frequency of the target organism's total mRNA pool, which has been shown to approximate the overall available tRNA concentrations. However, upon closer examination, it appears that both codon frequency and tRNA content vary between tissue types.

Although human-codon optimized Cas9 sequences have been described, these sequences are predicted to suffer from limitations for in vivo expression at least related to tRNA frequencies. Accordingly, provided herein are recombinant nucleic acid molecules encoding Cas9 that provide increased expression of Cas9 protein in specific human tissues (such as the liver) compared to native Cas9 sequences.

Also provided is a liver-codon optimized CRISPR (Clustered Regularly Interspaced Short Palindromic Repeats)/Cas9 (CRISPR associated protein 9) system designed for efficient in vivo genome editing. The native CRISPR/Cas9 system represents a form of adaptive immunity present in *Streptococcus pyrogenes* and other bacteria. However, in recent years, it has become the most utilized tool in the genome editing field and now provides the basis for several biotherapeutic approaches as well as genetically-modified crop and food-producing animals. One such therapeutic approach involves the in vivo delivery of Cas9, specific guide RNAs and DNA fragments containing homology to a specific target region of the genome as well as some sequence of predicted therapeutic value to be inserted into the genome. One barrier to this approach lies in the bacterial nature of the Cas9 sequence, which is not well codon optimized for expression in humans or other vertebrates.

The liver is a major target for gene therapy, including genome editing approaches. Thus, a recombinant Cas9 nucleic acid molecule with sequence modifications to increase expression in liver will enable liver-directed in vivo genome editing.

II. Terms

Unless otherwise noted, technical terms are used according to conventional usage. Definitions of common terms in molecular biology may be found in Benjamin Lewin, Genes V, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the disclosure, the following explanations of specific terms are provided:

Adeno-associated virus (AAV): A small, replication-defective, non-enveloped virus that infects humans and some other primate species. AAV is not known to cause disease and elicits a very mild immune response. Gene therapy vectors that utilize AAV can infect both dividing and quiescent cells and can persist in an extrachromosomal state without integrating into the genome of the host cell. These features make AAV an attractive viral vector for gene therapy. There are currently 11 recognized serotypes of AAV (AAV1-11).

Administration/Administer: To provide or give a subject an agent, such as a therapeutic agent (e.g. a recombinant AAV), by any effective route. Exemplary routes of administration include, but are not limited to, injection (such as subcutaneous, intramuscular, intradermal, intraperitoneal, and intravenous), oral, intraductal, sublingual, rectal, transdermal, intranasal, vaginal and inhalation routes.

Cas9: An RNA-guided RNA endonuclease enzyme that can cut DNA. Cas9 has two active cutting sites (HNH and RuvC), one for each strand of the double helix. An exemplary native Cas9 protein sequence is shown in SEQ ID NO: 9.

Cas9 sequences are publicly available. For example, GenBank® Accession Nos. nucleotides 796693 . . . 800799 of CP012045.1 and nucleotides 1100046 . . . 1104152 of CP014139.1 disclose Cas9 nucleic acids, and GenBank® Accession Nos. NP_269215.1, AMA70685.1 and AKP81606.1 disclose Cas9 proteins. Cas9 is further described in UniProt entry Q99ZW2.

cDNA (complementary DNA): A piece of DNA lacking internal, non-coding segments (introns) and regulatory sequences that determine transcription. cDNA is synthesized in the laboratory by reverse transcription from messenger RNA extracted from cells. cDNA can also contain untranslated regions (UTRs) that are responsible for translational control in the corresponding RNA molecule.

Complementarity: The ability of a nucleic acid to form hydrogen bond(s) with another nucleic acid sequence by either traditional Watson-Crick base pairing or other non-traditional types. A percent complementarity indicates the percentage of residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" means that all the contiguous residues of a nucleic acid sequence will hydrogen bond with the same number of contiguous residues in a second nucleic acid sequence. "Substantially complementary" as used herein refers to a degree of complementarity that is at least 60%, 65%, 70%, 75%, 80%, 85%, 90%, 95%, 97%, 98%, 99%, or 100% over a region of 8, 9, 10, 11, 12, 13, 14, 15, 16, 17, 18, 19, 20, 21, 22, 23, 24, 25, 30, 35, 40, 45, 50, or more nucleotides, or refers to two nucleic acids that hybridize under stringent conditions.

Codon-optimized: A "codon-optimized" nucleic acid refers to a nucleic acid sequence that has been altered such that the codons are optimal for expression in a particular system (such as a particular species or tissue). For example, a nucleic acid sequence can be optimized for expression in mammalian cells or in a particular mammalian species (such as human cells), cell type, or tissue (such as a human liver). Codon optimization does not alter the amino acid sequence of the encoded protein.

CpG dinucleotide: DNA base cytosine followed by guanine. Cytosines in CpG dinucleotides can be methylated to form 5-methylcytosine. This methylation can alter gene expression.

CRISPR (clustered regularly interspaced short palindromic repeats): DNA loci containing short repetitions of base sequences. Each repetition is followed by short segments of "spacer DNA" from previous exposures to a virus. CRISPRs are found in approximately 40% of sequenced bacteria genomes and 90% of sequenced archaea. CRISPRs are often associated with cas genes that code for proteins related to CRISPRs. The CRISPR/Cas system is a prokaryotic immune system that confers resistance to foreign genetic elements such as plasmids and phages and provides a form of acquired immunity. CRISPR spacers recognize and cut these exogenous genetic elements in a manner analogous to RNAi in eukaryotic organisms. The CRISPR/Cas system can be used for gene editing (adding, disrupting or changing the sequence of specific genes) and gene regulation. By delivering the Cas9 sequence and appropriate guide RNAs into a cell, the organism's genome can be cut at any desired location.

DNA (deoxyribonucleic acid): DNA is a long chain polymer which comprises the genetic material of most living organisms (some viruses have genes comprising ribonucleic acid (RNA)). The repeating units in DNA polymers are four different nucleotides, each of which comprises one of the four bases, adenine (A), guanine (G), cytosine (C), and thymine (T) bound to a deoxyribose sugar to which a phosphate group is attached. Triplets of nucleotides (referred to as codons) code for each amino acid in a polypeptide, or for a stop signal. The term codon is also used for the corresponding (and complementary) sequences of three nucleotides in the mRNA into which the DNA sequence is transcribed.

Unless otherwise specified, any reference to a DNA molecule is intended to include the reverse complement of that DNA molecule. Except where single-strandedness is required by the text herein, DNA molecules, though written to depict only a single strand, encompass both strands of a double-stranded DNA molecule. Thus, a reference to the nucleic acid molecule that encodes a specific protein, or a fragment thereof, encompasses both the sense strand and its reverse complement. For instance, it is appropriate to generate probes or primers from the reverse complement sequence of the disclosed nucleic acid molecules.

Gene: A nucleic acid sequence, typically a DNA sequence, that comprises control and coding sequences necessary for the transcription of an RNA, whether an mRNA or otherwise. For instance, a gene may comprise a promoter, one or more enhancers or silencers, a nucleic acid sequence that encodes a RNA and/or a polypeptide, downstream regulatory sequences and, possibly, other nucleic acid sequences involved in regulation of the expression of an mRNA.

Most eukaryotic genes contain both exons and introns. The term "exon" refers to a nucleic acid sequence found in genomic DNA that is bioinformatically predicted and/or experimentally confirmed to contribute a contiguous sequence to a mature mRNA transcript. The term "intron" refers to a nucleic acid sequence found in genomic DNA that is predicted and/or confirmed not to contribute to a mature mRNA transcript, but rather to be "spliced out" during processing of the transcript.

Guide sequence: A polynucleotide sequence having sufficient complementarity with a target polynucleotide sequence to hybridize with the target sequence and direct sequence-specific binding of a Cas9 to the target sequence. In some examples, the guide sequence is RNA. In some examples, the guide sequence is DNA. The guide nucleic acid can include modified bases or chemical modifications (e.g., see Latorre et al., Angewandte Chemie 55:3548-50, 2016). In some embodiments, the degree of complementarity between a guide sequence and its corresponding target sequence, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g. the Burrows Wheeler Aligner), ClustalW, Clustal X, BLAT, Novoalign (Novocraft Technologies, ELAND (Illumina, San Diego, Calif.), SOAP (available at soap.genomics.org.cn), and Maq (available at maq.sourceforge.net). In some embodiments, a guide sequence is about, or at least, about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments, a guide sequence is less than about 75, 50, 45, 40, 35, 30, 25, 20, 15, 12, or fewer nucleotides in length. In some embodiments, a guide sequence is 15-25 nucleotides (such as 18-22 or 18 nucleotides).

The ability of a guide sequence to direct sequence-specific binding of a CRISPR complex to a target sequence may be assessed by any suitable assay. For example, the components of a CRISPR system sufficient to form a CRISPR complex, including the guide sequence to be tested, may be provided to a host cell having the corresponding target sequence, such as by transfection with vectors encoding the components of the CRISPR sequence, followed by an assessment of preferential cleavage within the target sequence, such as by Surveyor assay as described herein. Similarly, cleavage of a target polynucleotide sequence may be evaluated in a test tube by providing the target sequence, components of a CRISPR complex, including the guide sequence to be tested and a control guide sequence different from the test guide sequence, and comparing binding or rate of cleavage at the target sequence between the test and control guide sequence reactions.

Homology-directed repair (HDR): A mechanism to repair double stranded DNA lesions. The CRISPR/Cas9 methods disclosed herein, such as those that use a disclosed recombinant Cas9 nucleic acid molecule, can be used for HDR of one or more target genes, for example during G2 and S phase of the cell cycle.

Intron: A stretch of DNA within a gene that does not contain coding information for a protein. Introns are removed before translation of a messenger RNA.

Inverted terminal repeat (ITR): Symmetrical nucleic acid sequences in the genome of adeno-associated viruses that promotes efficient replication. ITR sequences are located at each end of the AAV DNA genome. The ITRs serve as the origins of replication for viral DNA synthesis and are essential cis components for generating AAV integrating vectors.

Isolated: An "isolated" biological component (such as a nucleic acid molecule, protein, virus or cell) has been substantially separated or purified away from other biological components in the cell or tissue of the organism, or the organism itself, in which the component naturally occurs, such as other chromosomal and extrachromosomal DNA and RNA, proteins and cells. Nucleic acid molecules and proteins that have been "isolated" include those purified by standard purification methods. The term also embraces nucleic acid molecules and proteins prepared by recombinant expression in a host cell as well as chemically synthesized nucleic acid molecules and proteins.

Liver: The liver is an organ found in vertebrates serving a wide range of functions, including detoxification, protein synthesis, and the production of biochemical utilized in digestions. Liver or liver tissue includes parenchymal cells commonly referred to as hepatocytes. Liver or Liver tissue can also be liver cells that are non-parenchymal cells, especially as such cells constitute 40% of the total number of liver cells even though only 6.5% of its volume; and, examples of such non-parenchymal cells liver cells or tissue include sinusoidal hepatic endothelial cells, kupffer cells and hepatic stellate cells. Cells of the liver express one or more liver gene product(s).

Modulate: A change in the content of genomic DNA gene. Modulation can include, but is not limited to, gene activation (e.g., upregulation), gene repression (e.g., downregulation), gene deletion, polynucleotide insertion, and/or polynucleotide excision.

Non-homologous end-joining (NHEJ): A mechanism that repairs double stranded breaks in DNA. The CRISPR/Cas9 methods disclosed herein, such as those that use a disclosed recombinant Cas9 nucleic acid molecule, can be used for NHEJ of one or more target genes.

Nucleic acid molecule: A polymeric form of nucleotides, which may include both sense and anti-sense strands of RNA, cDNA, genomic DNA, and synthetic forms and mixed polymers of the above. A nucleotide refers to a ribonucleotide, deoxynucleotide or a modified form of either type of nucleotide. The term "nucleic acid molecule" as used herein is synonymous with "nucleic acid" and "polynucleotide." A nucleic acid molecule is usually at least 10 bases in length, unless otherwise specified. The term includes single- and double-stranded forms of DNA. A polynucleotide may include either or both naturally occurring and modified nucleotides linked together by naturally occurring and/or non-naturally occurring nucleotide linkages. "cDNA" refers to a DNA that is complementary or identical to an mRNA, in either single stranded or double stranded form. "Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom.

Nucleotide: This term includes, but is not limited to, a monomer that includes a base linked to a sugar, such as a pyrimidine, purine or synthetic analogs thereof, or a base linked to an amino acid, as in a peptide nucleic acid (PNA). A nucleotide is one monomer in a polynucleotide. A nucleotide sequence refers to the sequence of bases in a polynucleotide.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

ORF (open reading frame): A series of nucleotide triplets (codons) coding for amino acids. These sequences are usually translatable into a peptide.

Pharmaceutically acceptable carriers: The pharmaceutically acceptable carriers of use are conventional. Remington's Pharmaceutical Sciences, by E. W. Martin, Mack Publishing Co., Easton, Pa., 19th Edition, 1995, describes compositions and formulations suitable for pharmaceutical delivery of the disclosed vectors.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions (such as vector compositions) to be administered can contain minor amounts of non-toxic auxiliary substances, such as wetting or emulsifying agents, preservatives, and pH buffering agents and the like, for example sodium acetate or sorbitan monolaurate. In particular embodiments, suitable for administration to a subject the carrier may be sterile, and/or suspended or otherwise contained in a unit dosage form containing one or more measured doses of the composition suitable to induce the desired immune response. It may also be accompanied by medications for its use for treatment purposes. The unit dosage form may be, for example, in a sealed vial that contains sterile contents or a syringe for injection into a subject, or lyophilized for subsequent solubilization and administration or in a solid or controlled release dosage.

Polypeptide: Any chain of amino acids, regardless of length or post-translational modification (e.g., glycosylation or phosphorylation). "Polypeptide" applies to amino acid polymers including naturally occurring amino acid polymers and non-naturally occurring amino acid polymer as well as in which one or more amino acid residue is a non-natural amino acid, for example, an artificial chemical mimetic of a corresponding naturally occurring amino acid. A "residue" refers to an amino acid or amino acid mimetic incorporated in a polypeptide by an amide bond or amide bond mimetic. A polypeptide has an amino terminal (N-terminal) end and a carboxy terminal (C-terminal) end. "Polypeptide" is used interchangeably with peptide or protein, and is used herein to refer to a polymer of amino acid residues.

Preventing, treating or ameliorating a disease: "Preventing" a disease (such as a liver disorder, or disorder involving proteins expressed in the liver) refers to inhibiting the full development of a disease. "Treating" refers to a therapeutic intervention that ameliorates a sign or symptom of a disease or pathological condition after it has begun to develop. "Ameliorating" refers to the reduction in the number or severity of signs or symptoms of a disease.

Promoter: A region of DNA that directs/initiates transcription of a nucleic acid (e.g. a gene). A promoter includes necessary nucleic acid sequences near the start site of transcription. Typically, promoters are located near the genes they transcribe. A promoter also optionally includes distal enhancer or repressor elements which can be located as much as several thousand base pairs from the start site of transcription. A tissue-specific promoter is a promoter that directs/initiated transcription primarily in a single type of tissue or cell. For example, a liver-specific promoter is a promoter that directs/initiates transcription in liver tissue to a substantially greater extent than other tissue types.

Protein: A biological molecule expressed by a gene or other encoding nucleic acid (e.g., a cDNA) and comprised of amino acids.

Purified: The term "purified" does not require absolute purity; rather, it is intended as a relative term. Thus, for example, a purified peptide, protein, virus, vector, or other active compound is one that is isolated in whole or in part from naturally associated proteins and other contaminants. In certain embodiments, the term "substantially purified" refers to a peptide, protein, vector, virus or other active compound that has been isolated from a cell, cell culture medium, or other crude preparation and subjected to fractionation to remove various components of the initial preparation, such as proteins, cellular debris, and other components.

Recombinant: A recombinant nucleic acid molecule is one that has a sequence that is not naturally occurring, for example, includes one or more nucleic acid substitutions, deletions or insertions, and/or has a sequence that is made by an artificial combination of two otherwise separated segments of sequence. This artificial combination can be accomplished by chemical synthesis or, more commonly, by the artificial manipulation of isolated segments of nucleic acids, for example, by genetic engineering techniques.

A recombinant virus is one that includes a genome that includes a recombinant nucleic acid molecule. As used herein, "recombinant AAV" refers to an AAV particle in which a recombinant nucleic acid molecule (such as a recombinant nucleic acid molecule encoding a Cas9 protein) has been packaged.

Response element (RE): A DNA sequence included in a promoter to which one or more transcription factors can bind to and confer an aspect of control of gene expression.

Sequence identity: The identity or similarity between two or more nucleic acid sequences, or two or more amino acid sequences, is expressed in terms of the identity or similarity between the sequences. Sequence identity can be measured in terms of percentage identity; the higher the percentage, the more identical the sequences are. Sequence similarity can be measured in terms of percentage similarity (which takes into account conservative amino acid substitutions); the higher the percentage, the more similar the sequences are. Homologs or orthologs of nucleic acid or amino acid sequences possess a relatively high degree of sequence identity/similarity when aligned using standard methods. This homology is more significant when the orthologous proteins or cDNAs are derived from species which are more closely related (such as human and mouse sequences), compared to species more distantly related (such as human and *C. elegans* sequences).

Methods of alignment of sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene,* 73:237-44, 1988; Higgins & Sharp, *CABIOS* 5:151-3, 1989; Corpet et al., *Nuc. Acids Res.* 16:10881-90, 1988; Huang et al. *Computer Appls. in the Biosciences* 8, 155-65, 1992; and Pearson et al., *Meth. Mol. Bio.* 24:307-31, 1994. Altschul et al., *J. Mol. Biol.* 215:403-10, 1990, presents a detailed consideration of sequence alignment methods and homology calculations.

The NCBI Basic Local Alignment Search Tool (BLAST) (Altschul et al., *J. Mol. Biol.* 215:403-10, 1990) is available from several sources, including the National Center for Biological Information (NCBI) and on the internet, for use in connection with the sequence analysis programs blastp, blastn, blastx, tblastn and tblastx. Additional information can be found at the NCBI web site.

As used herein, reference to "at least 95% identity" refers to "at least 95%, at least 96%, at least 97%, at least 98%, at least 99%, or even 100% identity" to a specified reference sequence.

Subject: Living multi-cellular vertebrate organisms, a category that includes human and non-human mammals.

Therapeutically effective amount: A quantity of a specified pharmaceutical or therapeutic agent (e.g. a recombinant AAV) sufficient to achieve a desired effect in a subject, or in a cell, being treated with the agent. The effective amount of the agent will be dependent on several factors, including, but not limited to the subject or cells being treated, and the manner of administration of the therapeutic composition.

Vector: A vector is a nucleic acid molecule allowing insertion of foreign nucleic acid without disrupting the ability of the vector to replicate and/or integrate in a host cell. A vector can include nucleic acid sequences that permit it to replicate in a host cell, such as an origin of replication. A vector can also include one or more selectable marker genes and other genetic elements. An expression vector is a vector that contains the necessary regulatory sequences to allow transcription and translation of inserted gene or genes. In some embodiments herein, the vector is an adeno-associated virus (AAV) vector. In some embodiments, the vector is a gamma-retroviral vector, a lentiviral vector, or an adenoviral vector. An AAV vector can be produced by a cassette.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. As used herein, the term "comprises" means "includes." It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

III. Recombinant Cas9 Nucleic Acid Molecules

As discussed in the Examples, the cDNA nucleotide sequences coding for Cas9 were improved by implementing a codon usage bias specific for the human liver cell as compared to naturally occurring nucleotide sequence coding for the corresponding non-codon optimized sequence for a human. Additional changes were also made to improve translation efficacy, such as optimization of GC content, mRNA secondary structure, premature PolyA sites, RNA instability motif, stable free energy of mRNA, internal chi sites, ribosomal binding sites, cryptic splicing sites, negative CpG islands, SD sequence, TATA boxes, and cyptic terminal signals.

In addition, CpG DNA motifs were removed because they may lead to gene methylation and silencing. Codons were substituted with the most highly used human/liver alternative that did not result in the formation of a 5'-CG-3' dinucleotide in the sequence. CpG removal can also reduce any immune response to a vector including the modified transgene, enhancing the safety and efficacy of the vector. See J Clin Invest. 2013, 123(7):2994-3001, entitled "CpG-depleted adeno-associated virus vectors evade immune detection."

A recombinant Cas9 sequence with CpG dinucleotides is provided in SEQ ID NO: 1. A recombinant Cas9 sequence without CpG dinucleotides is provided in SEQ ID NO: 2. In certain embodiments, the recombinant Cas9 sequence is at least 95%, at least 96%, at least 97%, at least 98%, at least 99%, or at least 99.5% identical to SEQ ID NO: 1 or SEQ ID NO: 2. As discussed in the examples, SEQ ID NOs: 1 and 2 are recombinant Cas9 nucleic acid sequences that are codon-optimized for increased expression of Cas9 in human liver tissue and cells.

SEQ ID NO: 1 and SEQ ID NO: 2 contain nuclear localization sequences followed by a TGA stop codon shown in bolded text below. In certain embodiments, the recombinant Cas9 sequence sequences can be modified to include no nuclear localization sequence, or alternative nuclear localization sequences, or to include an alternative stop codon. In certain embodiments, the recombinant Cas9 sequence are at least 95%, at least 96%, at least 97%, at least 98%, at least 99%, or at least 99.5% identical to the sequence of SEQ ID NO: 1 or SEQ ID NO: 2 without the nuclear localization site or TGA stop codon.

Exemplary nucleic acids can be prepared by cloning techniques, or can be generated synthetically. Examples of appropriate cloning and sequencing techniques, and instructions sufficient to direct persons of skill through many cloning exercises are known (see, e.g., Sambrook et al. (Molecular Cloning: A Laboratory Manual, 4$^{th}$ ed, Cold Spring Harbor, N.Y., 2012) and Ausubel et al. (In Current Protocols in Molecular Biology, John Wiley & Sons, New York, through supplement 104, 2013). Product information from manufacturers of biological reagents and experimental equipment also provide useful information. Such manufacturers include the SIGMA Chemical Company (Saint Louis, Mo.), R&D Systems (Minneapolis, Minn.), Pharmacia Amersham (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersburg, Md.), Fluka Chemica-Biochemika Analytika (Fluka Chemie AG, Buchs, Switzerland), Invitrogen (Carlsbad, Calif.), and Applied Biosystems (Foster City, Calif.).

Nucleic acids can also be prepared by amplification methods. Amplification methods include polymerase chain reaction (PCR), the ligase chain reaction (LCR), the transcription-based amplification system (TAS), the self-sustained sequence replication system (3SR). A wide variety of cloning methods, host cells, and in vitro amplification methodologies are well known to persons of skill.

III. Cas9/CRISPR

Clustered regularly interspaced short palindromic repeat (CRISPR) RNA-guided adaptive immune systems that protect bacteria and archaea from infection by viruses have been repurposed for genome engineering in a wide variety of cell types and multicellular organisms. CRISPRs are DNA loci containing short repetitions of base sequences. Each repetition is followed by short segments of spacer DNA from previous exposures to a virus. CRISPRs are often associated with Cas genes. By introducing plasmids containing a Cas gene and specifically constructed CRISPRs into eukaryotic cells, the eukaryotic genome can be cut at any desired position. The Cas9 nuclease for targeted genome editing can include fused nuclear localization signals (NLSs) to a recombinant Cas9 nucleic acid sequence for increased Cas9 expression in human liver. This Cas9 sequence can be co-expressed with plasmids expressing the tracrRNA and a crRNA-guide, or a single chimeric guide RNA (gRNA).

Provided herein is a CRISPR/Cas9 system for tissue specific gene editing and gene expression. In an embodiment, the targeted tissue is the human liver.

A variety of clones containing functionally equivalent nucleic acids can be constructed, such as nucleic acids which differ in sequence but which encode the same Cas9 amino acid sequence. Silent mutations in the coding sequence result from the degeneracy (i.e., redundancy) of the genetic code, whereby more than one codon can encode the same amino acid residue. Thus, for example, leucine can be encoded by CTT, CTC, CTA, CTG, TTA, or TTG; serine can be encoded by TCT, TCC, TCA, TCG, AGT, or AGC; asparagine can be encoded by AAT or AAC; aspartic acid can be encoded by GAT or GAC; cysteine can be encoded by TGT or TGC; alanine can be encoded by GCT, GCC, GCA, or GCG; glutamine can be encoded by CAA or CAG; tyrosine can be encoded by TAT or TAC; and isoleucine can be encoded by ATT, ATC, or ATA. Tables showing the standard genetic code can be found in various sources (see, for example, Stryer, 1988, Biochemistry, 3$^{rd}$ Edition, W.H. Freeman and Co., NY).

Classic codon optimization introduces synonymous codon substitutions to better match the exogenous gene's codon usage to the codon usage preference of the host. This older methodology assumes codon usage bias of the host to be a proxy for steady state tRNA levels (see Quax et al. Mol Cell, 2015, included herein by reference in its entirety.) Codon optimization is routinely successful for prokaryotes and unicellular eukaryotes, but has been historically less successful in multicellular eukaryotes. Optimization for multicellular organisms has not previously considered the tissue in which the gene will be expressed.

In contrast, the codon optimization methodology used herein in the creation of a recombinant Cas9 nucleic acid molecule introduces structural changes and modifies sequence motifs to optimize mRNA free energy, mRNA secondary structure, and RNA instability motifs (e.g. cryptic splice sites, polymerase slippage, etc.)

Based on the genetic code, nucleic acid sequences coding for Cas9 can be generated. In some examples, such a sequence is optimized for expression in a host cell, such as a hepatocyte. Codon preferences and codon usage tables for a particular species can be used to engineer recombinant Cas9 nucleic acid molecules for protein expression in liver cells or tissue (such as a nucleic acid molecule having at least 95%, at least 96%, at least 97%, at least 98%, at least 99% or 100% sequence identity to SEQ ID NO: 1 or 2).

In one example, the recombinant Cas9 nucleic acid molecule (such as a nucleic acid molecules the at least 95% sequence identity to SEQ ID NO: 1 or 2) can be inserted into a vector. In one embodiment, vectors are used for expression in humans. Exemplary promoters for expression in mammalian cells include CMV, EF1a, SV40, PGK1, UBc, human beta actin, CAG, and others. Promoters can be tissue specific, providing enhanced promoter activity in certain cell types. In an embodiment, a liver specific promoter is the Hepatic Combinatorial Bundle (HCB) promoter (SEQ ID NO: 8).

The recombinant Cas9 nucleic acid molecule (such as a nucleic acid molecule with at least 95% sequence identity to SEQ ID NO: 1 or 2) can be expressed in a variety of liver cell types, including hepatic stellate cells, sinusoidal endothelial cells, phagocytic kuppfer cells, and parenchymal hepatocytes.

The disclosed recombinant Cas9 nucleic acid molecules (such as a nucleic acid molecules the at least 95% sequence identity to SEQ ID NO: 1 or 2), can be used in a CRISPR/Cas9 system to modulate (e.g., increase or decrease) expression of one or more target genes. Such methods can be performed in vitro (such as in cell culture), or in vivo (such as in an organism, embryo, or mammal).

The CRISPR/Cas9 system which utilizes the recombinant Cas9 nucleic acid molecule (such as a nucleic acid molecule with at least 95% sequence identity to SEQ ID NO: 1 or 2) can be used for gene editing in a cell, such as a liver cell. In addition, the recombinant Cas9 nucleic acid molecules can be used in combination with commercially available kits to design and develop vectors that include CRISPR/Cas9 genome editing materials for manipulating a specific target (e.g., those from Origene, Rockville, Md., from Addgene, Cambridge, Mass., such as the Church Lab CRISPR Plasmids, and from Life Technologies, Gaithersburg, Md., such as the GeneArt® CRISPR Nuclease Vector Kit).

The CRISPR/Cas9 system provided herein typically includes two general components: (1) the recombinant Cas9 nucleic acid molecule (such as a nucleic acid molecule with at least 95% sequence identity to SEQ ID NO: 1 or 2), whose expression can be driven by a promoter, such as HCB, and (2) single guide nucleic acid molecule, such as RNA (sgRNA or gRNA), which is operably linked downstream of a target sequence and upstream of a promoter (such as the HCB promoter). When introduced into cells (for example as part of a single vector or plasmid or divided into multiple vectors or plasmids), the guide nucleic acid molecule guides the Cas9 protein encoded by the recombinant Cas9 nucleic acid molecule to the locus and Cas9 will cut the target site. Using this system, DNA sequences within the endogenous genome and their functional outputs are easily edited or modulated.

One or more genes can be targeted by the disclosed methods, such as at least 1, at least 2, at least 3, at least 4 or at least 5 different genes or genetic elements in the organism, such as 1, 2, 3, 4, 5, 6, 7, 8, 9 or 10 different genes. In certain embodiments, the targeted genes encode proteins produced in the liver. In certain embodiments, the targeted genetic elements are regulatory elements controlling expression of proteins produced in the liver. In one example, the gene is associated with a liver associated disease or disorder, such as an inherited disease (e.g., hemochromatosis and Alpha-1 Antitrypsin Deficiency, Hemophilia A, hemophilia B.)

IV. Recombinant Vectors and Therapeutic Modalities

Viral vectors can also be prepared that include recombinant Cas9 nucleic acid molecule (such as a nucleic acid molecule with at least 95% sequence identity to SEQ ID NO: 1 or 2). Exemplary viral vectors include polyoma, SV40, adenovirus, vaccinia virus, adeno-associated virus (AAV), herpes viruses including HSV and EBV, Sindbis viruses, alphaviruses and retroviruses of avian, murine, and human origin. Baculovirus (*Autographa californica* multinuclear polyhedrosis virus; AcMNPV) vectors can be used and obtained from commercial sources. Other suitable vectors include retrovirus vectors, orthopox vectors, avipox vectors, fowlpox vectors, capripox vectors, suipox vectors, adenoviral vectors, herpes virus vectors, alpha virus vectors, baculovirus vectors, Sindbis virus vectors, vaccinia virus vectors and poliovirus vectors. Specific exemplary vectors are poxvirus vectors such as vaccinia virus, fowlpox virus and a highly attenuated vaccinia virus (MVA), adenovirus, baculovirus and the like. Pox viruses of use include orthopox, suipox, avipox, and capripox virus. Orthopox include vaccinia, ectromelia, and raccoon pox. One example of an orthopox of use is vaccinia. Avipox includes fowlpox, canary pox and pigeon pox. Capripox include goatpox and sheeppox. In one example, the suipox is swinepox. Other viral vectors that can be used include other DNA viruses such as herpes virus and adenoviruses, and RNA viruses such as retroviruses and polio.

The recombinant vectors disclosed herein (for example, a recombinant AAV vector) can be used in several different therapeutic applications, depending on the guide RNAs of the CRISPR/Cas9 system encoded by the recombinant vector(s). Guide RNAs and the recombinant Cas9 nucleic acid molecule (such as a nucleic acid molecule with at least 95% sequence identity to SEQ ID NO: 1 or 2) can be combined on a single cassette or vector, or can be contained on individual vectors. In some embodiments, an additional vector encoding rare, or rate limiting tRNAs, is used in treatment of a disorder relating to proteins expressed in the liver, or a liver disorder in conjunction with the recombinant Cas9 nucleic acid molecule.

In certain embodiments, a recombinant AAV vector can include a tissue specific promoter, such a liver specific promoter. An exemplary promoter is HNF1-shortABP-SynO-TSS (also called Hepatic Combinatorial Bundle, or HCB) (SEQ ID NO: 8)

GTTAATCATTAAGTCGTTAATTTTTGTGGCCCTTGCGATGTTTGCTCTGG

TTAATAATCTCAGGACAAACAGAGGTTAATAATTTTCCAGATCTCTCTGA

GCAATAGTATAAAAGGCCAGCAGCAGCCTGACCACATCTCATCCTC

Figure 4:
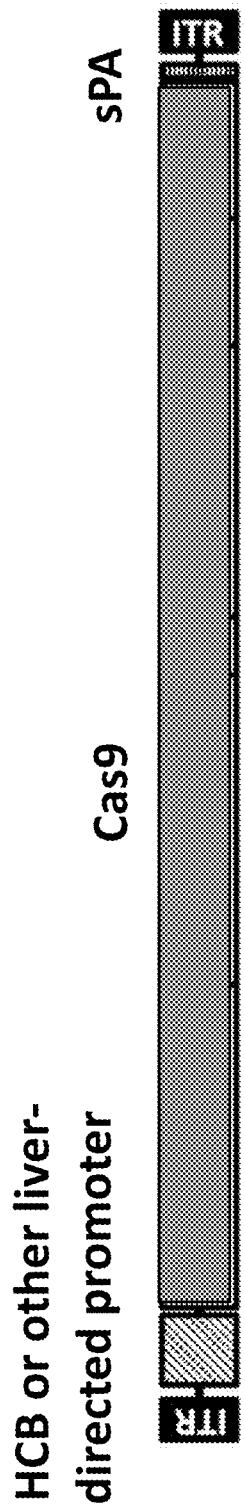
FIG. 4 is an illustration of an example Cas9 AAV cassette, including a Hepatic Combinatorial Bundle (HCB) promoter, recombinant Cas9 nucleic acid with codon-optimization for expression in human liver, left and right inverted terminal repeats (ITR), and synthetic polyadenylation (SpA) signal.

In certain embodiments, an exemplary AAV cassette has the following structure as illustrated in FIG. 4:
(5'AAV2 ITR)-(HCB Promoter)-(recombinant Cas9 nucleic acid molecule)-(poly adenylation signal)-(3'AAV2 ITR)

In certain embodiments, recombinant vectors are used in the treatment of diseases or disorders related to aberrant proteins, or aberrant protein expression of proteins expressed in the liver. In certain embodiments, recombinant vectors are used in the treatment of liver diseases or disorders, or disorders affecting proteins expressed in the liver. The recombinant Cas9 nucleic acid molecule (such as a nucleic acid molecule with at least 95% sequence identity to SEQ ID NO: 1 or 2) and target guide RNAs encoded by one or more recombinant vectors are administered to a subject in need thereof for the use in treating a liver disorder, for example a hereditary liver disorder, by CRIPSR gene-editing. In certain embodiments, guide RNAs can be designed to target aberrant gene expression contributing to liver disorders or disorders relating to proteins expressed in the liver by targeting the regulatory elements of known genes, for example those listed herein. In certain embodiments, guide RNAs can be designed to target abnormalities, for example SNPs, within the genes themselves that are contributing to a liver disorder, or disease related to proteins expressed in the liver. In certain embodiments, multiple guide RNAs targeting the same gene, or regulatory elements, or different genes and regulatory elements can be used in the treatment of a subject in need thereof.

In certain embodiments, the uses are for the treatment of hereditary hemochromatosis (HH), a major disorder of iron overload, Wilson's disease, a genetic disorder of copper overload, and alpha1-antitrypsin (a1-AT) deficiency. In certain embodiments, the protein is human Alpha1-antitrypsin (a1-AT, Accession: P01009.3), HFE protein (Accession NP_000401.1 or Q30201), or hepatic protein ATP7B (Accession P35670.4) or variants with greater than 50, 60, 70, 80, 90, 95, or 95 sequence identity or similarity.

In certain embodiments, the uses are for the treatment of Hemophilia A using a nucleic acid that encodes a guide RNA targeting Factor VIII (Accession: FN811132.1) or variants with greater than 50, 60, 70, 80, 90, 95, or 95 sequence identity or similarity.

In certain embodiments, the uses are for the treatment of Hemophillia B using a nucleic acid that encodes a guide RNA targeting Factor IX (Accession: K02402.1) or variants with greater than 50, 60, 70, 80, 90, 95, or 95 sequence identity or similarity.

In certain embodiments, the use is for the treatment of hypercholesterolaemia using a nucleic acid that encodes for a guide RNA targeting human phenylalanine hydroxylase (Accession: P00439.1) or variants with greater than 50, 60, 70, 80, 90, 95, or 95 sequence identity or similarity.

In certain embodiments, the use is for the treatment of Type 1 tyrosinemia using a nucleic acid that encodes a guide RNA targeting human fumarylacetoacetate hydrolase (Accession: P16930.2) or variants with greater than 50, 60, 70, 80, 90, 95, or 95 sequence identity or similarity.

In certain embodiments, the use is for the treatment of Type 2 tyrosinemia using a nucleic acid that encodes for a guide RNA targeting human tyrosine aminotransferase (Accession: P17735.1) or variants with greater than 50, 60, 70, 80, 90, 95, or 95 sequence identity or similarity.

In certain embodiments, the use is for the treatment of homocystinuria and hyperhomocysteinemia using a nucleic acid that encodes a guide RNA targeting human methylenetetrahydrofolate reductase (Accession: P42898.3) or variants with greater than 50, 60, 70, 80, 90, 95, or 95 sequence identity or similarity.

In certain embodiments, the use is for the treatment of hyperlipidemia and hypercholesterolemia using a nucleic acid that encodes a guide RNA targeting human medium chain acyl-CoA dehydrogenase (Accession: P11310.1) or variants with greater than 50, 60, 70, 80, 90, 95, or 95 sequence identity or similarity.

In certain embodiments, the use is for the treatment of Galactosemia using a a nucleic acid that encodes a guide RNA targeting human galactose-1-phosphate uridyl transferase (Accession: P07902.3) or variants with greater than 50, 60, 70, 80, 90, 95, or 95 sequence identity or similarity.

In certain embodiments, the use is for the treatment of Lesch-Nyhan syndrome using a nucleic acid that encodes a guide RNA targeting human hypoxanthine phosphoribosyl-transferase (Accession: P00492.2) or variants with greater than 50, 60, 70, 80, 90, 95, or 95 sequence identity or similarity.

In certain embodiments, the use is for the treatment of Gaucher disease using a nucleic acid that encodes a guide RNA targeting human cerebrosidase (Accession: P07602.2, Accession: P04062.3) or variants with greater than 50, 60, 70, 80, 90, 95, or 95 sequence identity or similarity.

In certain embodiments, the use is for the treatment of Tay-Sachs disease using a a nucleic acid that encodes a guide RNA targeting human beta-hexosaminidase A (Accession: P06865.2) or variants with greater than 50, 60, 70, 80, 90, 95, or 95 sequence identity or similarity.

In certain embodiments, the use is for the treatment of Fabry disease using a nucleic acid that encodes a guide RNA targeting human α-galactosidase (Accession: P06280.1) or variants with greater than 50, 60, 70, 80, 90, 95, or 95 sequence identity or similarity.

In certain embodiments, the use is for the treatment of Hunter syndrome using a nucleic acid that encodes a guide RNA targeting human iduronate sulphatase (Accession: P22304.1) or variants with greater than 50, 60, 70, 80, 90, 95, or 95 sequence identity or similarity.

In certain embodiments, the use is for the treatment of glycogen storage disease type Ia using a nucleic acid that encodes a guide RNA targeting human glucose-6-phosphatase (Accession: P35575.2) or variants with greater than 50, 60, 70, 80, 90, 95, or 95 sequence identity or similarity.

In certain embodiments, the use is for the treatment of ammonia metabolism using a nucleic acid that encodes a guide RNA targeting human ornithine transcarbamylase (Accession: P00480.3) or variants with greater than 50, 60, 70, 80, 90, 95, or 95 sequence identity or similarity.

In certain embodiments, the use is for the treatment of phenylketonuria using a nucleic acid that encodes a guide RNA targeting human low-density lipoprotein receptor (Accession: P01130.1) or variants with greater than 50, 60, 70, 80, 90, 95, or 95 sequence identity or similarity.

In certain embodiments, the use is for the treatment of propionic acidemia using a nucleic acid that encodes a guide RNA targeting human propionyl-coenzyme A carboxylase, either PCCA and/or PCCB (Accession: P05166.3 beta, NP_000273.2 alpha, NP_001121164.1 alpha) or variants with greater than 50, 60, 70, 80, 90, 95, or 95 sequence identity or similarity.

Recombinant vectors comprising the recombinant Cas9 nucleic acid molecule (such as a nucleic acid molecule with at least 95% sequence identity to SEQ ID NO: 1 or 2) and/or guide RNAs disclosed herein can be delivered to the liver via the hepatic artery, the portal vein, or intravenously to yield therapeutic levels of therapeutic proteins, including decreased or increased protein levels, or to correct coding errors in proteins produced in the liver which result in aberrant proteins. The vector is preferably suspended in a physiologically compatible carrier, may be administered to a human or non-human mammalian patient. Suitable carriers can be selected in view of the indication for which the transfer virus is directed. For example, one suitable carrier includes saline, which may be formulated with a variety of buffering solutions (e.g., phosphate buffered saline). Other exemplary carriers include sterile saline, lactose, sucrose, calcium phosphate, gelatin, dextran, agar, pectin, sesame oil, and water.

Optionally, the compositions of the disclosure may contain other pharmaceutically acceptable excipients, such as preservatives, or chemical stabilizers. Suitable exemplary preservatives include chlorobutanol, potassium sorbate, sorbic acid, sulfur dioxide, propyl gallate, the parabens, ethyl vanillin, glycerin, phenol, and parachlorophenol. Suitable chemical stabilizers include gelatin and albumin.

The recombinant viral vectors comprising the recombinant Cas9 nucleic acid molecule (such as a nucleic acid molecule with at least 95% sequence identity to SEQ ID NO: 1 or 2) and/or encoding selected guide RNAs are administered in sufficient amounts to express the recombinant Cas9 nucleic acid molecule and selected guide RNAs to provide a therapeutic benefit without undue adverse effects, or with medically acceptable physiological effects, which can be determined by those skilled in the medical arts. Conventional and pharmaceutically acceptable routes of administration include, but are not limited to, direct delivery to a desired organ (e.g., the liver (optionally via the hepatic artery) or lung), oral, inhalation, intranasal, intratracheal, intraarterial, intraocular, intravenous, intramuscular, subcutaneous, intradermal, and other parental routes of administration. Routes of administration may be combined, if desired.

Dosages of the recombinant viral vectors will depend primarily on factors such as the condition being treated, the age, weight and health of the patient, and may thus vary among patients. For example, a therapeutically effective human dosage of the viral vector is generally in the range of from about 0.1 ml to about 100 ml of solution containing concentrations of from about $1 \times 10^9$ to $1 \times 10^{16}$ genomes virus vector.

Recombinant viral vectors of the disclosure provide an efficient gene editing tool and can deliver a selected Cas9 and guide RNA(s) to a selected host cell in vivo or ex vivo. In one embodiment, the vectors disclosed herein and the cells are mixed ex vivo; the infected cells are cultured using conventional methodologies; and the transduced cells are re-infused into the patient.

In certain embodiments, recombinant viral vectors are generated in cultured cells. A person of ordinary skill in the art would recognize methods of infecting mammalian cell lines with the recombinant viral vector of the present disclosure and maintain the cells in culture allowing for translation of the viral genome and replication of the virus.

V. Kits

Kits are provided that include one or more of the disclosed recombinant Cas9 nucleic acid molecules, vectors including such recombinant Cas9 nucleic acid molecules, and recombinant cells including such nucleic acid molecules or vectors. In some examples, such components are in separate vials.

In some examples, the recombinant Cas9 nucleic acid molecule is part of a vector, such as a plasmid or viral vector. In some examples, the recombinant Cas9 nucleic acid molecule (which may be part of a vector) is present in a cell (such as a bacteria, yeast, or mammalian cell, such as *E. coli*). In some examples, the recombinant Cas9 nucleic acid molecule includes an operably linked promoter, such as HCB, CMV or U6.

In some examples, the disclosed kits further include cell culture or growth media, such as media appropriate for growing bacterial, plant, insect, or mammalian cells.

In some examples, the disclosed kits further include a guide nucleic acid molecule (guide RNA) specific for a target nucleic acid molecule, such as a target whose temporal or spatial expression is desired to be controlled. The guide RNA molecule can be part of a vector, such as a plasmid or viral vector.

EXAMPLES

Example 1: Target Specific Codon Optimization

Figure 3A:
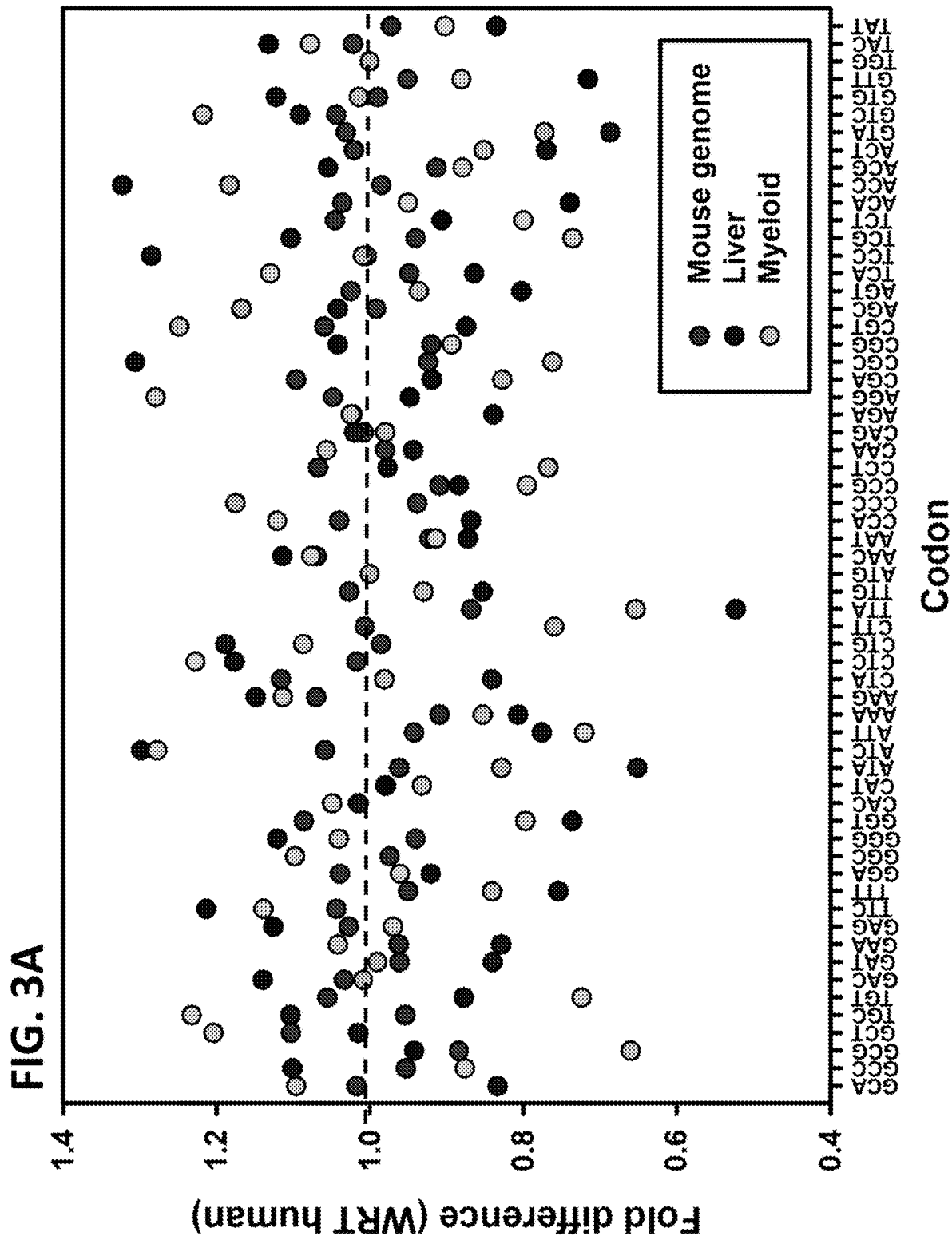

The nucleic acid codons contain redundancies such that distinct codons can encode the same amino acid. FIG. 1A shows the codon frequencies across the human genome. Each codon requires a complimentary tRNA. tRNA contents vary in both proportion and quantity among cell types (see FIG. 1B). Moreover, tRNA content and codon usage vary among tissue types (Dittmar et al. PloS Genet. 2006 December; 2(12):e221. PMID: 17194224. Incorporated herein by reference in its entirety). Just as codon frequencies vary amongst tissues and cell types, they vary among organisms (FIG. 2A-FIG. 2C). Codon frequencies are actually more similar between the entire mouse genome and the entire human genome than comparisons between the codon frequencies of the entire human genome compared to the codon frequencies of the human liver alone, or human myeloid cells alone (FIG. 3).

Using this information about the variance in codon and tRNA frequencies among organisms, tissues and cell types. Algorithms can be created to codon-optimize sequences for maximized expression in a specific target. In designing and testing codon-optimization the same algorithm was used for whole human, liver, and myeloid optimization. The optimization allowed for structural and cis-acting sequence motifs to be controlled between variants. Utilization of these liver optimized sequences allows for interrogation of the impact from codon bias only and for controlling for structural and sequence motif changes.

Example 2: Recombinant Cas9 Sequences for Improved Expression in Human Tissues

Using an algorithm constructed as described above a recombinant Cas9 nucleic acid molecules with a sequence that provides for increased expression in liver cells and tissue compared to native Cas9 sequence can be created. The recombinant Cas9 nucleic acid molecule can be delivered to human liver tissue, for example by an adeno-associated virus (AAV) vector. A cassette for producing such an AAV vector is shown in FIG. 4 which includes a Hepatic Combinatorial Bundle (HCB) promoter, the recombinant Cas9 nucleic acid molecule, left and right inverted terminal repeats (ITR), and synthetic polyadenylation (SpA) signal.

The sequence of the recombinant Cas9 nucleic acid molecule that provides for increased expression in liver cells and tissue compared to native Cas9 sequence was created using algorithms which take into consideration codon usage frequencies for human liver as shown in FIG. 5. In addition to optimizing sequences for target codon frequencies, sequence optimization can include targets for CG content or inclusion or elimination of CpG dinucleotides, consideration of tRNA frequencies, secondary structure and other factors.

For reference, an example of Cas9 protein sequence is provided as SEQ ID NO: 9:

MDKKYSIGLDIGTNSVGWAVITDEYKVPSKKFKVLGNTDRHSIKKNLIGA
LLFDSGETAEATRLKRTARRRYTRRKNRICYLQEIFSNEMAKVDDSFFHR
LEESFLVEEDKKHERHPIFGNIVDEVAYHEKYPTIYHLRKKLVDSTDKAD
LRLIYLALAHMIKFRGHFLIEGDLNPDNSDVDKLFIQLVQTYNQLFEENP
INASGVDAKAILSARLSKSRRLENLIAQLPGEKKNGLFGNLIALSLGLTP
NFKSNFDLAEDAKLQLSKDTYDDDLDNLLAQIGDQYADLFLAAKNLSDAI
LLSDILRVNTEITKAPLSASMIKRYDEHHQDLTLLKALVRQQLPEKYKEI
FFDQSKNGYAGYIDGGASQEEFYKFIKPILEKMDGTEELLVKLNREDLLR
KQRTFDNGSIPHQIHLGELHAILRRQEDFYPFLKDNREKIEKILTFRIPY
YVGPLARGNSRFAWMTRKSEETITPWNFEEVVDKGASAQSFIERMTNFDK
NLPNEKVLPKHSLLYEYFTVYNELTKVKYVTEGMRKPAFLSGEQKKAIVD
LLFKTNRKVTVKQLKEDYFKKIECFDSVEISGVEDRFNASLGTYHDLLKI
IKDKDFLDNEENEDILEDIVLTLTLFEDREMIEERLKTYAHLFDDKVMKQ
LKRRRYTGWGRLSRKLINGIRDKQSGKTILDFLKSDGFANRNFMQLIHDD
SLTFKEDIQKAQVSGQGDSLHEHIANLAGSPAIKKGILQTVKVVDELVKV
MGRHKPENIVIEMARENQTTQKGQKNSRERMKRIEEGIKELGSQILKEHP
VENTQLQNEKLYLYYLQNGRDMYVDQELDINRLSDYDVDHIVPQSFLKDD
SIDNKVLTRSDKNRGKSDNVPSEEVVKKMKNYWRQLLNAKLITQRKFDNL
TKAERGGLSELDKAGFIKRQLVETRQITKHVAQILDSRMNTKYDENDKLI
REVKVITLKSKLVSDFRKDFQFYKVREINNYHHAHDAYLNAVVGTALIKK
YPKLESEFVYGDYKVYDVRKMIAKSEQEIGKATAKYFFYSNIMNFFKTEI
TLANGEIRKRPLIETNGETGEIVWDKGRDFATVRKVLSMPQVNIVKKTEV
QTGGFSKESILPKRNSDKLIARKKDWDPKKYGGFDSPTVAYSVLVVAKVE
KGKSKKLKSVKELLGITIMERSSFEKNPIDFLEAKGYKEVKKDLIIKLPK
YSLFELENGRKRMLASAGELQKGNELALPSKYVNFLYLASHYEKLKGSPE
DNEQKQLFVEQHKHYLDEIIEQISEFSKRVILADANLDKVLSAYNKHRDK
PIREQAENIIHLFTLTNLGAPAAFKYFDTTIDRKRYTSTKEVLDATLIHQ
SITGLYETRIDLSQLGGD

An example recombinant Cas9 sequence that provides for increased expression in liver cells and tissue compared to native Cas9 sequence is provided by SEQ ID NO: 1. The sequence includes CpG dinucleotides and the Cas9 sequence is followed by a nuclear localization site and stop codon.

(SEQ ID NO: 1)
ATGGACAAGAAGTACTCCATCGGCCTGGACATCGGGACCAACAGCGTGGG

CTGGGCCGTGATCACCGACGAGTACAAGGTGCCCTCCAAGAAGTTCAAGG

TGCTGGGGAACACCGACAGACACAGCATCAAGAAGAACCTGATCGGCGCC

CTGCTGTTCGACTCCGGAGAAACCGCTGAGGCTACCCGCCTGAAGAGAAC

CGCTCGCCGGAGGTACACCAGACGCAAGAACAGGATCTGCTACCTGCAGG

AGATCTTCTCCAACGAGATGGCCAAGGTGGACGACTCCTTCTTCCACCGG

CTGGAGGAGAGCTTCCTGGTGGAGGAGGACAAGAAGCACGAGAGGCACCC

CATCTTCGGCAACATCGTGGACGAGGTGGCCTACCACGAGAAGTACCCCA

CCATCTACCACCTGAGGAAGAAGCTGGTGGACTCCACCGACAAGGCCGAC

CTGAGACTGATCTACCTGGCCCTGGCCCACATGATCAAGTTCCGCGGCCA

CTTCCTGATCGAGGGGGACCTGAACCCCGACAACAGCGACGTGGACAAGC

TGTTCATCCAGCTGGTGCAGACCTACAACCAGCTGTTCGAGGAGAACCCC

ATCAACGCTTCCGGAGTGGACGCTAAGGCTATCCTGAGCGCCAGACTGTC

CAAGAGCCGGAGGCTGGAGAACCTGATCGCCCAGCTGCCCGGCGAGAAGA

AGAACGGCCTGTTCGGGAACCTGATCGCCCTGTCCCTGGGGCTGACCCCC

AACTTCAAGAGCAATTTCGACCTGGCCGAGGACGCCAAGCTGCAGCTGTC

CAAGGACACCTACGACGACGACCTGGACAACCTGCTGGCCCAGATCGGCG

ACCAGTACGCCGACCTGTTCCTGGCCGCCAAGAACCTGTCCGACGCCATC

CTGCTGAGCGACATCCTGCGCGTGAACACCGAGATCACCAAGGCCCCCCT

GTCCGCCAGCATGATCAAGAGATACGACGAGCACCACCAGGACCTGACCC

TGCTGAAGGCCCTGGTGCGCCAGCAGCTGCCCGAGAAGTACAAGGAGATC

TTCTTCGACCAGAGCAAGAACGGATACGCTGGATACATCGACGGAGGAGC

CTCCCAGGAGGAGTTCTACAAGTTCATCAAGCCCATCCTGGAGAAGATGG

ACGGCACCGAGGAGCTGCTGGTGAAGCTGAACCGGGAGGACCTGCTGAGG

AAGCAGAGAACCTTCGACAACGGCTCCATCCCCCACCAGATCCACCTGGG

GGAGCTGCACGCCATCCTGAGACGCCAGGAGGACTTCTACCCCTTCCTGA

AGGACAACAGGGAGAAGATCGAGAAGATCCTGACCTTCAGAATCCCCTAC

TACGTGGGACCACTGGCTAGGGGAAACTCCAGATTCGCCTGGATGACCCG

GAAGAGCGAGGAAACCATCACCCCCTGGAACTTCGAGGAGGTGGTGGACA

AGGGAGCTTCCGCCCAGAGCTTCATCGAGAGGATGACCAACTTCGACAAG

AACCTGCCCAACGAGAAGGTGCTGCCCAAGCACTCCCTGCTGTACGAGTA

CTTCACCGTGTACAACGAGCTGACCAAGGTGAAGTACGTGACCGAGGGCA

TGAGAAAGCCCGCCTTCCTGAGCGGGGAGCAGAAGAAGGCCATCGTGGAC

CTGCTGTTCAAGACCAACCGCAAGGTGACCGTGAAGCAGCTGAAGGAGGA

CTACTTCAAGAAGATCGAGTGCTTCGACTCCGTGGAGATCAGCGGAGTGG

AGGACCGCTTCAACGCTTCCCTGGGGACCTACCACGACCTGCTGAAGATC

ATCAAGGACAAGGACTTCCTGGACAACGAGGAGAACGAGGACATCCTGGA

GGACATCGTGCTGACCCTGACCCTGTTCGAGGACCGCGAGATGATCGAGG

```
AGCGGCTGAAGACCTACGCCCACCTGTTCGACGACAAGGTCATGAAGCAG

CTGAAGCGGAGGAGATACACCGGATGGGGGCGCCTGAGCAGAAAGCTGAT

CAACGGCATCCGGGACAAGCAGTCCGGGAAGACCATCCTGGACTTCCTGA

AGAGCGACGGCTTCGCCAACAGGAACTTCATGCAGCTGATCCACGACGAC

TCCCTGACCTTCAAGGAGGACATCCAGAAGGCTCAGGTGTCCGGACAGGG

GGACAGCCTGCACGAGCACATCGCTAACCTGGCTGGCAGCCCCGCCATCA

AGAAGGGGATCCTGCAGACCGTGAAGGTGGTGGACGAGCTGGTGAAGGTC

ATGGGCAGGCACAAGCCCGAGAACATCGTGATCGAGATGGCCAGAGAGAA

CCAGACCACCCAGAAGGGGCAGAAGAACTCCCGCGAGCGGATGAAGAGGA

TCGAGGAGGGCATCAAGGAGCTGGGGAGCCAGATCCTGAAGGAGCACCCC

GTGGAGAACACCCAGCTGCAGAACGAGAAGCTGTACCTGTACTACCTGCA

GAACGGCCGCGACATGTACGTGGACCAGGAGCTGGACATCAACCGGCTGT

CCGACTACGACGTGGACCACATCGTGCCCCAGTCCTTCCTGAAGGACGAC

AGCATCGACAACAAGGTGCTGACCCGCAGCGACAAGAACCGGGGGAAGTC

CGACAACGTGCCCAGCGAGGAGGTGGTGAAGAAGATGAAGAACTACTGGC

GCCAGCTGCTGAACGCCAAGCTGATCACCCAGCGCAAGTTCGACAACCTG

ACCAAGGCTGAGAGAGGAGGGCTGTCCGAGCTGGACAAGGCCGGCTTCAT

CAAGAGGCAGCTGGTGGAAACCAGACAGATCACCAAGCACGTGGCCCAGA

TCCTGGACAGCCGGATGAACACCAAGTACGACGAGAACGACAAGCTGATC

AGGGAGGTGAAGGTCATCACCCTGAAGTCCAAGCTGGTGAGCGACTTCCG

CAAGGACTTCCAGTTCTACAAGGTGCGGGAGATCAACAACTACCACCACG

CCCACGACGCTTACCTGAACGCTGTGGTGGGAACCGCCCTGATCAAGAAG

TACCCCAAGCTGGAGTCCGAGTTCGTGTACGGGGACTACAAGGTGTACGA

CGTGCGCAAGATGATCGCCAAGTCCGAGCAGGAGATCGGCAAGGCCACCG

CCAAGTACTTCTTCTACAGCAACATCATGAACTTCTTCAAGACCGAGATC

ACCCTGGCCAACGGCGAGATCAGGAAGCGCCCCCTGATCGAAACCAACGG

CGAAACCGGAGAGATCGTGTGGGACAAGGGGAAGAGACTTCGCTACCGTGC

GGAAGGTGCTGTCCATGCCCCAGGTGAACATCGTGAAGAAGACCGAGGTG

CAGACCGGCGGGTTCTCCAAGGAGAGCATCCTGCCCAAGAGGAACAGCGA

CAAGCTGATCGCCAGAAAGAAGGACTGGGACCCCAAGAAGTACGGAGGAT

TCGACTCCCCAACCGTGGCTTACAGCGTGCTGGTGGTGGCCAAGGTGGAG

AAGGGCAAGTCCAAGAAGCTGAAGAGCGTGAAGGAGCTGCTGGGGATCAC

CATCATGGAGCGGTCCAGCTTCGAAGAACCCCATCGACTTCCTGGAGG

CCAAGGGCTACAAGGAGGTGAAGAAGGACCTGATCATCAAGCTGCCCAAG

TACAGCCTGTTCGAGCTGGAGAACGGAAGAAAGAGAATGCTGGCTTCCGC

CGGAGAGCTGCAGAAGGGAAACGAGCTGGCCCTGCCCAGCAAGTACGTGA

ACTTCCTGTACCTGGCCTCCCACTACGAGAAGCTGAAGGGCAGCCCCGAG

GACAACGAGCAGAAGCAGCTGTTCGTGGAGCAGCACAAGCACTACCTGGA

CGAGATCATCGAGCAGATCTCCGAGTTCAGCAAGCGCGTGATCCTGGCCG

ACGCCAACCTGGACAAGGTGCTGTCCGCCTACAACAAGCACAGGGACAAG
```

```
CCCATCAGAGAGCAGGCCGAGAACATCATCCACCTGTTCACCCTGACCAA

CCTGGGAGCTCCAGCTGCCTTCAAGTACTTCGACACCACCATCGACAGGA

AGAGATACACCAGCACCAAGGAGGTGCTGGACGCCACCCTGATCCACCAG

TCCATCACCGGGCTGTACGAAACCAGAATCGACCTGAGCCAGCTGGGAGG

CGACCCCAAGAAGAAGCGCAAGGTGTGA
```

Another example recombinant Cas9 sequence that provides for increased expression in liver cells and tissue compared to native Cas9 sequence is provided by SEQ ID NO: 2. The sequence does not includes CpG dinucleotides and the Cas9 sequence is followed by a nuclear localization site and stop codon.

```
                                        (SEQ ID NO: 2)
ATGGACAAGAAGTACTCCATTGGCCTGGACATTGGGACCAACTCTGTGGG

CTGGGCTGTGATCACAGATGAGTACAAGGTGCCCTCCAAGAAGTTCAAGG

TGCTGGGGAACACAGACAGACACAGCATCAAGAAGAACCTGATTGGAGCC

CTGCTGTTTGACTCTGGAGAAACAGCTGAGGCTACCAGGCTGAAGAGAAC

AGCTAGGAGGAGATACACCAGAAGAAAGAACAGGATCTGCTACCTGCAGG

AGATCTTCTCCAATGAGATGGCCAAGGTGGATGACTCCTTCTTCCACAGG

CTGGAGGAGAGCTTCCTGGTGGAGGAGGACAAGAAGCATGAGAGGCACCC

CATCTTTGGCAACATTGTGGATGAGGTGGCCTACCATGAGAAGTACCCCA

CCATCTACCACCTGAGGAAGAAGCTGGTGGACTCCACAGACAAGGCTGAC

CTGAGACTGATCTACCTGGCCCTGGCCCACATGATCAAGTTCAGAGGCCA

CTTCCTGATTGAGGGGGACCTGAACCCAGACAACTCTGATGTGGACAAGC

TGTTCATCCAGCTGGTGCAGACCTACAACCAGCTGTTTGAGGAGAACCCC

ATCAATGCTTCTGGAGTGGATGCTAAGGCTATCCTGTCTGCCAGACTGTC

CAAGAGCAGGAGGCTGGAGAACCTGATTGCCCAGCTGCCTGGGGAGAAGA

AGAATGGCCTGTTTGGGAACCTGATTGCCCTGTCCCTGGGGCTGACCCCC

AACTTCAAGAGCAATTTTGACCTGGCTGAGGATGCCAAGCTGCAGCTGTC

CAAGGACACCTATGATGATGACCTGGACAACCTGCTGGCCCAGATTGGAG

ACCAGTATGCTGACCTGTTCCTGGCTGCTAAGAACCTGTCTGATGCCATC

CTGCTGTCTGACATCCTGAGGGTGAACACAGAGATCACCAAGGCCCCCCT

GTCTGCCAGCATGATCAAGAGATATGATGAGCACCACCAGGACCTGACCC

TGCTGAAGGCCCTGGTGAGGCAGCAGCTGCCTGAGAAGTACAAGGAGATC

TTCTTTGACCAGAGCAAGAATGGATATGCTGGATACATTGATGGAGGAGC

CTCCCAGGAGGAGTTCTACAAGTTCATCAAGCCCATCCTGGAGAAGATGG

ATGGCACAGAGGAGCTGCTGGTGAAGCTGAACAGGGAGGACCTGCTGAGG

AAGCAGAGAACCTTTGACAATGGCTCCATCCCCCACCAGATCCACCTGGG

GGAGCTGCATGCCATCCTGAGAAGACAGGAGGACTTCTACCCCTTCCTGA

AGGACAACAGGGAGAAGATTGAGAAGATCCTGACCTTCAGAATCCCATAC

TATGTGGGACCACTGGCTAGGGGAAACTCCAGATTTGCCTGGATGACCAG

GAAGTCTGAGGAAACCATCACCCCCTGGAACTTTGAGGAGGTGGTGGACA

AGGGAGCTTCTGCCCAGAGCTTCATTGAGAGGATGACCAACTTTGACAAG
```

```
AACCTGCCCAATGAGAAGGTGCTGCCCAAGCACTCCCTGCTGTATGAGTA

CTTCACAGTGTACAATGAGCTGACCAAGGTGAAGTATGTGACAGAGGGCA

TGAGAAAGCCTGCCTTCCTGTCTGGGGAGCAGAAGAAGGCCATTGTGGAC

CTGCTGTTCAAGACCAACAGGAAGGTGACAGTGAAGCAGCTGAAGGAGGA

CTACTTCAAGAAGATTGAGTGCTTTGACTCTGTGGAGATCTCTGGAGTGG

AGGACAGATTCAATGCTTCCCTGGGGACCTACCATGACCTGCTGAAGATC

ATCAAGGACAAGGACTTCCTGGACAATGAGGAGAATGAGGACATCCTGGA

GGACATTGTGCTGACCCTGACCCTGTTTGAGGACAGAGAGATGATTGAGG

AGAGGCTGAAGACCTATGCCCACCTGTTTGATGACAAGGTCATGAAGCAG

CTGAAGAGGAGGAGATACACAGGATGGGGGAGGCTGAGCAGAAAGCTGAT

CAATGGCATCAGAGACAAGCAGTCTGGGAAGACCATCCTGGACTTCCTGA

AGTCTGATGGCTTTGCCAACAGGAACTTCATGCAGCTGATCCATGATGAC

TCCCTGACCTTCAAGGAGGACATCCAGAAGGCTCAGGTGTCTGGACAGGG

GGACAGCCTGCATGAGCACATTGCTAACCTGGCTGGCAGCCCTGCCATCA

AGAAGGGGATCCTGCAGACTGTGAAGGTGGTGGATGAGCTGGTGAAGGTC

ATGGGCAGGCACAAGCCTGAGAACATTGTGATTGAGATGGCCAGAGAGAA

CCAGACCACCCAGAAGGGGCAGAAGAACTCCAGAGAGGATGAAGAGGA

TTGAGGAGGGCATCAAGGAGCTGGGGAGCCAGATCCTGAAGGAGCACCCT

GTGGAGAACACCCAGCTGCAGAATGAGAAGCTGTACCTGTACTACCTGCA

GAATGGCAGAGACATGTATGTGGACCAGGAGCTGGACATCAACAGACTGT

CTGACTATGATGTGGACCACATTGTGCCCCAGTCCTTCCTGAAGGATGAC

AGCATTGACAACAAGGTGCTGACCAGATCTGACAAGAATAGGGGGAAGTC

TGACAATGTGCCCTCTGAGGAGGTGGTGAAGAAGATGAAGAACTACTGGA

GACAGCTGCTGAATGCCAAGCTGATCACCCAGAGAAAGTTTGACAACCTG

ACCAAGGCTGAGAGAGGAGGGCTGTCTGAGCTGGACAAGGCTGGCTTCAT

CAAGAGGCAGCTGGTGGAAACCAGACAGATCACCAAGCATGTGGCCCAGA

TCCTGGACAGCAGGATGAACACCAAGTATGATGAGAATGACAAGCTGATC

AGGGAGGTGAAGGTCATCACCCTGAAGTCCAAGCTGGTGTCTGACTTCAG

AAAGGACTTCCAGTTCTACAAGGTGAGAGAGATCAACAACTACCACCATG

CCCATGATGCTTACCTGAATGCTGTGGTGGGAACAGCCCTGATCAAGAAG

TACCCCAAGCTGGAGTCTGAGTTTGTGTATGGGGACTACAAGGTGTATGA

TGTGAGAAAGATGATTGCCAAGTCTGAGCAGGAGATTGGCAAGGCCACAG

CCAAGTACTTCTTCTACAGCAACATCATGAACTTCTTCAAGACAGAGATC

ACCCTGGCCAATGGGGAGATCAGGAAGAGACCCCTGATTGAAACCAATGG

GGAAACTGGAGAGATTGTGTGGGACAAGGGAAGAGACTTTGCTACAGTGA

GAAAGGTGCTGTCCATGCCCCAGGTGAACATTGTGAAGAAGACAGAGGTG

CAGACAGGGGGGTTCTCCAAGGAGAGCATCCTGCCCAAGAGGAACTCTGA

CAAGCTGATTGCCAGAAAGAAGGACTGGGACCCCAAGAAGTATGGAGGAT

TTGACTCCCCAACAGTGGCTTACTCTGTGCTGGTGGTGGCCAAGGTGGAG

AAGGGCAAGTCCAAGAAGCTGAAGTCTGTGAAGGAGCTGCTGGGGATCAC

CATCATGGAGAGATCCAGCTTTGAGAAGAACCCCATTGACTTCCTGGAGG

CCAAGGGCTACAAGGAGGTGAAGAAGGACCTGATCATCAAGCTGCCCAAG

TACAGCCTGTTTGAGCTGGAGAATGGAAGAAAGAGAATGCTGGCTTCTGC

TGGAGAGCTGCAGAAGGGAAATGAGCTGGCCCTGCCCAGCAAGTATGTGA

ACTTCCTGTACCTGGCCTCCCACTATGAGAAGCTGAAGGGCAGCCCTGAG

GACAATGAGCAGAAGCAGCTGTTTGTGGAGCAGCACAAGCACTACCTGGA

TGAGATCATTGAGCAGATCTCTGAGTTCAGCAAGAGAGTGATCCTGGCTG

ATGCCAACCTGGACAAGGTGCTGTCTGCCTACAACAAGCACAGGGACAAG

CCCATCAGAGAGCAGGCTGAGAACATCATCCACCTGTTCACCCTGACCAA

CCTGGGAGCTCCAGCTGCCTTCAAGTACTTTGACACCACCATTGACAGGA

AGAGATACACCAGCACCAAGGAGGTGCTGGATGCCACCCTGATCCACCAG

TCCATCACAGGGCTGTATGAAACCAGAATTGACCTGAGCCAGCTGGGAGG

AGACCCCAAGAAGAAGAGAAAGGTGTGA.
```

SEQ ID NO: 1 and SEQ ID NO: 2 contain nuclear localization sequences (GACCC-CAAGAAGAAGCGCAAGGTG, nucleotides 4102-4125 of SEQ ID NO: 1) followed by a TGA stop codon shown in bolded text. The recombinant Cas9 sequences can be modified to include no nuclear localization sequence, or to include an alternative stop codon.

The percent sequence identity between the starting Cas9 sequence of SEQ ID NO: 3 and the recombinant Cas9 of SEQ ID NO: 1 is 69%. The percent sequence identity between the starting Cas9 sequence of SEQ ID NO: 3 and the recombinant Cas9 of SEQ ID NO: 2 is 72%. The percent sequence identity between the recombinant Cas9 of SEQ ID NO: 1 and the recombinant Cas9 of SEQ ID NO: 2 is 92% (see FIG. 6). An exemplary starting nucleic acid sequence of Cas9 is shown below with reference to SEQ ID NO: 3. SEQ ID NO: 3 is a human codon optimized Cas9 sequence available from ADDGENE® in plasmid #41815.

An exemplary human codon optimized Cas9 sequence is shown below as SEQ ID NO: 3.

```
                                          (SEQ ID NO: 3)
ATGGACAAGAAGTACTCCATTGGGCTCGATATCGGCACAAACAGCGTCGG

CTGGGCCGTCATTACGGACGAGTACAAGGTGCCGAGCAAAAAATTCAAAG

TTCTGGGCAATACCGATCGCCACAGCATAAAGAAGAACCTCATTGGCGCC

CTCCTGTTCGACTCCGGGGAGACGGCCGAAGCCACGCGGCTCAAAAGAAC

AGCACGGCGCAGATATACCCGCAGAAAGAATCGGATCTGCTACCTGCAGG

AGATCTTTAGTAATGAGATGGCTAAGGTGGATGACTCTTTCTTCCATAGG

CTGGAGGAGTCCTTTTTGGTGGAGGAGGATAAAAAGCACGAGCGCCACCC

AATCTTTGCAATATCGTGGACGAGGTGGCGTACCATGAAAAGTACCCAA

CCATATATCATCTGAGGAAGAAGCTTGTAGACAGTACTGATAAGGCTGAC

TTGCGGTTGATCTATCTCGCGCTGGCGCATATGATCAAATTTCGGGGACA

CTTCCTCATCGAGGGGGACCTGAACCCAGACAACAGCGATGTCGACAAAC

TCTTTATCCAACTGGTTCAGACTTACAATCAGCTTTTCGAAGAGAACCCG

ATCAACGCATCCGGAGTTGACGCCAAAGCAATCCTGAGCGCTAGGCTGTC

CAAATCCCGGCGGCTCGAAAACCTCATCGCACAGCTCCCTGGGGAGAAGA
```

```
AGAACGGCCTGTTTGGTAATCTTATCGCCCTGTCACTCGGGCTGACCCCC
AACTTTAAATCTAACTTCGACCTGGCCGAAGATGCCAAGCTTCAACTGAG
CAAAGACACCTACGATGATGATCTCGACAATCTGCTGGCCCAGATCGGCG
ACCAGTACGCAGACCTTTTTTGGCGGCAAAGAACCTGTCAGACGCCATT
CTGCTGAGTGATATTCTGCGAGTGAACACGGAGATCACCAAAGCTCCGCT
GAGCGCTAGTATGATCAAGCGCTATGATGAGCACCACCAAGACTTGACTT
TGCTGAAGGCCCTTGTCAGACAGCAACTGCCTGAGAAGTACAAGGAAATT
TTCTTCGATCAGTCTAAAAATGGCTACGCCGGATACATTGACGGCGGAGC
AAGCCAGGAGGAATTTTACAAATTTATTAAGCCCATCTTGGAAAAAATGG
ACGGCACCGAGGAGCTGCTGGTAAAGCTTAACAGAGAAGATCTGTTGCGC
AAACAGCGCACTTTCGACAATGGAAGCATCCCCCACCAGATTCACCTGGG
CGAACTGCACGCTATCCTCAGGCGGCAAGAGGATTTCTACCCCTTTTTGA
AAGATAACAGGGAAAAGATTGAGAAAATCCTCACATTTCGGATACCCTAC
TATGTAGGCCCCCTCGCCCGGGGAAATTCCAGATTCGCGTGGATGACTCG
CAAATCAGAAGAGACCATCACTCCCTGGAACTTCGAGGAAGTCGTGGATA
AGGGGGCCTCTGCCCAGTCCTTCATCGAAAGGATGACTAACTTTGATAAA
AATCTGCCTAACGAAAAGGTGCTTCCTAAACACTCTCTGCTGTACGAGTA
CTTCACAGTTTATAACGAGCTCACCAAGGTCAAATACGTCACAGAAGGGA
TGAGAAAGCCAGCATTCCTGTCTGGAGAGCAGAAGAAAGCTATCGTGGAC
CTCCTCTTCAAGACGAACCGGAAAGTTACCGTGAAACAGCTCAAAGAAGA
CTATTTCAAAAAGATTGAATGTTTCGACTCTGTTGAAATCAGCGGAGTGG
AGGATCGCTTCAACGCATCCCTGGGAACGTATCACGATCTCCTGAAAATC
ATTAAAGACAAGGACTTCCTGGACAATGAGGAGAACGAGGACATTCTTGA
GGACATTGTCCTCACCCTTACGTTGTTTGAAGATAGGGAGATGATTGAAG
AACGCTTGAAAACTTACGCTCATCTCTTCGACGACAAAGTCATGAAACAG
CTCAAGAGGCGCCGATATACAGGATGGGGCGGCTGTCAAGAAAACTGAT
CAATGGGATCCGAGACAAGCAGAGTGGAAAGACAATCCTGGATTTTCTTA
AGTCCGATGGATTTGCCAACCGGAACTTCATGCAGTTGATCCATGATGAC
TCTCTCACCTTTAAGGAGGACATCCAGAAAGCACAAGTTTCTGGCCAGGG
GGACAGTCTTCACGAGCACATCGCTAATCTTGCAGGTAGCCCAGCTATCA
AAAAGGGAATACTGCAGACCGTTAAGGTCGTGGATGAACTCGTCAAAGTA
ATGGGAAGGCATAAGCCCGAGAATATCGTTATCGAGATGGCCCGAGAGAA
CCAAACTACCCAGAAGGGACAGAAGAACAGTAGGGAAAGGATGAAGAGGA
TTGAAGAGGGTATAAAAGAACTGGGGTCCCAAATCCTTAAGGAACACCCA
GTTGAAAACACCCAGCTTCAGAATGAGAAGCTCTACCTGTACTACCTGCA
GAACGGCAGGGACATGTACGTGGATCAGGAACTGGACATCAATCGGCTCT
CCGACTACGACGTGGATCATATCGTGCCCCAGTCTTTTCTCAAAGATGAT
TCTATTGATAATAAAGTGTTGACAAGATCCGATAAAAATAGAGGGAAGAG
TGATAACGTCCCCTCAGAAGAAGTTGTCAAGAAAATGAAAAATTATTGGC
GGCAGCTGCTGAACGCCAAACTGATCACACAACGGAAGTTCGATAATCTG
ACTAAGGCTGAACGAGGTGGCCTGTCTGAGTTGGATAAAGCCGGCTTCAT
CAAAAGGCAGCTTGTTGAGACACGCCAGATCACCAAGCACGTGGCCCAAA
TTCTCGATTCACGCATGAACACCAAGTACGATGAAAATGACAAACTGATT
CGAGAGGTGAAAGTTATTACTCTGAAGTCTAAGCTGGTCTCAGATTTCAG
AAAGGACTTTCAGTTTTATAAGGTGAGAGAGATCAACAATTACCACCATG
CGCATGATGCCTACCTGAATGCAGTGGTAGGCACTGCACTTATCAAAAAA
TATCCCAAGCTTGAATCTGAATTTGTTTACGGAGACTATAAAGTGTACGA
TGTTAGGAAAATGATCGCAAAGTCTGAGCAGGAAATAGGCAAGGCCACCG
CTAAGTACTTCTTTTACAGCAATATTATGAATTTTTTCAAGACCGAGATT
ACACTGGCCAATGGAGAGATTCGGAAGCGACCACTTATCGAAACAAACGG
AGAAACAGGAGAAATCGTGTGGGACAAGGGTAGGGATTTCGCGACAGTCC
GGAAGGTCCTGTCCATGCCGCAGGTGAACATCGTTAAAAAGACCGAAGTA
CAGACCGGAGGCTTCTCCAAGGAAAGTATCCTCCCGAAAAGGAACAGCGA
CAAGCTGATCGCACGCAAAAAAGATTGGGACCCCAAGAAATACGGCGGAT
TCGATTCTCCTACAGTCGCTTACAGTGTACTGGTTGTGGCCAAAGTGGAG
AAAGGGAAGTCTAAAAAACTCAAAAGCGTCAAGGAACTGCTGGGCATCAC
AATCATGGAGCGATCAAGCTTCGAAAAAAACCCCATCGACTTTCTCGAGG
CGAAAGGATATAAAGAGGTCAAAAAAGACCTCATCATTAAGCTTCCCAAG
TACTCTCTCTTTGAGCTTGAAAACGGCCGGAAACGAATGCTCGCTAGTGC
GGGCGAGCTGCAGAAAGGTAACGAGCTGGCACTGCCCTCTAAATACGTTA
ATTTCTTGTATCTGGCCAGCCACTATGAAAAGCTCAAAGGGTCTCCCGAA
GATAATGAGCAGAAGCAGCTGTTCGTGGAACAACACAAACACTACCTTGA
TGAGATCATCGAGCAAATAAGCGAATTCTCCAAAAGAGTGATCCTCGCCG
ACGCTAACCTCGATAAGGTGCTTTCTGCTTACAATAAGCACAGGGATAAG
CCCATCAGGGAGCAGGCAGAAAACATTATCCACTTGTTTACTCTGACCAA
CTTGGGCGCGCCTGCAGCCTTCAAGTACTTCGACACCACCATAGACAGAA
AGCGGTACACCTCTACAAAGGAGGTCCTGGACGCCACACTGATTCATCAG
TCAATTACGGGGCTCTATGAAACAAGAATCGACCTCTCTCAGCTCGGTGG
AGACAGCAGGGCTGACCCCAAGAAGAAGAGGAAGGTGTGA
```

Figure 7A:
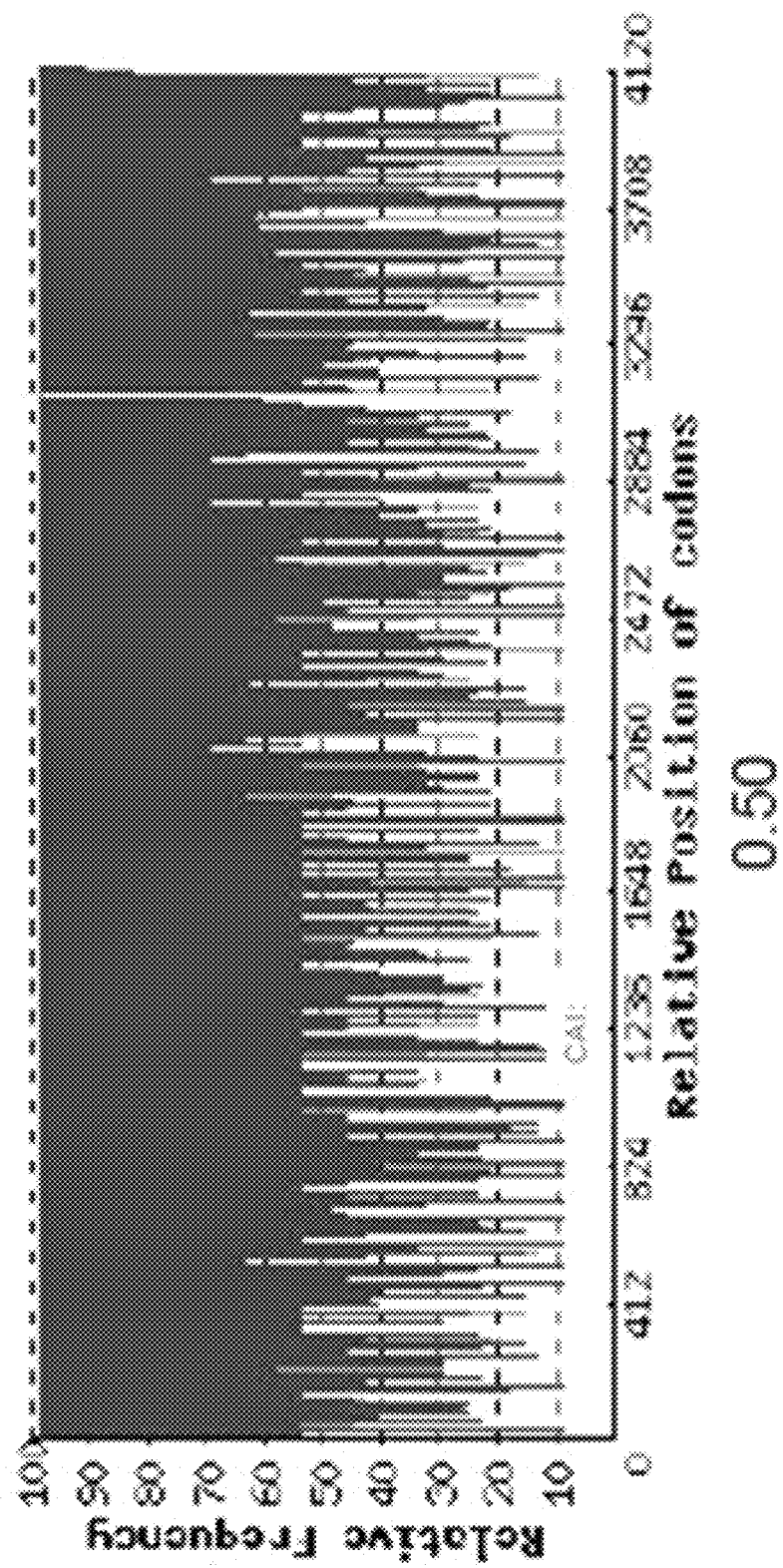
Figure 7C:
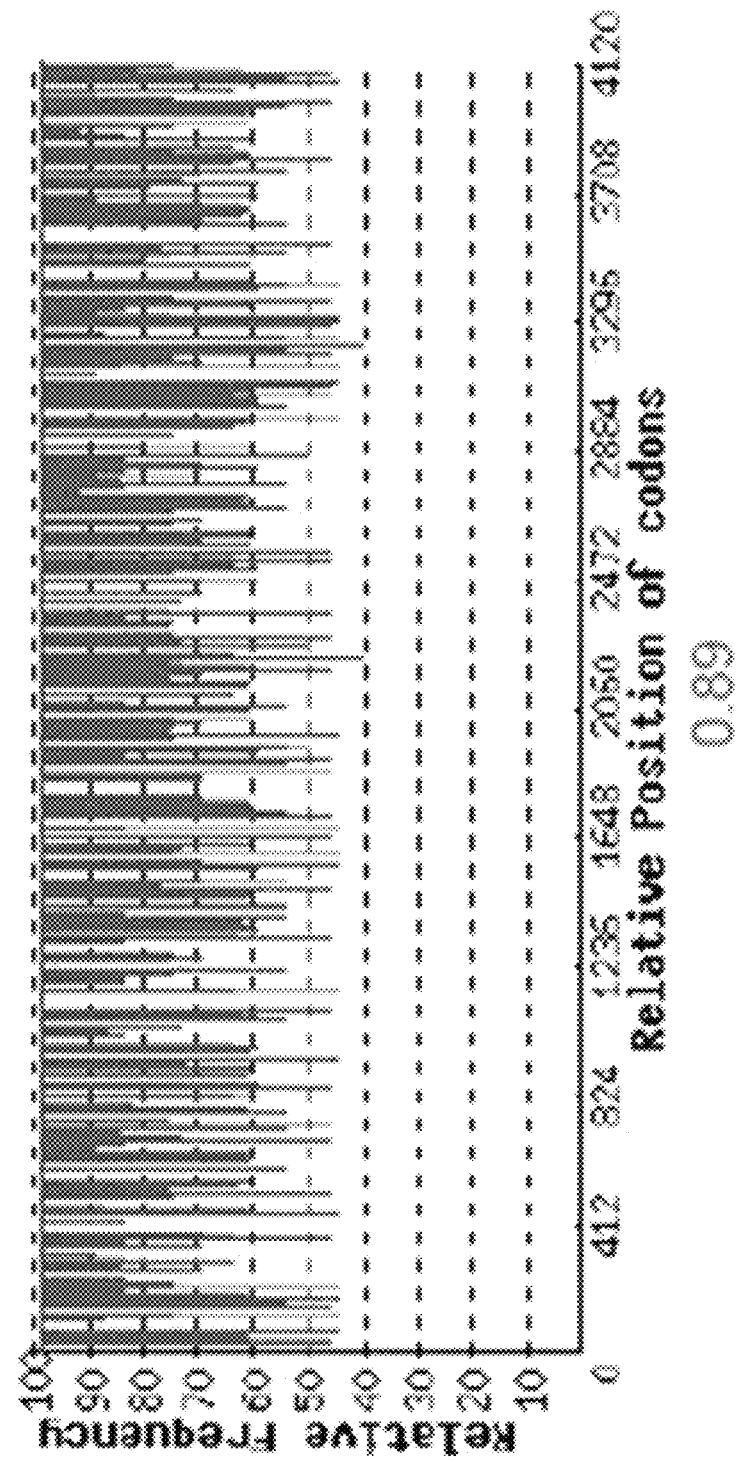

Sequences can be assessed by codon adaptive index (CAI) for their distribution of codon usage frequency along the length of the gene sequence. A CAI of 1.0 is considered to be perfect in the desired expression tissue, and a CAI of >0.8 is regarded as good, in terms of high gene expression level. The CAI scores and relative frequency per codon position for SEQ ID NO: 1, SEQ ID NO: 2, and SEQ ID NO: 3 are shown in FIG. 7A-FIG. 7C.

Figure 8A:
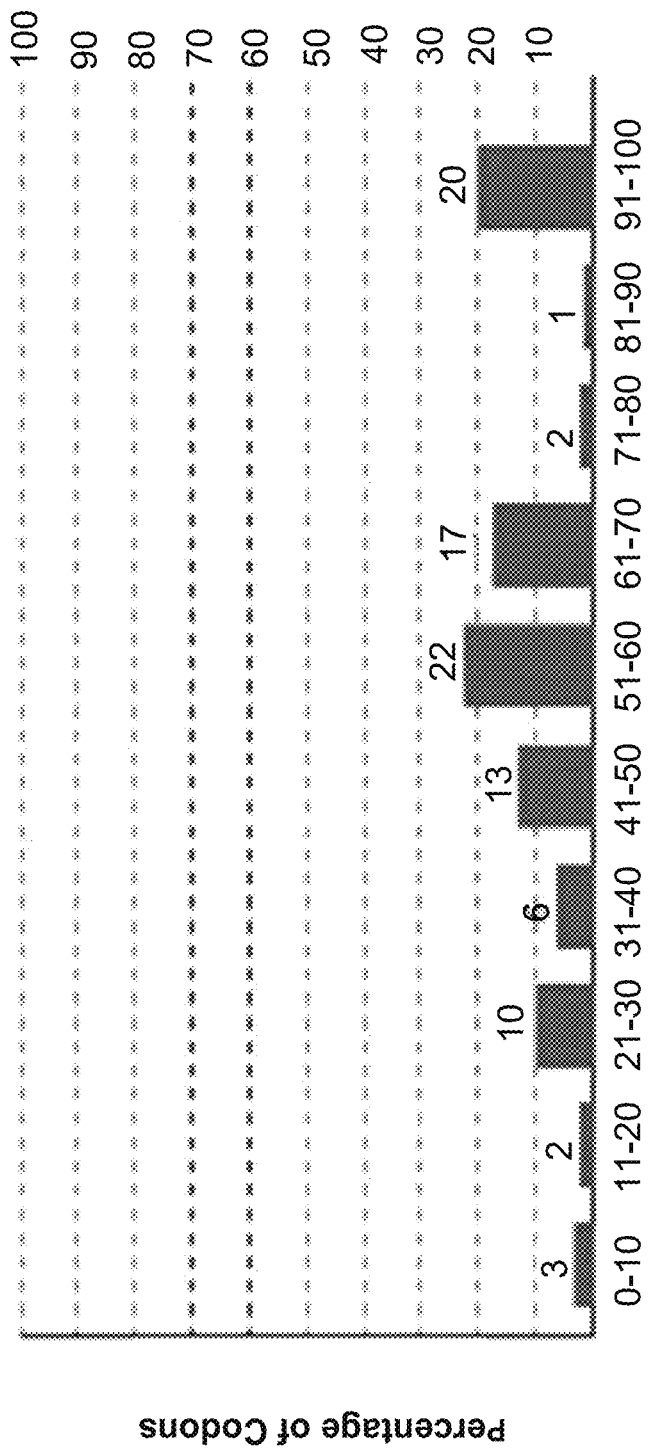

Sequences can be assessed by their Frequency of Optimal Codons (FOP). The FOP is generated against the custom human liver codon usage index. The percentage distribution of codons in computed codon quality groups. The value of 100 is set for the codon with the highest usage frequency for a given amino acid in the desired expression tissue. The FOPs for SEQ ID NO: 1, SEQ ID NO: 2, and SEQ ID NO: 3 are shown in FIG. 8A-8C.

Figure 9B:
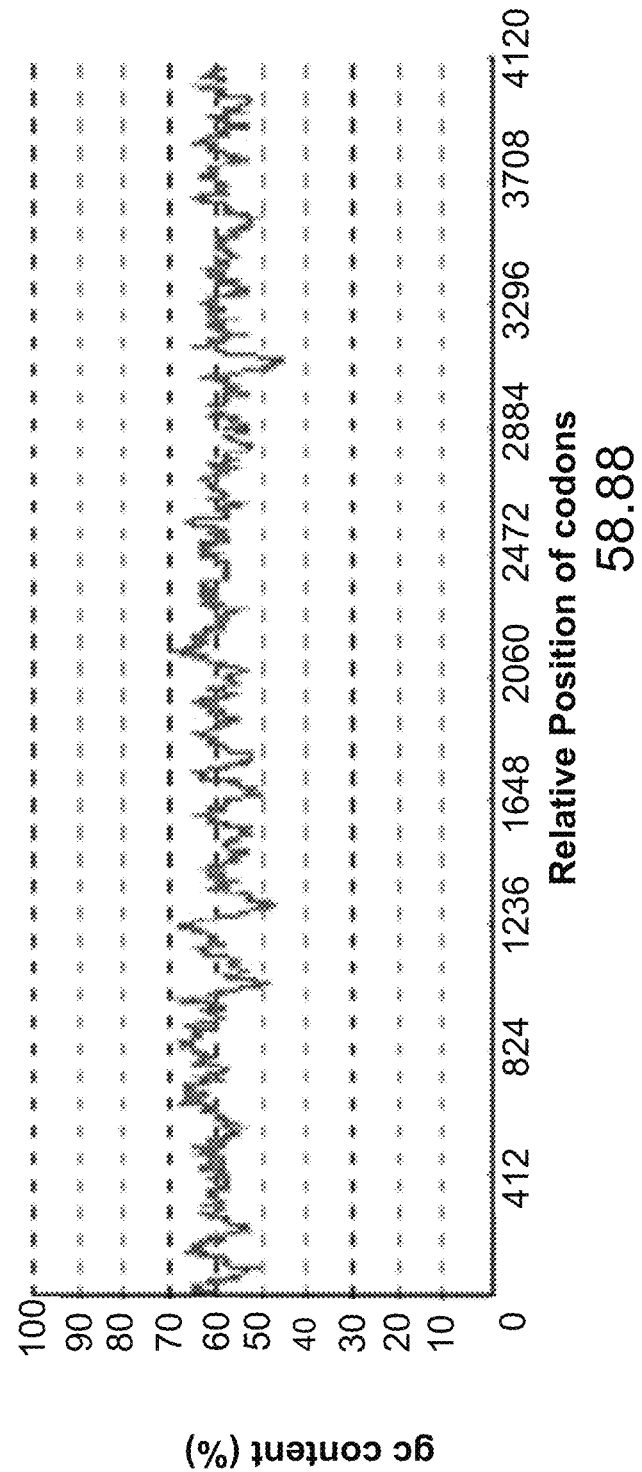

GC content, the percentage of the sequence consisting of guanosine or cytosine is also assessed for optimized sequences. The GC content for SEQ ID NO: 1, SEQ ID NO: 2, and SEQ ID NO: 3 are shown in FIG. 9A-9C.

Example 3: Alternative Optimization Protocols

Alternative optimization protocols exist. Additional codon-optimized Cas9 sequences were also developed. SEQ ID NOs: 4-7 were prepared by GENSCRIPT® algorithms. The utilized algorithm takes into account codon usage bias, GC content, CpG dinucleotides content, mRNA secondary structure, cryptic splicing sites, premature polyA sites, internal chi sites and ribosomal binding sites, negative CpG islands, RNA instability motif (ARE), repeat sequences (direct repeat, reverse repeat and Dyad repeat), and restriction sites that may interfere with cloning, but do not take into consideration tRNA frequencies.

Human Optimized Cas9-NLS-NCG (SEQ ID NO: 4) was optimized for codon frequencies similar to that of the whole human genome to have no CpG dinucleotides. SEQ ID NO: 4 has a CAI of 0.93 and a GC content of 49.59.

Human Optimized Cas9-NLS-NCG (SEQ ID NO: 4) is shown below:

(SEQ ID NO: 4)
ATGGACAAGAAGTATTCTATTGGCCTGGATATTGGCACAAATTCTGTGGG

CTGGGCTGTGATCACAGATGAGTACAAGGTGCCATCTAAGAAGTTTAAGG

TGCTGGGCAACACAGATAGGCACAGCATCAAGAAGAATCTGATTGGAGCC

CTGCTGTTTGACTCTGGAGAGACAGCAGAGGCAACAAGACTGAAGAGAAC

AGCCAGAAGAAGGTATACAAGAAGGAAGAATAGGATCTGCTACCTGCAGG

AGATCTTCAGCAATGAGATGGCCAAGGTGGATGATTCCTTCTTTCACAGA

CTGGAGGAGTCTTTCCTGGTGGAGGAGGATAAGAAGCATGAGAGGCACCC

CATCTTTGGCAACATTGTGGATGAGGTGGCCTATCATGAGAAGTACCCTA

CAATCTATCACCTGAGGAAGAAGCTGGTGGACAGCACAGATAAGGCTGAC

CTGAGACTGATCTATCTGGCCCTGGCCCACATGATCAAGTTCAGAGGCCA

CTTTCTGATTGAGGGAGATCTGAACCCAGACAATTCTGATGTGGACAAGC

TGTTCATCCAGCTGGTGCAGACCTACAATCAGCTGTTTGAGGAGAACCCC

ATCAATGCATCTGGAGTGGATGCAAAGGCAATCCTGTCTGCCAGACTGTC

TAAGAGCAGAAGGCTGGAGAACCTGATTGCCCAGCTGCCAGGAGAGAAGA

AGAATGGCCTGTTTGGCAATCTGATTGCCCTGAGCCTGGGCCTGACACCC

AACTTCAAGTCCAATTTTGATCTGGCAGAGGATGCCAAGCTGCAGCTGAG

CAAGGACACCTATGATGATGACCTGGATAACCTGCTGGCCCAGATTGGGG

ATCAGTATGCTGACCTGTTCCTGGCTGCCAAGAATCTGTCTGATGCCATC

CTGCTGTCTGATATCCTGAGAGTGAACACAGAGATCACAAAGGCCCCCCT

GTCTGCCTCTATGATCAAGAGGTATGATGAGCACCACCAGGATCTGACCC

TGCTGAAGGCCCTGGTGAGACAGCAGCTGCCTGAGAAGTACAAGGAGATC

TTCTTTGATCAGTCTAAGAATGGATATGCAGGATATATTGATGGAGGAGC

AAGCCAGGAGGAGTTCTACAAGTTTATCAAGCCCATCCTGGAGAAGATGG

ATGGCACAGAGGAGCTGCTGGTGAAGCTGAATAGGGAGGACCTGCTGAGG

AAGCAGAGAACCTTTGATAATGGCTCCATCCCTCACCAGATCCACCTGGG

AGAGCTGCATGCAATCCTGAGGAGGCAGGAGGACTTCTACCCATTTCTGA

AGGATAACAGGGAGAAGATTGAGAAGATCCTGACATTTAGAATCCCCTAC

TATGTGGGCCCTCTGGCCAGGGGCAATTCTAGGTTTGCCTGGATGACCAG

AAAGTCTGAGGAGACAATCACACCCTGGAACTTTGAGGAGGTGGTGGATA

AGGGGAGCCTCTGCCCAGTCCTTCATTGAGAGGATGACAAATTTTGACAAG

AACCTGCCAAATGAGAAGGTGCTGCCCAAGCACTCTCTGCTGTATGAGTA

TTTCACAGTGTATAATGAGCTGACAAAGGTGAAGTATGTGACAGAGGGCA

TGAGAAAGCCTGCCTTCCTGTCTGGAGAGCAGAAGAAGGCCATTGTGGAC

CTGCTGTTTAAGACCAATAGGAAGGTGACAGTGAAGCAGCTGAAGGAGGA

CTATTTCAAGAAGATTGAGTGTTTTGATTCTGTGGAGATCTCTGGAGTGG

AGGACAGATTCAATGCAAGCCTGGGCACCTACCATGATCTGCTGAAGATC

ATCAAGGATAAGGACTTCCTGGACAATGAGGAGAATGAGGATATCCTGGA

GGACATTGTGCTGACCCTGACACTGTTTGAGGATAGGGAGATGATTGAGG

AGAGACTGAAGACATATGCCCACCTGTTTGATGACAAAGTGATGAAGCAG

CTGAAGAGAAGGAGATACACTGGATGGGCAGGCTGTCCAGAAAGCTGAT

CAATGGCATCAGAGACAAGCAGTCTGGCAAGACAATCCTGGACTTTCTGA

AGTCTGATGGCTTTGCCAACAGGAACTTCATGCAGCTGATCCATGATGAC

TCCCTGACCTTCAAGGAGGATATCCAGAAGGCACAGGTGTCTGGACAGGG

AGACTCTCTGCATGAGCACATTGCCAACCTGGCTGGCTCTCCTGCCATCA

AGAAGGGCATCCTGCAGACAGTGAAGGTGGTGGATGAGCTGGTGAAAGTG

ATGGGCAGGCACAAGCCAGAGAACATTGTGATTGAGATGGCCAGAGAGAA

TCAGACCACACAGAAGGGCCAGAAGAACAGCAGGGAGAGAATGAAGAGAA

TTGAGGAGGGCATCAAGGAGCTGGGCTCCCAGATCCTGAAGGAGCACCCT

GTGGAGAACACACAGCTGCAGAATGAGAAGCTGTATCTGTACTATCTGCA

GAATGGCAGAGATATGTATGTGGACCAGGAGCTGGATATCAACAGACTGT

CTGATTATGATGTGGATCACATTGTGCCACAGAGCTTCCTGAAGGATGAC

TCCATTGACAATAAGGTGCTGACCAGGTCTGACAAGAACAGAGGCAAGTC

TGATAATGTGCCCTCAGAGGAGGTGGTGAAGAAGATGAAGAACTACTGGA

GGCAGCTGCTGAATGCCAAGCTGATCACACAGAGGAAGTTTGATAACCTG

ACCAAGGCAGAGAGGAGGAGGCCTGTCTGAGCTGGACAAGGCAGGCTTCAT

CAAGAGGCAGCTGGTGGAGACAAGACAGATCACAAAGCATGTGGCCCAGA

TCCTGGATTCTAGAATGAACACAAAGTATGATGAGAATGACAAGCTGATC

AGGGAGGTGAAAGTGATCACCCTGAAGTCTAAGCTGGTGTCAGACTTTAG

GAAGGATTTCCAGTTTTATAAGGTGAGAGAGATCAACAACTACCACCATG

CCCATGATGCCTACCTGAATGCTGTGGTGGGCACAGCCCTGATCAAGAAG

TACCCTAAGCTGGAGTCTGAGTTTGTGTATGGAGACTATAAGGTGTATGA

TGTGAGGAAGATGATTGCCAAGTCTGAGCAGGAGATTGGCAAGGCCACAG

CCAAGTATTTCTTTTACTCTAACATCATGAATTTCTTTAAGACAGAGATC

ACACTGGCCAATGGAGAGATCAGGAAGAGACCACTGATTGAGACAAATGG

AGAGACAGGAGAGATTGTGTGGGACAAGGGCAGAGATTTTGCCACAGTGA

GAAAGGTGCTGAGCATGCCCCAAGTGAATATTGTGAAGAAGACTGAGGTG

CAGACAGGAGGCTTCTCTAAGGAGAGCATCCTGCCTAAGAGGAACTCTGA

TAAGCTGATTGCCAGAAAGAAGGACTGGGATCCTAAGAAGTATGGAGGCT

TTGACTCTCCAACAGTGGCCTACTCAGTGCTGGTGGTGGCCAAGGTGGAG

AAGGGCAAGTCTAAGAAGCTGAAGTCTGTGAAGGAGCTGCTGGGCATCAC

CATCATGGAGAGAAGCTCCTTTGAGAAGAATCCTATTGATTTTCTGGAGG

CCAAGGGCTATAAGGAGGTGAAGAAGGACCTGATCATCAAGCTGCCAAAG

TACTCCCTGTTTGAGCTGGAGAATGGCAGGAAGAGAATGCTGGCATCTGC

TGGAGAGCTGCAGAAGGGCAATGAGCTGGCCCTGCCCAGCAAGTATGTGA

ACTTCCTGTATCTGGCCTCCCACTATGAGAAGCTGAAGGGCTCCCCTGAG

GATAATGAGCAGAAGCAGCTGTTTGTGGAGCAGCACAAGCACTATCTGGA

TGAGATCATTGAGCAGATCTCAGAGTTCTCTAAGAGAGTGATCCTGGCTG

ATGCCAATCTGGATAAGGTGCTGAGTGCCTACAACAAGCACAGGGATAAG

CCAATCAGAGAGCAGGCAGAGAATATCATCCACCTGTTCACCCTGACAAA

CCTGGGAGCACCAGCAGCCTTCAAGTATTTTGACACCACAATTGATAGGA

AGAGGTACACCTCCACAAAGGAGGTGCTGGATGCCACCCTGATCCACCAG

AGCATCACAGGCCTGTATGAGACAAGGATTGACCTGTCCCAGCTGGGAGG

AGACCCCAAGAAGAAGAGGAAGGTGTGA

Human Optimized Cas9-NLS-WCG Genscript (SEQ ID NO: 5) was optimized for codon frequencies similar to that of the whole human genome and contains CpG dinucleotides. SEQ ID NO: 5 has a CAI of 0.94 and a GC content of 52.74.

Human Optimized Cas9-NLS-WCG Genscript (SEQ ID NO: 5) is shown below:

(SEQ ID NO: 5)
ATGGACAAGAAGTATTCTATCGGCCTGGATATCGGCACAAATAGCGTGGG

CTGGGCCGTGATCACCGACGAGTACAAGGTGCCATCTAAGAAGTTTAAGG

TGCTGGGCAACACCGATCGCCACAGCATCAAGAAGAATCTGATCGGCGCC

CTGCTGTTCGACTCCGGAGAGACAGCAGAGGCAACACGGCTGAAGAGAAC

CGCCCGGAGAAGGTATACACGCCGGAAGAATCGGATCTGCTACCTGCAGG

AGATCTTCAGCAACGAGATGGCCAAGGTGGACGATTCCTTCTTTCACAGA

CTGGAGGAGTCTTTCCTGGTGGAGGAGGATAAGAAGCACGAGAGGCACCC

CATCTTTGGCAACATCGTGGACGAGGTGGCCTATCACGAGAAGTACCCTA

CAATCTATCACCTGAGGAAGAAGCTGGTGGACAGCACCGATAAGGCCGAC

CTGCGCCTGATCTATCTGGCCCTGGCCCACATGATCAAGTTCCGGGGCCA

CTTTCTGATCGAGGGCGATCTGAACCCAGACAATTCCGATGTGGACAAGC

TGTTCATCCAGCTGGTGCAGACCTACAATCAGCTGTTTGAGGAGAACCCC

ATCAATGCATCCGGAGTGGACGCAAAGGCAATCCTGTCTGCCAGACTGTC

TAAGAGCAGAAGGCTGGAGAACCTGATCGCCCAGCTGCCAGGCGAGAAGA

GAACGGCCTGTTTGGCAATCTGATCGCCCTGAGCCTGGGCCTGACACCC

AACTTCAAGTCCAATTTTGATCTGGCCGAGGACGCCAAGCTGCAGCTGAG

CAAGGACACCTATGACGATGACCTGGATAACCTGCTGGCCCAGATCGGCG

ATCAGTACGCCGACCTGTTCCTGGCCGCCAAGAATCTGTCCGACGCCATC

CTGCTGTCTGATATCCTGAGAGTGAACACCGAGATCACAAAGGCCCCCCT

GTCCGCCTCTATGATCAAGCGGTACGACGAGCACCACCAGGATCTGACCC

TGCTGAAGGCCCTGGTGCGGCAGCAGCTGCCTGAGAAGTACAAGGAGATC

TTCTTTGATCAGTCTAAGAATGGATACGCAGGATATATCGACGGAGGAGC

AAGCCAGGAGGAGTTCTACAAGTTTATCAAGCCCATCCTGGAGAAGATGG

ACGGCACAGAGGAGCTGCTGGTGAAGCTGAATAGGGAGGACCTGCTGAGG

AAGCAGCGCACCTTTGATAACGGCTCCATCCCTCACCAGATCCACCTGGG

AGAGCTGCACGCAATCCTGCGCCGGCAGGAGGACTTCTACCCATTTCTGA

AGGATAACAGGGAGAAGATCGAGAAGATCCTGACATTCCGCATCCCCTAC

TATGTGGGCCCTCTGGCCAGGGGCAATTCTCGCTTTGCCTGGATGACCAG

AAAGAGCGAGGAGACAATCACACCCTGGAACTTCGAGGAGGTGGTGGATA

AGGGCGCCAGCGCCCAGTCCTTCATCGAGAGGATGACAAATTTTGACAAG

AACCTGCCAAATGAGAAGGTGCTGCCCAAGCACTCTCTGCTGTACGAGTA

TTTCACCGTGTATAACGAGCTGACAAAGGTGAAGTACGTGACCGAGGGCA

TGCGCAAGCCTGCCTTCCTGAGCGGCGAGCAGAAGAAGGCCATCGTGGAC

CTGCTGTTTAAGACCAATCGGAAGGTGACAGTGAAGCAGCTGAAGGAGGA

CTATTTCAAGAAGATCGAGTGTTTTGATAGCGTGGAGATCTCCGGAGTGG

AGGGCCGGTTCAACGCAAGCCTGGGCACCTACCACGATCTGCTGAAGATC

ATCAAGGATAAGGACTTCCTGGACAACGAGGAGAATGAGGATATCCTGGA

GGACATCGTGCTGACCCTGACACTGTTTGAGGATCGGGAGATGATCGAGG

AGAGACTGAAGACATATGCCCACCTGTTCGATGACAAAGTGATGAAGCAG

CTGAAGAGAAGGCGCTACACCGGATGGGGCCGGCTGTCCAGAAAGCTGAT

CAATGGCATCAGAGACAAGCAGTCCGGCAAGACAATCCTGGACTTTCTGA

AGTCTGATGGCTTCGCCAACAGGAACTTCATGCAGCTGATCCACGATGAC

TCCCTGACCTTCAAGGAGGATATCCAGAAGGCACAGGTGTCCGGACAGGG

CGACTCTCTGCACGAGCACATCGCCAACCTGGCCGGCTCTCCTGCCATCA

AGAAGGGCATCCTGCAGACCGTGAAGGTGGTGGACGAGCTGGTGAAAGTG

ATGGGCAGGCACAAGCCAGAGAACATCGTGATCGAGATGGCCCGCGAGAA

TCAGACCACACAGAAGGGCCAGAAGAACAGCCGGGAGAGAATGAAGCGCA

TCGAGGAGGGCATCAAGGAGCTGGGCTCCCAGATCCTGAAGGAGCACCCT

GTGGAGAACACACAGCTGCAGAATGAGAAGCTGTATCTGTACTATCTGCA

GAATGGCCGGGATATGTACGTGGACCAGGAGCTGGATATCAACAGACTGT

CTGATTACGACGTGGATCACATCGTGCCACAGAGCTTCCTGAAGGATGAC

TCCATCGACAATAAGGTGCTGACCCGGAGCGACAAGAACAGAGGCAAGAG

CGATAATGTGCCCTCCGAGGAGGTGGTGAAGAAGATGAAGAACTACTGGC

GGCAGCTGCTGAATGCCAAGCTGATCACACAGCGGAAGTTTGATAACCTG

ACCAAGGCAGAGAGGAGGCCTGTCCGAGCTGGACAAGGCAGGCTTCAT

CAAGAGGCAGCTGGTGGAGACACGCCAGATCACAAAGCACGTGGCCCAGA

TCCTGGATTCTAGAATGAACACAAAGTACGATGAGAATGACAAGCTGATC

AGGGAGGTGAAAGTGATCACCCTGAAGTCTAAGCTGGTGAGCGACTTTCG

```
GAAGGATTTCCAGTTTTATAAGGTGAGAGAGATCAACAACTACCACCACG

CCCACGACGCCTACCTGAACGCCGTGGTGGGCACAGCCCTGATCAAGAAG

TACCCTAAGCTGGAGAGCGAGTTCGTGTACGGCGACTATAAGGTGTACGA

TGTGCGGAAGATGATCGCCAAGTCCGAGCAGGAGATCGGCAAGGCCACCG

CCAAGTATTTCTTTTACTCTAACATCATGAATTTCTTTAAGACCGAGATC

ACACTGGCCAATGGCGAGATCAGGAAGCGCCCACTGATCGAGACAAACGG

CGAGACAGGCGAGATCGTGTGGGACAAGGGCCGGGATTTTGCCACCGTGA

GAAAGGTGCTGAGCATGCCCCAAGTGAATATCGTGAAGAAGACCGAGGTG

CAGACAGGCGGCTTCTCTAAGGAGAGCATCCTGCCTAAGAGGAACTCCGA

TAAGCTGATCGCCCGCAAGAAGGACTGGGATCCTAAGAAGTATGGCGGCT

TCGACTCTCCAACAGTGGCCTACAGCGTGCTGGTGGTGGCCAAGGTGGAG

AAGGGCAAGTCTAAGAAGCTGAAGAGCGTGAAGGAGCTGCTGGGCATCAC

CATCATGGAGAGAAGCTCCTTCGAGAAGAATCCTATCGATTTTCTGGAGG

CCAAGGGCTATAAGGAGGTGAAGAAGGACCTGATCATCAAGCTGCCAAAG

TACTCCCTGTTTGAGCTGGAGAACGGCCGGAAGAGAATGCTGGCATCTGC

CGGAGAGCTGCAGAAGGGCAATGAGCTGGCCCTGCCCAGCAAGTACGTGA

ACTTCCTGTATCTGGCCTCCCACTACGAGAAGCTGAAGGGCTCCCCTGAG

GATAACGAGCAGAAGCAGCTGTTTGTGGAGCAGCACAAGCACTATCTGGA

CGAGATCATCGAGCAGATCTCCGAGTTCTCTAAGAGAGTGATCCTGGCCG

ACGCCAATCTGGATAAGGTGCTGAGCGCCTACAACAAGCACAGGGATAAG

CCAATCCGCGAGCAGGCCGAGAATATCATCCACCTGTTCACCCTGACAAA

CCTGGGAGCACCAGCAGCCTTCAAGTATTTTGACACCACAATCGATAGGA

AGCGGTACACCTCCACAAAGGAGGTGCTGGACGCCACCCTGATCCACCAG

AGCATCACCGGCCTGTACGAGACAAGGATCGACCTGTCCCAGCTGGGAGG

CGACCCCAAGAAGAAGCGGAAGGTGTGA
```

Human Liver Optimized Cas9-NLS-NCG Genscript (SEQ ID NO: 6) was optimized for codon frequencies similar to that of the human liver and contains no CpG dinucleotides. SEQ ID NO: 6 has a CAI of 0.89 and a GC content of 52.74.

Human Liver Optimized Cas9-NLS-NCG Genscript (SEQ ID NO: 6) is shown below:

```
                                          (SEQ ID NO: 6)
ATGGACAAGAAGTATTCTATTGGCCTGGATATTGGCACAAATTCTGTGGG

CTGGGCTGTGATCACAGATGAGTACAAGGTGCCATCTAAGAAGTTTAAGG

TGCTGGGCAACACAGATAGGCACAGCATCAAGAAGAATCTGATTGGAGCC

CTGCTGTTTGACTCTGGAGAGACAGCAGAGGCAACAAGACTGAAGAGAAC

AGCCAGAAGAAGGTATACAAGAAGGAAGAATAGGATCTGCTACCTGCAGG

AGATCTTCAGCAATGAGATGGCCAAGGTGGATGATTCCTTCTTTCACAGA

CTGGAGGAGTCTTTCCTGGTGGAGGAGGATAAGAAGCATGAGAGGCACCC

CATCTTTGGCAACATTGTGGATGAGGTGGCCTATCATGAGAAGTACCCTA

CAATCTATCACCTGAGGAAGAAGCTGGTGGACAGCACAGATAAGGCTGAC

CTGAGACTGATCTATCTGGCCCTGGCCCACATGATCAAGTTCAGAGGCCA

CTTTCTGATTGAGGGAGATCTGAACCCAGACAATTCTGATGTGGACAAGC

TGTTCATCCAGCTGGTGCAGACCTACAATCAGCTGTTTGAGGAGAACCCC

ATCAATGCATCTGGAGTGGATGCAAAGGCAATCCTGTCTGCCAGACTGTC

TAAGAGCAGAAGGCTGGAGAACCTGATTGCCCAGCTGCCAGGAGAGAAGA

AGAATGGCCTGTTTGGCAATCTGATTGCCCTGAGCCTGGGCCTGACACCC

AACTTCAAGTCCAATTTTGATCTGGCAGAGGATGCCAAGCTGCAGCTGAG

CAAGGACACCTATGATGATGACCTGGATAACCTGCTGGCCCAGATTGGGG

ATCAGTATGCTGACCTGTTCCTGGCTGCCAAGAATCTGTCTGATGCCATC

CTGCTGTCTGATATCCTGAGAGTGAACACAGAGATCACAAAGGCCCCCCT

GTCTGCCTCTATGATCAAGAGGTATGATGAGCACCACCAGGATCTGACCC

TGCTGAAGGCCCTGGTGAGACAGCAGCTGCCTGAGAAGTACAAGGAGATC

TTCTTTGATCAGTCTAAGAATGGATATGCAGGATATATTGATGGAGGAGC

AAGCCAGGAGGAGTTCTACAAGTTTATCAAGCCCATCCTGGAGAAGATGG

ATGGCACAGAGGAGCTGCTGGTGAAGCTGAATAGGGAGGACCTGCTGAGG

AAGCAGAGAACCTTTGATAATGGCTCCATCCCTCACCAGATCCACCTGGG

AGAGCTGCATGCAATCCTGAGGAGGCAGGAGGACTTCTACCCATTTCTGA

AGGATAACAGGGAGAAGATTGAGAAGATCCTGACATTTAGAATCCCCTAC

TATGTGGGCCCTCTGGCCAGGGGCAATTCTAGGTTTGCCTGGATGACCAG

AAAGTCTGAGGAGACAATCACACCCTGGAACTTTGAGGAGGTGGTGGATA

AGGGAGCCTCTGCCCAGTCCTTCATTGAGAGGATGACAAATTTTGACAAG

AACCTGCCAAATGAGAAGGTGCTGCCCAAGCACTCTCTGCTGTATGAGTA

TTTCACAGTGTATAATGAGCTGACAAAGGTGAAGTATGTGACAGAGGGCA

TGAGAAAGCCTGCCTTCCTGTCTGGAGAGCAGAAGAAGGCCATTGTGGAC

CTGCTGTTTAAGACCAATAGGAAGGTGACAGTGAAGCAGCTGAAGGAGGA

CTATTTCAAGAAGATTGAGTGTTTTGATTCTGTGGAGATCTCTGGAGTGG

AGGACAGATTCAATGCAAGCCTGGGCACCTACCATGATCTGCTGAAGATC

ATCAAGGATAAGGACTTCCTGGACAATGAGGAGAATGAGGATATCCTGGA

GGACATTGTGCTGACCCTGACACTGTTTGAGGATAGGGAGATGATTGAGG

AGAGACTGAAGACATATGCCCACCTGTTTGATGACAAAGTGATGAAGCAG

CTGAAGAGAAGGAGATACACTGGATGGGCAGGCTGTCCAGAAAGCTGAT

CAATGGCATCAGAGACAAGCAGTCTGGCAAGACAATCCTGGACTTTCTGA

AGTCTGATGGCTTTGCCAACAGGAACTTCATGCAGCTGATCCATGATGAC

TCCCTGACCTTCAAGGAGGATATCCAGAAGGCACAGGTGTCTGGACAGGG

AGACTCTCTGCATGAGCACATTGCCAACCTGGCTGGCTCTCCTGCCATCA

AGAAGGGCATCCTGCAGACAGTGAAGGTGGTGGATGAGCTGGTGAAAGTG

ATGGGCAGGCACAAGCCAGAGAACATTGTGATTGAGATGGCCAGAGAGAA

TCAGACCACACAGAAGGGCCAGAAGAACAGCAGGGAGAGAATGAAGAGAA

TTGAGGAGGGCATCAAGGAGCTGGGCTCCCAGATCCTGAAGGAGCACCCT

GTGGAGAACACACAGCTGCAGAATGAGAAGCTGTATCTGTACTATCTGCA

GAATGGCAGAGATATGTATGTGGACCAGGAGCTGGATATCAACAGACTGT
```

```
CTGATTATGATGTGGATCACATTGTGCCACAGAGCTTCCTGAAGGATGAC
TCCATTGACAATAAGGTGCTGACCAGGTCTGACAAGAACAGAGGCAAGTC
TGATAATGTGCCCTCAGAGGAGGTGGTGAAGAAGATGAAGAACTACTGGA
GGCAGCTGCTGAATGCCAAGCTGATCACACAGAGGAAGTTTGATAACCTG
ACCAAGGCAGAGAGAGGAGGCCTGTCTGAGCTGGACAAGGCAGGCTTCAT
CAAGAGGCAGCTGGTGGAGACAAGACAGATCACAAAGCATGTGGCCCAGA
TCCTGGATTCTAGAATGAACACAAAGTATGATGAGAATGACAAGCTGATC
AGGGAGGTGAAAGTGATCACCCTGAAGTCTAAGCTGGTGTCAGACTTTAG
GAAGGATTTCCAGTTTTATAAGGTGAGAGAGATCAACAACTACCACCATG
CCCATGATGCCTACCTGAATGCTGTGGTGGGCACAGCCCTGATCAAGAAG
TACCCTAAGCTGGAGTCTGAGTTTGTGTATGGAGACTATAAGGTGTATGA
TGTGAGGAAGATGATTGCCAAGTCTGAGCAGGAGATTGGCAAGGCCACAG
CCAAGTATTTCTTTTACTCTAACATCATGAATTTCTTTAAGACAGAGATC
ACACTGGCCAATGGAGAGATCAGGAAGAGACCACTGATTGAGACAAATGG
AGAGACAGGAGAGATTGTGTGGGACAAGGGCAGAGATTTTGCCACAGTGA
GAAAGGTGCTGAGCATGCCCCAAGTGAATATTGTGAAGAAGACTGAGGTG
CAGACAGGAGGCTTCTCTAAGGAGAGCATCCTGCCTAAGAGGAACTCTGA
TAAGCTGATTGCCAGAAAGAAGGACTGGGATCCTAAGAAGTATGGAGGCT
TTGACTCTCCAACAGTGGCCTACTCAGTGCTGGTGGTGGCCAAGGTGGAG
AAGGGCAAGTCTAAGAAGCTGAAGTCTGTGAAGGAGCTGCTGGGCATCAC
CATCATGGAGAGAAGCTCCTTTGAGAAGAATCCTATTGATTTTCTGGAGG
CCAAGGGCTATAAGGAGGTGAAGAAGGACCTGATCATCAAGCTGCCAAAG
TACTCCCTGTTTGAGCTGGAGAATGGCAGGAAGAGAATGCTGGCATCTGC
TGGAGAGCTGCAGAAGGGCAATGAGCTGGCCCTGCCCAGCAAGTATGTGA
ACTTCCTGTATCTGGCCTCCCACTATGAGAAGCTGAAGGGCTCCCCTGAG
GATAATGAGCAGAAGCAGCTGTTTGTGGAGCAGCACAAGCACTATCTGGA
TGAGATCATTGAGCAGATCTCAGAGTTCTCTAAGAGAGTGATCCTGGCTG
ATGCCAATCTGGATAAGGTGCTGAGTGCCTACAACAAGCACAGGGATAAG
CCAATCAGAGAGCAGGCAGAGAATATCATCCACCTGTTCACCCTGACAAA
CCTGGGAGCACCAGCAGCCTTCAAGTATTTTGACACCACAATTGATAGGA
AGAGGTACACCTCCACAAAGGAGGTGCTGGATGCCACCCTGATCCACCAG
AGCATCACAGGCCTGTATGAGACAAGGATTGACCTGTCCCAGCTGGGAGG
AGACCCAAGAAGAAGAGGAAGGTGTGA
```

Liver Optimized Cas9-NLS-WCG (SEQ ID NO: 7) was optimized for codon frequencies similar to that of the human liver and contains CpG dinucleotides. SEQ ID NO: 7 has a CAI of 0.96 and a GC content of 58.91.

Liver Optimized Cas9-NLS-WCG (SEQ ID NO: 7) is shown below:

```
                                        (SEQ ID NO: 7)
ATGGACAAGAAGTACTCCATCGGCCTGGACATCGGGACCAACAGCGTGGG

CTGGGCCGTGATCACCGACGAGTACAAGGTGCCCTCCAAGAAGTTCAAGG

TGCTGGGGAACACCGACAGACACAGCATCAAGAAGAACCTGATCGGCGCC

CTGCTGTTCGACTCCGGAGAAACCGCTGAGGCTACCCGCCTGAAGAGAAC

CGCTCGCCGGAGGTACACCAGACGCAAGAACAGGATCTGCTACCTGCAGG

AGATCTTCTCCAACGAGATGGCCAAGGTGGACGACTCCTTCTTCCACCGG

CTGGAGGAGAGCTTCCTGGTGGAGGAGGACAAGAAGCACGAGAGGCACCC

CATCTTCGGCAACATCGTGGACGAGGTGGCCTACCACGAGAAGTACCCCA

CCATCTACCACCTGAGGAAGAAGCTGGTGGACTCCACCGACAAGGCCGAC

CTGAGACTGATCTACCTGGCCCTGGCCCACATGATCAAGTTCCGCGGCCA

CTTCCTGATCGAGGGGGACCTGAACCCCGACAACAGCGACGTGGACAAGC

TGTTCATCCAGCTGGTGCAGACCTACAACCAGCTGTTCGAGGAGAACCCC

ATCAACGCTTCCGGAGTGGACGCTAAGGCTATCCTGAGCGCCAGACTGTC

CAAGAGCCGGAGGCTGGAGAACCTGATCGCCCAGCTGCCCGGCGAGAAGA

AGAACGGCCTGTTCGGGAACCTGATCGCCCTGTCCCTGGGGCTGACCCCC

AACTTCAAGAGCAATTTCGACCTGGCCGAGGACGCCAAGCTGCAGCTGTC

CAAGGACACCTACGACGACGACCTGGACAACCTGCTGGCCCAGATCGGCG

ACCAGTACGCCGACCTGTTCCTGGCCGCCAAGAACCTGTCCGACGCCATC

CTGCTGAGCGACATCCTGCGCGTGAACACCGAGATCACCAAGGCCCCCCT

GTCCGCCAGCATGATCAAGAGATACGACGAGCACCACCAGGACCTGACCC

TGCTGAAGGCCCTGGTGCGCCAGCAGCTGCCCGAGAAGTACAAGGAGATC

TTCTTCGACCAGAGCAAGAACGGATACGCTGGATACATCGACGGAGGAGC

CTCCCAGGAGGAGTTCTACAAGTTCATCAAGCCCATCCTGGAGAAGATGG

ACGGCACCGAGGAGCTGCTGGTGAAGCTGAACCGGGAGGACCTGCTGAGG

AAGCAGAGAACCTTCGACAACGGCTCCATCCCCCACCAGATCCACCTGGG

GGAGCTGCACGCCATCCTGAGACGCCAGGAGGACTTCTACCCCTTCCTGA

AGGACAACAGGGAGAAGATCGAGAAGATCCTGACCTTCAGAATCCCATAC

TACGTGGGACCACTGGCTAGGGGAAACTCCAGATTCGCCTGGATGACCCG

GAAGAGCGAGGAAACCATCACCCCCTGGAACTTCGAGGAGGTGGTGGACA

AGGGGAGCTTCCGCCCAGAGCTTCATCGAGAGGATGACCAACTTCGACAAG

AACCTGCCCAACGAGAAGGTGCTGCCCAAGCACTCCCTGCTGTACGAGTA

CTTCACCGTGTACAACGAGCTGACCAAGGTGAAGTACGTGACCGAGGGCA

TGAGAAAGCCCGCCTTCCTGAGCGGGGAGCAGAAGAAGGCCATCGTGGAC

CTGCTGTTCAAGACCAACCGCAAGGTGACCGTGAAGCAGCTGAAGGAGGA

CTACTTCAAGAAGATCGAGTGCTTCGACTCCGTGGAGATCAGCGGAGTGG

AGGACCGCTTCAACGCTTCCCTGGGGACCTACCACGACCTGCTGAAGATC

ATCAAGGACAAGGACTTCCTGGACAACGAGGAGAACGAGGACATCCTGGA

GGACATCGTGCTGACCCTGACCCTGTTCGAGGACCGCGAGATGATCGAGG

AGCGGCTGAAGACCTACGCCCACCTGTTCGACGACAAGGTCATGAAGCAG

CTGAAGCGGAGGAGATACACCGGATGGGGCGCCTGAGCAGAAAGCTGAT

CAACGGCATCCGGGACAAGCAGTCCGGGAAGACCATCCTGGACTTCCTGA

AGAGCGACGGCTTCGCCAACAGGAACTTCATGCAGCTGATCCACGACGAC

TCCCTGACCTTCAAGGAGGACATCCAGAAGGCTCAGGTGTCCGGACAGGG
```

```
GGACAGCCTGCACGAGCACATCGCTAACCTGGCTGGCAGCCCCGCCATCA
AGAAGGGGATCCTGCAGACCGTGAAGGTGGTGGACGAGCTGGTGAAGGTC
ATGGGCAGGCACAAGCCCGAGAACATCGTGATCGAGATGGCCAGAGAGAA
CCAGACCACCCAGAAGGGGCAGAAGAACTCCCGCGAGCGGATGAAGAGGA
TCGAGGAGGGCATCAAGGAGCTGGGGAGCCAGATCCTGAAGGAGCACCCC
GTGGAGAACACCCAGCTGCAGAACGAGAAGCTGTACCTGTACTACCTGCA
GAACGGCCGCGACATGTACGTGGACCAGGAGCTGGACATCAACCGGCTGT
CCGACTACGACGTGGACCACATCGTGCCCCAGTCCTTCCTGAAGGACGAC
AGCATCGACAACAAGGTGCTGACCCGCAGCGACAAGAACCGGGGGAAGTC
CGACAACGTGCCCAGCGAGGAGGTGGTGAAGAAGATGAAGAACTACTGGC
GCCAGCTGCTGAACGCCAAGCTGATCACCCAGCGCAAGTTCGACAACCTG
ACCAAGGCTGAGAGAGGAGGGCTGTCCGAGCTGGACAAGGCCGGCTTCAT
CAAGAGGCAGCTGGTGGAAACCAGACAGATCACCAAGCACGTGGCCCAGA
TCCTGGACAGCCGGATGAACACCAAGTACGACGAGAACGACAAGCTGATC
AGGGAGGTGAAGGTCATCACCCTGAAGTCCAAGCTGGTGAGCGACTTCCG
CAAGGACTTCCAGTTCTACAAGGTGCGGGAGATCAACAACTACCACCACG
CCCACGACGCTTACCTGAACGCTGTGGTGGGAACCGCCCTGATCAAGAAG
TACCCCAAGCTGGAGTCCGAGTTCGTGTACGGGGACTACAAGGTGTACGA
CGTGCGCAAGATGATCGCCAAGTCCGAGCAGGAGATCGGCAAGGCCACCG
CCAAGTACTTCTTCTACAGCAACATCATGAACTTCTTCAAGACCGAGATC
ACCCTGGCCAACGGCGAGATCAGGAAGCGCCCCCTGATCGAAACCAACGG
CGAAACCGGAGAGATCGTGTGGGACAAGGGAAGAGACTTCGCTACCGTGC
GGAAGGTGCTGTCCATGCCCCAGGTGAACATCGTGAAGAAGACCGAGGTG
CAGACCGGCGGGTTCTCCAAGGAGAGCATCCTGCCCAAGAGGAACAGCGA
CAAGCTGATCGCCAGAAAGAAGGACTGGGACCCCAAGAAGTACGGAGGAT
TCGACTCCCCAACCGTGGCTTACAGCGTGCTGGTGGTGGCCAAGGTGGAG
AAGGGCAAGTCCAAGAAGCTGAAGAGCGTGAAGGAGCTGCTGGGGATCAC
CATCATGGAGCGGTCCAGCTTCGAAGAACCCCATCGACTTCCTGGAGG
CCAAGGGCTACAAGGAGGTGAAGAAGGACCTGATCATCAAGCTGCCCAAG
TACAGCCTGTTCGAGCTGGAGAACGGAAGAAAGAGAATGCTGGCTTCCGC
CGGAGAGCTGCAGAAGGGAAACGAGCTGGCCCTGCCCAGCAAGTACGTGA
ACTTCCTGTACCTGGCCTCCCACTACGAGAAGCTGAAGGGCAGCCCCGAG
GACAACGAGCAGAAGCAGCTGTTCGTGGAGCAGCACAAGCACTACCTGGA
CGAGATCATCGAGCAGATCTCCGAGTTCAGCAAGCGCGTGATCCTGGCCG
ACGCCAACCTGGACAAGGTGCTGTCCGCCTACAACAAGCACAGGGACAAG
CCCATCAGAGAGCAGGCCGAGAACATCATCCACCTGTTCACCCTGACCAA
CCTGGGAGCTCCAGCTGCCTTCAAGTACTTCGACACCACCATCGACAGGA
AGAGATACACCAGCACCAAGGAGGTGCTGGACGCCACCCTGATCCACCAG
TCCATCACCGGGCTGTACGAAACCAGAATCGACCTGAGCCAGCTGGGAGG
CGACCCCAAGAAGAAGCGCAAGGTGTGA
```

Example 4: Recombinant AAV Vector for Cas9 Expression

This example illustrates exemplary recombinant AAV vectors encoding a Cas9 under control of a variant promoter of reduced length for optimal AAV vector-based protein expression (that is, a genome of 5 kb or fewer bp).

An exemplary AAV cassette with such a sequence is depicted in FIG. 4. This figure illustrates an AAV cassette for use in the creation of an AAV vector and includes 5' and 3' ITRs, the HCB (SEQ ID NO: 8) promoter, a nucleic acid molecule encoding Cas9 such as SEQ ID NO: 1 or SEQ ID NO: 2, and a synthetic poly A sequence.

HNF1-shortABP-SynO-TSS (also called Hepatic Combinatorial Bundle, or HCB) (SEQ ID NO: 8)

```
GTTAATCATTAAGTCGTTAATTTTTGTGGCCCTTGCGATGTTTGCTCTGG
TTAATAATCTCAGGACAAACAGAGGTTAATAATTTTCCAGATCTCTCTGA
GCAATAGTATAAAAGGCCAGCAGCAGCCTGACCACATCTCATCCTC
```

An exemplary AAV cassette is shown in FIG. 4, which has the following structure:
(5'AAV2 ITR)-(HCB Promoter)-(recombinant Cas9 nucleic acid molecule)-(poly adenylation signal)-(3'AAV2 ITR)

Example 5: Treatment Comprising Recombinant Cas9 Molecules

This example describes an exemplary method for the clinical use of the disclosed recombinant Cas9 sequences SEQ ID NO: 1 and SEQ ID NO: 2.

A patient diagnosed with a disorder affecting proteins produced in the liver, or a liver disorder, such a hemochromatosis and Alpha-1 Antitrypsin Deficiency, is selected for treatment. The patient is administered a therapeutically effective amount of a recombinant AAV comprising the recombinant Cas9 nucleic acid molecule, such as the recombinant Cas9 of SEQ ID NO: 1 or SEQ ID NO: 2 under control of a HCB promoter as disclosed herein. The patient is also administered a therapeutically effective amount of a guide RNA targeted to a gene associated with the diagnosed disorder affecting proteins produced in the liver, or a liver disorder. The guide RNA can be also be contained on an AAV cassette. The recombinant AAVs can be administered intravenously. An appropriate therapeutic dose can be selected by a medical practitioner. In some cases, the therapeutically effective dose is in the range of 1×1011 to 1×1014 viral particles (vp)/kg, such as about 1×1012 vp/kg. In most instances, the patient is administered a single dose. The health of the subject can be monitored over time to determine the effectiveness of the treatment.

It will be apparent that the precise details of the methods or compositions described may be varied or modified without departing from the spirit of the described embodiments. We claim all such modifications and variations that fall within the scope and spirit of the claims below.

We claim:

1. A recombinant nucleic acid molecule comprising a nucleotide sequence encoding Cas9, wherein the sequence is at least 95% identical to SEQ ID NO: 6.

2. The recombinant nucleic acid molecule of claim 1, wherein the nucleotide sequence is at least 98% identical to SEQ ID NO: 6.

3. The recombinant nucleic acid molecule of claim 1, wherein the nucleotide sequence is at least 99% identical to SEQ ID NO: 6.

4. The recombinant nucleic acid molecule of claim 1, wherein the nucleotide sequence is identical to SEQ ID NO: 6.

5. The recombinant nucleic acid molecule of claim 1, wherein the nucleotide sequence is codon-optimized for expression in human liver.

6. The recombinant nucleic acid molecule of claim 1, wherein the nucleotide sequence is isolated.

7. A vector comprising the recombinant nucleic acid molecule of claim 1 operably linked to a promoter.

8. The vector of claim 7, wherein the promoter is a Hepatic Combinatorial Bundle promoter comprising a nucleic acid sequence set forth as SEQ ID NO: 8.

9. The vector of claim 7, wherein the vector is an adeno-associated virus vector.

10. An adeno-associated virus cassette comprising the recombinant nucleic acid molecule of claim 1.

11. The adeno-associated virus cassette of claim 10, wherein the nucleic acid molecule is operably linked to a Hepatic Combinatorial Bundle promoter, left and right inverted terminal repeats, and a synthetic polyadenylation (SpA) signal.

12. A method of making a recombinant adeno-associated virus, comprising:
   introducing the adeno-associated virus vector produced by the cassette of claim 10 into cultured cells;

culturing the cells so that the recombinant adeno-associated virus is produced; and purifying the recombinant adeno-associated virus.

13. A recombinant adeno-associated virus purified according to the method of claim 12.

14. A method for gene-editing liver tissue, comprising:

delivering and expressing a therapeutically effective amount of the recombinant nucleic acid molecule encoding Cas9 of claim 1 to the liver tissue; and delivering a therapeutically effective amount of one or more guide RNAs to the liver tissue, wherein the one or more guide RNAs hybridize with one or more endogenous target sequences and direct sequence-specific binding of the Cas9 to the endogenous target sequence, wherein the Cas9 cleaves the endogenous target sequence.

* * * * *